United States Patent
Dragovich et al.

(10) Patent No.: US 6,534,530 B1
(45) Date of Patent: Mar. 18, 2003

(54) ANTIPICORNAVIRAL COMPOUNDS AND COMPOSITIONS, THEIR PHARMACEUTICAL USES, AND MATERIALS FOR THEIR SYNTHESIS

(75) Inventors: Peter Scott Dragovich, Encinitas, CA (US); Ru Zhou, Carlsbad, CA (US); Stephen Evan Webber, San Diego, CA (US); Thomas J. Prins, Cardiff, CA (US); Siegfried Heinz Reich, Solana Beach, CA (US); Susan E. Kephart, San Diego, CA (US); Yuanjin Rui, San Diego, CA (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/631,708

(22) Filed: Aug. 3, 2000

Related U.S. Application Data

(60) Provisional application No. 60/147,373, filed on Aug. 4, 1999.

(51) Int. Cl.[7] .................... A61K 31/427; A61K 31/428; C07D 417/06; C07D 417/14
(52) U.S. Cl. ................. 514/365; 514/367; 548/180; 548/200
(58) Field of Search .............. 548/180, 200; 514/365, 367

(56) References Cited

U.S. PATENT DOCUMENTS

| | | | |
|---|---|---|---|
| 5,374,623 A | 12/1994 | Zimmerman et al. | 514/17 |
| 5,498,616 A | 3/1996 | Mallamo et al. | 514/300 |
| 5,856,530 A | 1/1999 | Webber et al. | 549/478 |
| 5,962,487 A | 10/1999 | Webber et al. | 514/378 |
| 6,020,371 A | 2/2000 | Dragovich et al. | 514/514 |
| 6,331,554 B1 | 12/2001 | Dragovich et al. | 514/357 |

FOREIGN PATENT DOCUMENTS

| | | |
|---|---|---|
| EP | 0 201844 | 11/1986 |
| WO | WO 92/22570 | 12/1992 |
| WO | WO 94/04172 | 3/1994 |
| WO | WO 95/15749 | 6/1995 |
| WO | 99/31122 | 6/1996 |
| WO | WO 97/19231 | 5/1997 |
| WO | 97/31937 | 9/1997 |
| WO | WO 97/31937 | 9/1997 |
| WO | WO 97/43305 | 11/1997 |
| WO | WO 97/49668 | 12/1997 |
| WO | WO 98/43950 | 10/1998 |
| WO | WO 99/31122 | 6/1999 |
| WO | WO 01/14329 | 3/2001 |
| WO | WO 01/14576 | 3/2001 |

OTHER PUBLICATIONS

Dragovich et al., "Structure–Based Design, Synthesis, and Biological Evaluation of Irreversible Human Rhinovirus 3C Protease Inhibitors. 3. Structure–Activity Studies of Ketomethylene–Containing Peptidomimetics", J. Med. Chem. (1999) vol. 41, No. 7, pp. 1203–1212.

Dragovich et al., "Solid–Phase Synthesis of Irreversible Human Rhinovirus 3C Protease Inhibitors. Part 1: Optimization of Tripeptides Incorporating N–terminal Amides", Bioorg. & Med. Chem. (1999), vol. 7, No. 4, pp. 589–598.

Webber et al., "Tripeptide Aldehyde Inhibitors of Human Rhinovirus 3C Protease: Design, Synthesis, Biological Evaluation, and Cocrystal Structure Solution of $P_1$ Glutamine Isosteric Replacements", J. Med. Chem. (1998), vol. 41, No. 15, pp. 2786–2805.

Dragovich et al., "Structure–Based Design, Synthesis, and Biological Evaluation of Irreversible Human Rhinovirus 3C Protease Inhibitors. 1. Michael Acceptor Structure–Activity Studies", J. Med. Chem. (1998), vol. 41, No. 15, pp. 2806–2818.

Dragovich et al., "Structure–Based Design, Synthesis, and Biological Evaluation of Irreversible Human Rhinovirus 3C Protease Inhibitors. 4. Incorporation of $P_1$ Lactam Moieties as L–Glutamine Replavements", J. Med. Chem. (1999) vol. 42, No. 7, pp. 1213–1224.

Weislow et al., "New Soluble–Formazan Assay for HIV–1 Cytopathic Effects: Application to High–Flux Screening of Synthetic and Natural Products for AIDS–Antiviral Activity", J. Natl. Cancer Inst. (1989), vol. 81, No. 8, pp. 577–586.

(List continued on next page.)

*Primary Examiner*—Laura L. Stockton
(74) *Attorney, Agent, or Firm*—Peter Richardson; Bryan C. Zielinski; Karl Neidert

(57) ABSTRACT

Compounds of the formula:

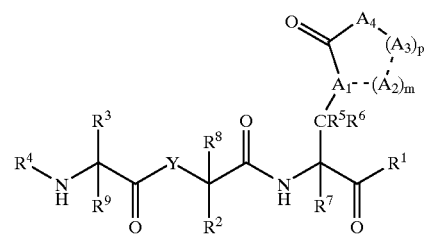

where the formula variables are as defined in the disclosure, advantageously inhibit or block the biological activity of the picornaviral 3C protease. These compounds, as well as pharmaceutical compositions containing these compounds, are useful for treating patients or hosts infected with one or more picornaviruses, such as RVP. Intermediates and synthetic methods for preparing such compounds are also described.

28 Claims, No Drawings

OTHER PUBLICATIONS

Birch et al., "Purification of Recombinant Human Rhinovirus 14 3C Protease Expressed in *Escherichia coli*," Protein Expr. Pur. (1995), vol. 6, No. 5, pp. 609–618.

Diana et al., "Picornavirus Inhibitors: Trifluoromethyl Substitution Provides a Global Protective Effect against Hepatic Metabolism", J. Med. Chem. (1995), vol. 38, No. 8, pp. 1355–1371.

Liu et al., "*Structure–Activity Relationships for Inhibition of Papain by Peptide Michael Acceptors*", J. Med. Chem., 35, 1067–1075 (1992).

DeJohn, et al., "*Functionalization of Substituted 2(1H)– and 4(1H)–Pyridones. III. The Preparation of Substituted 6–Vinyl–1,2–dihydro–2–oxo— and 1,4–Dihydro–4–oxo–3–pyridinecarboxylic Acids through the Chemistry of Pyridone Dianions*", J. Heterocyclic Chem. (1983) vol. 20, No. 5, pp. 1295–1302.

Fasseur et al., "*Studies on Pyrrolidones, Synthesis and N–Alkylation of δ–Enaminoesters Derived from Pyroglutamic Acid*", J. Heterocyclic Chem. (1992) vol. 29, No. 5, pp. 1285–1291.

Straub, et al., "*Synthesis of the Angiotensin Converting enzyme Inhibitor (–)-A58365A via an Isomunchnone cycloaddition Reaction*", Org. Lett. (1999) vol. 1, No. 1, pp. 83–85.

Fang et al., "*Total Synthesis of the Angiotensin–Converting Enzyme Inhibitor A58365A: On the Use of Pyroglutamate as a Chiral Educt*", Tetrahedron Lett. (1989) vol. 30, No. 28, pp. 3621–3624.

Bellus, "*Incorporation of Sulfur Dioxide into the Products of Reaction of Schiff Bases with Halo– or Alkylthio–ketones in Liquid $SO_2$*", Helvetica Chimica Acta (1975) vol. 58, No. 271, pp. 2509–2511.

Luly et al., "*A Synthesis of Protected Aminoalkyl Epoxides from α–Amino Acids*", J. Org. Chem. (1987) vol. 52, No. 8, pp. 1487–1492.

Dragovich, et al., "*Structure–Based Design, Synthesis, and Biological Evaluation of IrreversibleHuman Rhinovirus 3C Protease Inhibitors. 2. Peptide Structure–Activity Studies*", Med Chem. (1998) vol. 41, No. 15, pp. 2819–2834.

Bradbury et al., "*An Efficient Synthesis of the δ–Lactone Corresponding to a Hydroxylethylene Dipeptide Isostere Using Stereoselective Bromolactonisation of a Chiral Acyloxazolidinone*", Tetrahedron Letters (1989) vol. 30, No. 29, pp. 3845–3848.

Dondoni et al., "*Thiazole–Based Stereoselective Routes to Leucine and Phenylalanine Hydroxyethylene Dipeptide Isostere Inhibitors of Renin and HIV–1 Aspartic Protease*", J. Org. Chem. (1995) vol. 60, No. 24, pp. 7927–7933.

McWilliams et al., "*Tandem Asymmetric Transformations: An Asymmetric 1,2–Migration from a Higher Order Zincate Coupled with a Stereoselective Homoaldol Reaction*", J. Am. Chem. Soc. (1996) vol. 118, No. 47, pp. 11970–11971.

Charlton, et al., "*Asymmetric synthesis of lignans using oxazolidinones as chiral auxiliaries*", NRC–CNRC Canadian Journal of Chemistry (1997), vol. 75, No. 8, pp. 1076–1083.

Hoffman, R. V., Tao, J. "*A Simple, Stereoselective Synthesis of Ketomethylene Dipeptide Isosteres*", Tetrahedron (1997) vol. 53, No. 21, pp. 7119–7126.

Kaldor et al., "*Glutamine–Derived Aldehydes for the Inhibition of Human Rhinovirus 3C Protease*", Bioorganic & Medicinal Chemistry Letters, vol. 5, No. 17 (1995) pp. 2021–2026.

Murray et al., "*The enantiospecific synthesis of novel lysine analogues incorporating a pyrrolidine containing side chain*", Tetrahedron Letters, vol. 39 (1998) pp. 6721–6724.

Pegorier et al., "*A General Stereocontrolled Synthesis of Hydroxyethylene Dipeptide Isosteres*", Tetrahedron Letters (1995) vol. 36, No. 16, pp. 2753–2756.

Wuts et al., "*Synthesis of the Hydroxyethylene Isostere of Leu–Val*", J. Org. Chem. (1992) vol. 57, No. 25, pp. 6696–6700.

Ming Tao et al., "*Inhibition of CalPain by Peptidyl Heterocycles*", Bio–org. & Med. Chem. Lett, (1996) vol. 6, No. 24, pp. 3009–3012.

Moss et al., "*Peptidomimetic Inhibitors of Herpes Simplex Virus Ribonucleotide Reductase with Improved Vivo AntiViral Activity*", J. Med. Chem. (1996) vol. 39, No. 21, pp. 4173–4180.

Jones et al, "*A Short Steriocontrolled Synthesis of Hydroxyethylene Dipeptide Isosteres*", J. Org. Chem. (1993), vol. 58, No. 8, pp. 2286–2290.

Veale et al, "*Nonpeptidic Inhibitors of Human Leukocyte Elastase. 5. Design, Synthesis, and x–ray Crystallography of a Series of Orally Active 5–Aminopyrimidin–6–one–Containing Trifluoromethyl Ketones*", J. Med. Chem. (1995), vol. 38, No. 1, pp. 98–108.

Venkatraman et al., "*Synthesis of Potential Inhibitors for Human Rhinovirus 3C Protease*", The Second Winter Conference on Medicinal and Bioorganic Chemistry, Steamboat Springs, CO, Jan. 26–31, 1997.

Peter John Murray, et al. "The enantiospecific synthesis of novel lysine analogues incorporating a pyrrolidine containing side chain", Tetrahedron Letters 39 (1998) 6721–6724.

Ming Tao, et al. "Inhibition of Calpain By Peptidyl Heterocycles", Bioorganic & Medicinal Chemistry Letters, vol. 6, No. 24, pp. 3009–3012, (1996).

ANTIPICORNAVIRAL COMPOUNDS AND COMPOSITIONS, THEIR PHARMACEUTICAL USES, AND MATERIALS FOR THEIR SYNTHESIS

This application claims the benefit of U.S. Provisional Application No. 60/147,373, which was filed on Aug. 4, 1999.

FIELD OF THE INVENTION

The invention pertains to certain peptide-like and peptidomimetic compounds that advantageously inhibit the enzymatic activity of picornaviral 3C proteases, especially rhinovirus 3C proteases (RVPs), and that retard viral growth in cell culture. The invention also relates to the use of such compounds in pharmaceutical compositions and therapeutic treatments for rhinoviral infections. The invention further relates to processes for synthesizing such compounds and compounds useful in such syntheses.

BACKGROUND OF THE INVENTION

The picornaviruses are a family of tiny non-enveloped positive-stranded RNA-containing viruses that infect humans and other animals. These viruses include the human rhinoviruses, human polioviruses, human coxsackieviruses, human echoviruses, human and bovine enteroviruses, encephalomyocarditis viruses, meningitis virus, foot and mouth viruses, hepatitis A virus, and others. The human rhinoviruses are a major cause of the common cold. To date, there are no effective therapies on the market that cure the common cold, only treatments that relieve the symptoms.

Picornaviral infections may be treated by inhibiting the proteolytic 3C enzymes. These enzymes are required for the natural maturation of the picornaviruses. They are responsible for the autocatalytic cleavage of the genomic, large polyprotein into the essential viral proteins. Members of the 3C protease family are cysteine proteases, where the sulfhydryl group most often cleaves the glutamine-glycine amide bond. Inhibition of 3C proteases is believed to block proteolytic cleavage of the polyprotein, which in turn can retard the maturation and replication of the viruses by interfering with viral particle production. Therefore, inhibiting the processing of this cysteine protease with selective small molecules that are specifically recognized should represent an important and useful approach to treat and cure viral infections of this nature and, in particular, the common cold.

Some small-molecule inhibitors of the enzymatic activity of picornaviral 3C proteases (i.e., antipicornaviral compounds) have been recently discovered. See, for example: U.S. Pat. No. 5,856,530, issued Jan. 5, 1999, to Webber et al.; U.S. patent application Ser. No. 08/991,282, filed Dec. 16, 1997, by Dragovich et al.; U.S. patent application Ser. No. 08/991,739, filed Dec. 16, 1997, by Webber et al.; and U.S. patent application Ser. No. 09/301,977, filed Apr. 29, 1999, by Dragovich et al. See also: Dragovich et al., "Structure-Based Design, Synthesis, and Biological Evaluation of Irreversible Human Rhinovirus 3C Protease Inhibitors . . .," *J. Med. Chem.* (1999), vol. 42, no. 7, 1203–1212, 1213–1224; and Dragovich et al., "Solid-phase Synthesis of Irreversible Human Rhinovirus 3C Protease Inhibitors . . .," *Bioorg. & Med. Chem.* (1999), vol. 7, 589–598. There is still a desire, however, to discover small-molecule compounds that are especially potent antipicornaviral agents.

Inhibitors of other related cysteine proteases such as cathepsins have been described in, e.g., U.S. Pat. No. 5,374,623, issued Dec. 20, 1994, to Zimmermnan et al.; U.S. Pat. No. 5,498,616, issued Mar. 12, 1996, to Mallamo et al.; and WIPO International Publication Nos. WO 94/04172, WO 95/15749, WO 97/19231, and WO 97/49668. There yet remains a need for inhibitors targeting the picornaviral 3C cysteine protease with desirable pharmaceutical properties, such as high specificity.

SUMMARY OF THE INVENTION

Thus, an object of this invention is to discover small-molecule compounds that inhibit picornaviral 3C proteases and are especially potent antipicornaviral agents. A further object of the invention is to provide intermediates useful for the synthesis of protease-inhibiting compounds and synthetic methods useful for such syntheses. A yet further object of the invention is to achieve pharmaceutical compositions that are effective for treating maladies mediated by inhibition of picornaviral 3C proteases, such as the common cold.

Such objects have been attained through the discovery of compounds of the following general formula 1:

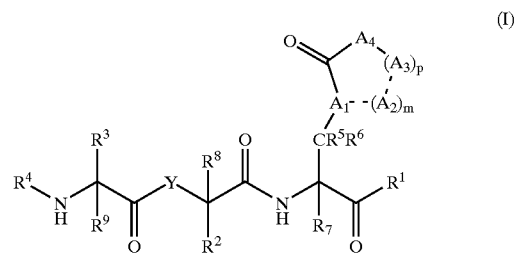

(I)

wherein:

Y is —N($R^y$)—, —C($R^y$)($R^y$)—, or —O—, where each $R^y$ is independently H or lower alkyl; $R^1$ is unsubstituted or substituted alkyl, cycloalkyl, heterocycloalkyl, aryl, heteroaryl, or —C(O)$R^{16}$, where $R^{16}$ is unsubstituted or substituted alkyl, cycloalkyl, heterocycloalkyl, aryl, heteroaryl, alkoxy, cycloalkoxy, heterocycloalkoxy, aryloxy, heteroaryloxy, or amine;

$R^2$ and $R^8$ are each independently H, F, or unsubstituted or substituted alkyl, cycloalkyl, heterocycloalkyl, aryl, or heteroaryl;

$R^3$ and $R^9$ are each independently H or unsubstituted or substituted alkyl, cycloalkyl, heterocycloalkyl, aryl, heteroaryl, —O$R^{17}$, —S$R^{17}$, —N$R^{17}R^{18}$, —N$R^{19}$N$R^{17}R^{18}$, or —N$R^{17}$O$R^{18}$, where $R^{17}$, $R^{18}$, and $R^{19}$ are each independently H, alkyl, cycloalkyl, heterocycloalkyl, aryl, heteroaryl, or acyl;

$R^4$ is a suitable organic moiety;

$R^5$, $R^6$ and $R^7$ are each independently H, F, or lower alkyl;

m is 0 or 1;

p is an integer of from 0 to 5;

$A_1$ is CH or N;

each $A_2$ present is independently C($R^{10}$)($R^{11}$), N($R^{12}$), S, S(O), S(O)$_2$, or O, where each $R^{10}$, $R^{11}$ and $R^{12}$ is independently H or lower alkyl;

each $A_3$ present is independently C($R^{10}$)($R^{11}$), N($R^{12}$), S, S(O), S(O)$_2$, or O, where each $R^{10}$, $R^{11}$ and $R^{12}$ is independently H or lower alkyl;

when p is 1, 2, 3, or 4, $A_4$ is N($R^{13}$), C($R^{10}$)($R^{11}$), or O, and when p is 0 (i.e., $A_3$ is not present), $A_4$ is N($R^{13}$)($R^{14}$), C($R^{10}$)($R^{11}$)($R^{12}$), and O($R^{14}$), provided that when p is 0 and $A_4$ is O($R^{14}$), $A_1$ is not CH, where each $R^{10}$, $R^{11}$ and $R^{12}$ is independently H or lower alkyl, each $R^{13}$ is H, alkyl, aryl, or acyl, and each $R^{14}$ is H, alkyl, or aryl provided that no more than two heteroatoms occur consecutively in the above-depicted ring formed by $A_1$, $(A_2)_m$, $(A_3)_p$, $A_4$, and C=O, where each dotted line in the ring depicts a single bond when $A_2$ is present (i.e., m=1) and a hydrogen atom when $A_2$ is absent (i.e., m=0).

In addition to compounds of the formula I, antipicomaviral agents of the invention include prodrugs, pharmaceutically active metabolites, and pharmaceutically acceptable salts and solvates of such compounds.

In a preferred embodiment of formula I, $R^2$ and $R^8$ are not both hydrogen, and $R^3$ and $R^9$ are not both hydrogen. In another preferred embodiment of formula I: $R^2$ is benzyl optionally substituted with a halogen; $R^3$ is a lower alkyl; $R^4$ is Cbz; and $R^7$, $R^8$, and $R^9$ are each H.

In a preferred embodiment, $R^1$ is a substituted methylene group, for example, —$CH_2NR^{20}R^{21}$, —$CH_2OR^{20}$, —$CH_2OC(O)R^{20}$, —$CH_2ONR^{20}R^{21}$, or —$CH_2SR^{20}$, where $R^{20}$ and $R^{21}$ are each independently selected from H, optionally substituted alkyl, cycloalkyl, heterocycloalkyl, aryl, heteroaryl, and —$C(O)R^{22}$, where $R^{22}$ is selected from optionally substituted alkyl, cycloalkyl, heterocycloalkyl, aryl, heteroaryl, alkoxy, cycloalkoxy, heterocycloalkoxy, aryloxy, heteroaryloxy, and amine, and optionally any two of $R^{20}$, $R^{21}$, and $R^{22}$, together with the atoms to which they are bound, form a 4- to 7-membered ring. In an alternative preferred embodiment, $R^1$ is —$CR^{23}$=$CR^{24}R^{25}$ or —C≡$CR^{26}$, where $R^{23}$, $R^{24}$, $R^{25}$ and $R^{26}$ are each independently selected from H and optionally substituted alkyl, cycloalkyl, heterocycloalkyl, aryl, and heteroaryl. In yet another preferred embodiment, $R^1$ is a —$C(O)R^{16}$ group, where $R^{16}$ is —$NR^{27}R^{28}$, wherein $R^{27}$ and $R^{28}$ are each independently selected from H and optionally substituted alkyl, cycloalkyl, heterocycloalkyl, aryl, and heteroaryl, or $R^{27}$ and $R^{28}$ together with the nitrogen to which they are bound form a 4- to 7-membered heterocyclic ring. In another preferred embodiment, $R^1$ is a mono- or bi-cyclic heteroaryl or aryl group.

Especially preferred compounds are depicted by formula I-a:

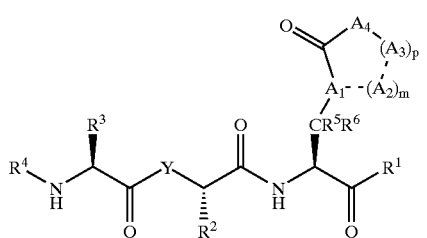

I-a wherein $R^1$ through $R^6$, $A_1$ through $A_4$, m, p, and Y are as defined above.

In preferred embodiments of compounds of the formula I-a, $R^1$ is selected from monocyclic and bicyclic heteroaryl and aryl groups.

$R^2$ in formula I-a is preferably selected from unsubstituted and substituted benzyl groups, preferably benzyl, monosubstituted benzyl, and disubstituted benzyl, where the substituents are independently selected from lower alkyl, lower alkoxy, and halogen.

$R^3$ is preferably an optionally substituted alkyl (e.g., 2-propyl, 2-methyl-2-propyl, or 2-methyl-1-propyl) or arylmethyl (e.g., unsubstituted or substituted phenylmethyl or naphthylmethyl).

$R^4$ is preferably a suitable organic moiety selected from —$[C(O)]_n$—$R^{15}$, where n is 0 or 1 and $R^{15}$ is optionally substituted alkyl, cycloalkyl, aryl, heteroaryl, alkoxy, cycloalkoxy, aryloxy, or heteroaryloxy. In especially preferred embodiments, $R^4$ is benzyloxycarbonyl, arylcarbonyl, or heteroarylcarbonyl, more preferably heteroarylcarbonyl, where the heteroaryl moiety is a five-membered heterocycle having from one to three heteroatoms selected from O, N, and S, more preferably a five-membered heterocycle having at least one nitrogen heteroatom and at least one oxygen heteroatom (e.g., unsubstituted or substituted 1,2-oxazolyl (i.e., isoxazolyl), 1,3-oxazolyl (i.e., oxazolyl), or oxadiazolyl (1,2,3-oxadiazolyl, 1,2,4-oxadiazolyl, or 1,2,5-oxadiazolyl). When the heteroaryl moiety is oxadiazolyl, unsubstituted and monomethyl-substituted 1,2,4-oxadiazolyl are preferred. In especially preferred embodiments, the heteroaryl moiety is 3-isoxazolyl or 5-isoxazolyl, either unsubstituted or substituted with one or two methyl groups and/or halogens (F, Cl, Br or I), with chlorine and fluorine being preferred.

Preferably, the moiety:

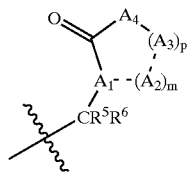

is selected from —$CH_2CH_2C(O)NH_2$; —$CH_2CH_2C(O)NH$-alkyl; —$CH_2NHC(O)CH_3$; and

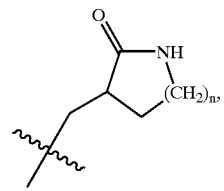

where n is 1 or 2. The moiety is more preferably

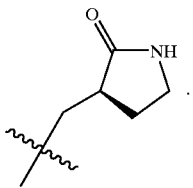

In preferred embodiments, the compounds, prodrugs, pharmaceutically acceptable salts, and pharmaceutically active metabolites and solvates have an antipicomaviral activity with an $EC_{50}$ less than or equal to 100 μM in the H1-HeLa cell culture assay.

The invention is also directed to intermediates of formula II, preferably of the subformula II-a, which are useful in the synthesis of certain compounds of formula I:

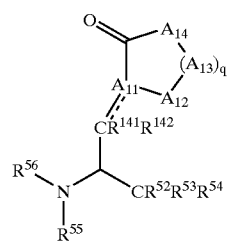

II

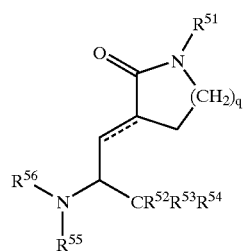

II-a wherein:
q is an integer of from 0 to 5, preferably 1 or 2;
$A_{11}$ is C, CH or N;
$A_{12}$ and each $A_{13}$ are each independently selected from $C(R^{61})(R^{62})$, $N(R^{63})$, S, S(O), $S(O)_2$, and O, where each of $R^{61}$, $R^{62}$ and $R^{63}$ is independently H or lower alkyl;
$A_{14}$ is $NR^{64}$, where $R^{64}$ is H, alkyl, aryl, or acyl, and $R^{64}$ is preferably a suitable protecting group for amide nitrogen;
provided that no more than two heteroatoms occur consecutively in the above-depicted ring in formula II formed by $A_{11}$, $A_{12}$, $(A_{13})_p$, $A_{14}$, and C=O;
$R^{141}$ and $R^{142}$ are each independently H, F or lower alkyl, or $R^{142}$ is absent;
the dotted line depicts an optional valence bond, and when such bond is present, $R^{142}$ is absent and $A_{11}$ is C;
$R^{51}$ is H, alkyl, aryl, or acyl, preferably a protecting group for amide nitrogen;
$R^{52}$, $R^{53}$, and $R^{54}$ are each independently selected from H, hydroxyl, alkyl, acyl, aryl, heteroaryl, suitable protecting groups for carbonyl or hydroxy, $OR^{57}$, and $NR^{57}R^{58}$ where $R^{57}$ is selected from alkyl, aryl and $Si(R^{59})_3$, and $R^{58}$ is selected from alkyl, aryl, alkoxy, aryloxy, and $Si(R^{59})_3$, where each $R^{59}$ is independently alkyl or aryl; or any two of $R^{52}$, $R^{53}$, and $R^{54}$ together form =O; and
$R^{55}$ and $R^{56}$ are each independently H or a suitable protecting group for nitrogen.

Formula II compounds where at least one of $R^{52}$, $R^{53}$, and $R^{54}$ is $NR^{57}R^{58}$ are preferred. In preferred formula II-a embodiments, $R^{52}$ and $R^{53}$ together form =O and $R^{54}$ is selected from alkyl, acyl, aryl, heteroaryl, $OR^{57}$, and $NR^{57}R^{58}$, where $R^{57}$ and $R^{58}$ are as defined above. In other preferred embodiments, $R^{52}$ is H, $R^{53}$ is OH, and $R^{54}$ is selected from alkyl, acyl, aryl, heteroaryl, $OR^{57}$, and $NR^{57}R^{58}$ where $R^{57}$ and $R^{58}$ are as defined above.

The invention is also directed to pharmaceutically acceptable salts of the compounds of formulae II and II-a.

The invention also relates to pharmaceutical compositions containing a therapeutically effective amount of at least one compound of the formula I, or a prodrug, pharmaceutically acceptable salt, pharmaceutically active metabolite, or solvate thereof (collectively, "agents"). Additionally, the invention relates to methods of inhibiting picornaviral 3C protease by administering a therapeutically effective amount of at least one such agent.

DETAILED DESCRIPTION OF THE INVENTION

In accordance with a convention used in the art,

is used in structural formulas herein to depict the bond that is the point of attachment of the moiety or substituent to the core or backbone structure.

As used herein, the term "alkyl group" is intended to mean a straight- or branched-chain monovalent radical of saturated and/or unsaturated carbon atoms and hydrogen atoms, such as methyl (Me), ethyl (Et), propyl, isopropyl, butyl, isobutyl, t-butyl, ethenyl, pentenyl, butenyl, propenyl, ethynyl, butynyl, propynyl, pentynyl, hexynyl, and the like. Unless otherwise indicated, such groups may be unsubstituted (i.e., containing only carbon and hydrogen) or substituted by one or more suitable substituents (e.g., one or more halogens, such as F, Cl, Br, or I, with F and Cl being preferred). A "lower alkyl group" is intended to mean an alkyl group having from 1 to 4 carbon atoms in its chain.

A "cycloalkyl group" is intended to mean a non-aromatic monovalent monocyclic, bicyclic, or tricyclic radical containing from 3 to 14 carbon ring atoms, each of which may be saturated or unsaturated. Unless otherwise indicated, such groups may be unsubstituted or substituted by one or more suitable substituents. Illustrative examples of cycloalkyl groups include the following moieties:

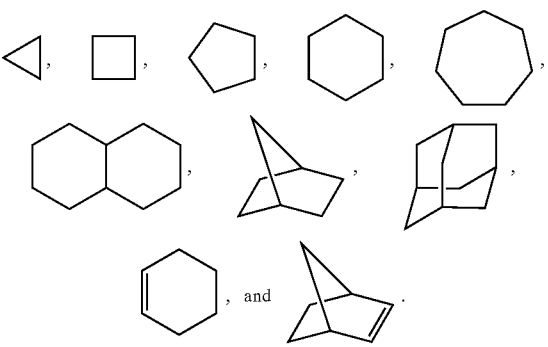

A "heterocycloalkyl group" is intended to mean a non-aromatic monovalent monocyclic, bicyclic, or tricyclic radical, which is saturated or unsaturated, containing from 3 to 18 ring atoms, which includes from 1 to 5 heteroatoms selected from nitrogen, oxygen, and sulfur. Unless otherwise indicates, such radicals may be unsubstituted or substituted by one or more suitable substituents. Illustrative examples of heterocycloalkyl groups include the following moieties:

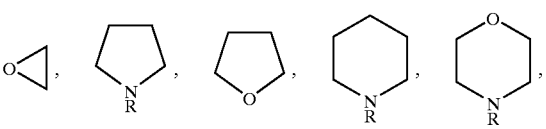

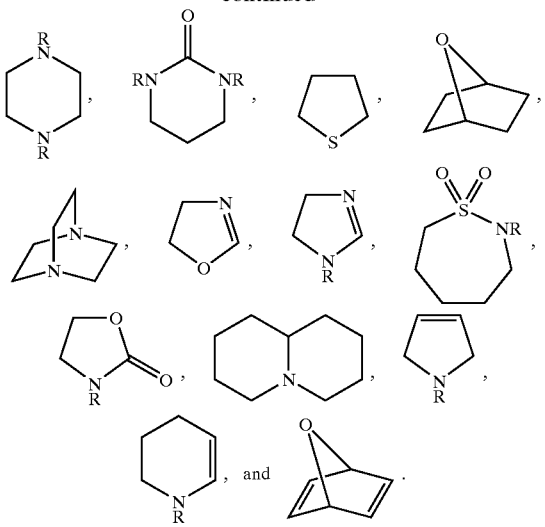

An "aryl group" is intended to mean an aromatic monovalent monocyclic, bicyclic, or tricyclic radical containing from 6 to 18 carbon ring atoms. Unless otherwise indicates, such radicals may be unsubstituted or substituted by one or more suitable substituents. Illustrative examples of aryl groups include the following moieties:

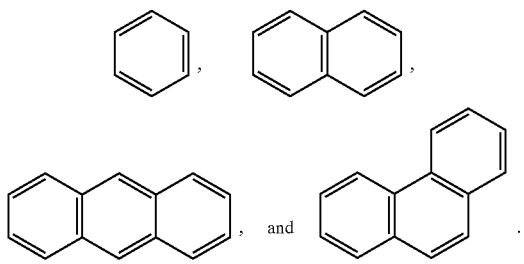

A "heteroaryl group" is intended to mean an aromatic monovalent monocyclic, bicyclic, or tricyclic radical containing from 4 to 18 ring atoms, including from 1 to 5 heteroatoms selected from nitrogen, oxygen, and sulfur. Unless otherwise indicated, such radicals may be unsubstituted or substituted by one or more suitable substituents. Illustrative examples of heteroaryl groups include the following moieties:

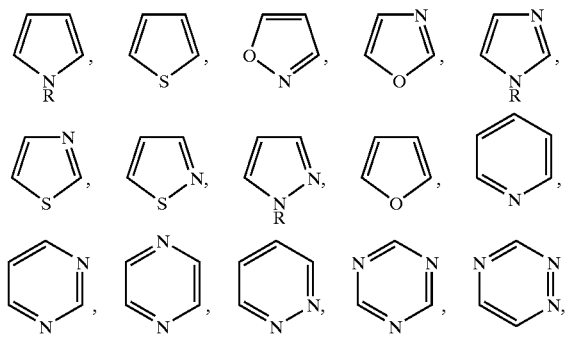

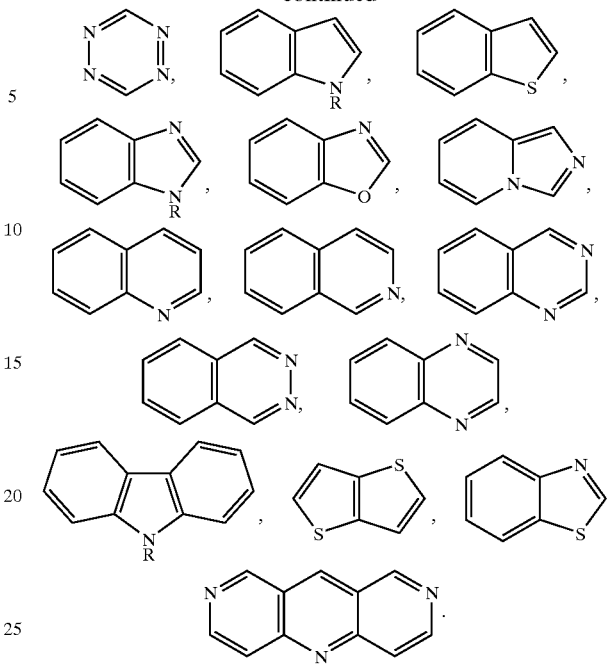

A "heterocycle" is intended to mean a heteroaryl or heterocycloalkyl group.

An "acyl group" is intended to mean a —C(O)—R radical, where R is a suitable substituent.

A "thioacyl group" is intended to mean a —C(S)—R radical, where R is a suitable substituent.

A "sulfonyl group" is intended to mean a —SO$_2$R radical, where R is a suitable substituent.

A "hydroxy group" is intended to mean the radical —OH.

An "amine" or "amino group" is intended to mean the radical —NH$_2$. An "optionally substituted" amines refers to —NH$_2$ groups wherein none, one or two of the hydrogens is replaced by a suitable substituent. Disubstituted amines may have substituents that are bridging, i.e., form a heterocyclic ring structure that includes the amine nitrogen.

An "alkylamino group" is intended to mean the radical —NHR$_a$, where R$_a$ is an alkyl group.

A "dialkylamino group" is intended to mean the radical —NR$_a$R$_b$, where R$_a$ and R$_b$ are each independently an alkyl group.

An "alkoxy group" is intended to mean the radical —OR$_a$, where R$_a$ is an alkyl group. Exemplary alkoxy groups include methoxy, ethoxy, propoxy, and the like. "Lower alkoxy" groups have alkyl moieties having from 1 to 4 carbons.

An "alkoxycarbonyl group" is intended to mean the radical —C(O)OR$_a$, where R$_a$ is an alkyl group.

An "alkylsulfonyl group" is intended to mean the radical —SO$_2$R$_a$, where R$_a$ is an alkyl group.

An "alkylaminocarbonyl group" is intended to mean the radical —C(O)NHR$_a$, where R$_a$ is an alkyl group.

A "dialkylaminocarbonyl group" is intended to mean the radical —C(O)NR$_a$R$_b$, where R$_a$ and R$_b$ are each independently an alkyl group.

A "mercapto group" is intended to mean the radical —SH.

An "alkylthio group" is intended to mean the radical —SR$_a$, where R$_a$ is an alkyl group.

A "carboxy group" is intended to mean the radical —C(O)OH.

A "carbamoyl group" is intended to mean the radical —C(O)NH$_2$.

An "aryloxy group" is intended to mean the radical —OR$_c$, where R$_c$ is an aryl group.

A "heteroaryloxy group" is intended to mean the radical —OR$_d$, where R$_d$ is a heteroaryl group.

An "arylthio group" is intended to mean the radical —SR$_c$, where R$_c$ is an aryl group.

A "heteroarylthio group" is intended to mean the radical —SR$_d$, where R$_d$ is a heteroaryl group.

The term "suitable organic moiety" is intended to mean any organic moiety recognizable, such as by routine testing, to those skilled in the art as not adversely affecting the inhibitory activity of the inventive compounds. Illustrative examples of suitable organic moieties include, but are not limited to, hydroxy groups, alkyl groups, oxo groups, cycloalkyl groups, heterocycloalkyl groups, aryl groups, heteroaryl groups, acyl groups, sulfonyl groups, mercapto groups, alkylthio groups, alkoxy groups, carboxy groups, amino groups, alkylamino groups, dialkylamino groups, carbamoyl groups, arylthio groups, heteroarylthio groups, and the like.

The term "substituent" or "suitable substituent" is intended to mean any suitable substituent that may be recognized or selected, such as through routine testing, by those skilled in the art. Illustrative examples of suitable substituents include hydroxy groups, halogens, oxo groups, alkyl groups, acyl groups, sulfonyl groups, mercapto groups, alkylthio groups, alkoxy groups, cycloalkyl groups, heterocycloalkyl groups, aryl groups, heteroaryl groups, carboxy groups, amino groups, alkylamino groups, dialkylamino groups, carbamoyl groups, aryloxy groups, heteroaryloxy groups, arylthio groups, heteroarylthio groups, and the like.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. Various groups may be unsubstituted or substituted (i.e., they are optionally substituted) as indicated.

A "prodrug" is intended to mean a compound that is converted under physiological conditions or by solvolysis or metabolically to a specified compound that is pharmaceutically active.

A "pharmaceutically active metabolite" is intended to mean a pharmacologically active compound produced through metabolism in the body of a specified compound.

A "solvate" is intended to mean a pharmaceutically acceptable solvate form of a specified compound that retains the biological effectiveness of such compound. Examples of solvates include compounds of the invention in combination with water, isopropanol, ethanol, methanol, DMSO, ethyl acetate, acetic acid, or ethanolamine.

A "pharmaceutically acceptable salt" is intended to mean a salt that retains the biological effectiveness of the free acids and bases of a specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates.

If an inventive compound is a base, a desired salt may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid or ethanesulfonic acid, or the like.

If an inventive compound is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Illustrative examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

In the case of compounds, salts, or solvates that are solids, it is understood by those skilled in the art that the inventive compounds, salts, and solvates may exist in different crystal forms, all of which are intended to be within the scope of the present invention and specified formulas.

The inventive compounds may exist as single stereoisomers, racemates, and/or mixtures of enantiomers and/or diastereomers. All such single stereoisomers, racemates, and mixtures thereof are intended to be within the broad scope of the present invention. Preferably, however, the inventive compounds are used in optically pure form.

As used herein, the term "optically pure" is intended to mean a compound comprising at least a sufficient amount of a single enantiomer to yield a compound having the desired pharmacological activity. Preferably, an optically pure compound of the invention comprises at least 90% of a single isomer (80% enantiomeric excess), more preferably at least 95% (90% e.e.), even more preferably at least 97.5% (95% e.e.), and most preferably at least 99% (98% e.e.).

Preferably, the compounds of formula I and their pharmaceutically acceptable salts, prodrugs, active metabolites, and solvates have antipicornaviral activity, more preferably antirhinoviral activity, corresponding to an EC$_{50}$ less than or equal to 100 μM in the H1-HeLa cell culture assay.

In preferred embodiments, the formula I compounds are of sub-formula I-a as defined above. Especially preferred embodiments of the invention have formula I-b:

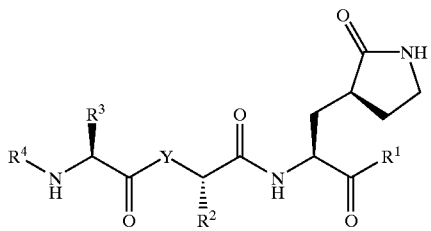

I-b

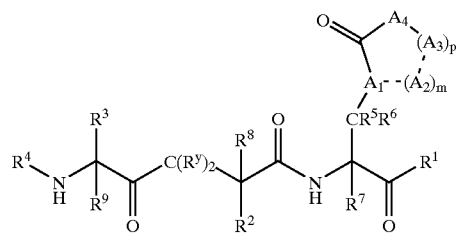

I-e where $R^1$ through $R^4$ are as defined above. In especially preferred embodiments of formula I-b, $R^1$ is mono- or bi-cyclic heteroaryl. Preferably, $R^2$ is selected from unsubstituted, mono-substituted, and disubstituted benzyl groups, where the substituents are independently selected from lower alkyl, lower alkoxy, and halogen. $R^3$ is preferably alkyl (e.g., 2-propyl, 2-methyl-2-propyl, or 2-methyl-1-propyl) or arylmethyl (e.g., unsubstituted or substituted phenylmethyl or naphthylmethyl). The variable $R^4$ is preferably benzyloxycarbonyl, arylcarbonyl, or heteroarylcarbonyl, more preferably heteroarylcarbonyl, where the heteroaryl moiety is a five-membered heterocycle having from one to three heteroatoms selected from O, N, and S. More preferably $R^4$ is a five-membered heterocycle having at least one nitrogen heteroatom and at least one oxygen heteroatom (e.g., unsubstituted or substituted 1,2-oxazolyl (i.e., isoxazolyl), 1,3-oxazolyl (i.e., oxazolyl), or oxadiazolyl (1,2,3-oxadiazolyl, 1,2,4-oxadiazolyl, or 1,2,5-oxadiazolyl); preferred oxadiazolyls are unsubstituted and monomethyl-substituted 1,2,4-oxadiazolyl. In especially preferred embodiments, the heteroaryl moiety is 3-isoxazolyl or 5-isoxazolyl, either unsubstituted or substituted with one or two substituents selected from methyl and halogens, with chlorine and fluorine being preferred halogen substituents.

Varying the group Y in formula I gives rise to formulae I-c (peptides), I-d (depsipeptides), and I-e (ketomethylenes), where all variables are as defined previously:

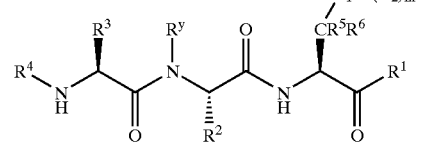

I-c

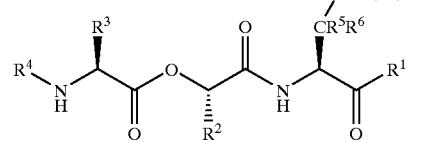

I-d

Preferred embodiments of formula I-a are shown in formulae I-f, I-g and I-h below:

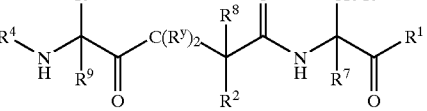

I-f

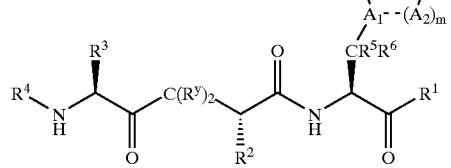

I-g

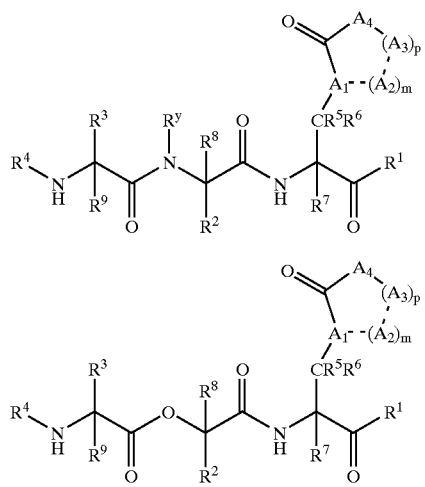

I-h

In the compounds of formulae I-c, I-e, I-f, and I-h, $R^y$ is preferably H or methyl. Preferred specific compounds include those of the Examples below, especially:

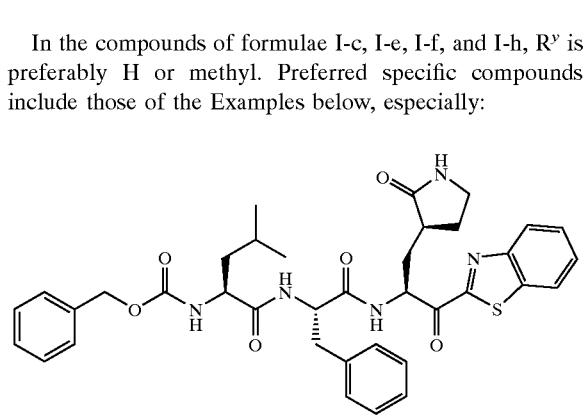

and

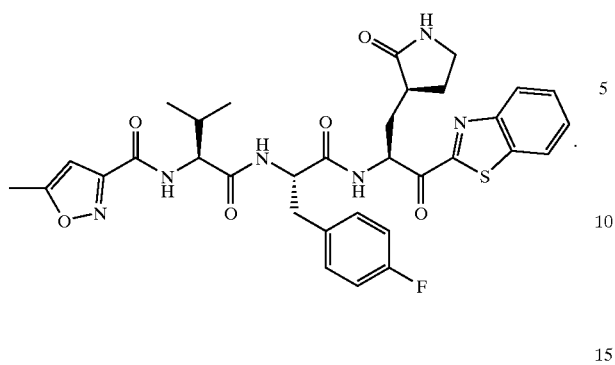

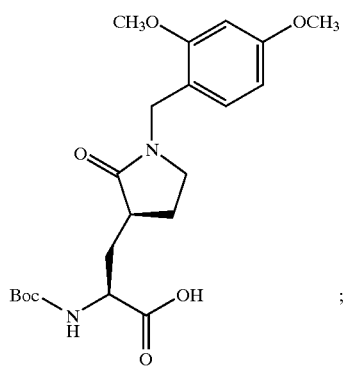

In another aspect, the invention is directed to intermediates of formula 11, preferably of the sub-formula II-a, which are useful in the synthesis of various compounds of formula I:

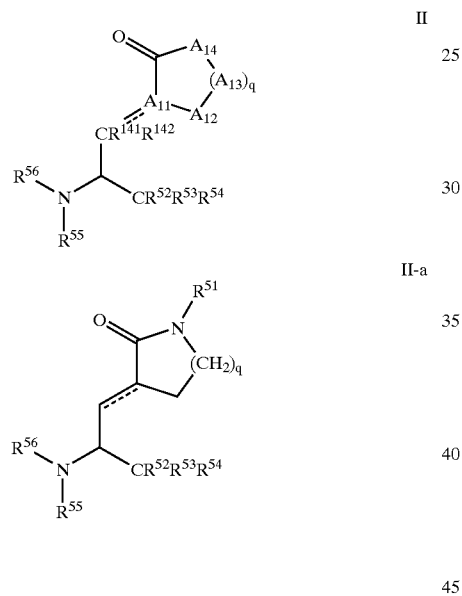

wherein all variables are as defined above. Preferred $R^{55}$ and $R^{56}$ groups are H and suitable protecting groups for nitrogen, for example, Boc (t-butyloxycarbonyl), Cbz (benzyloxycarbonyl), FMOC (fluorene-9-methyloxycarbonyl), other alkyloxycarbonyls (e.g., methyloxycarbonyl), and trityl (triphenylmethyl). Other suitable nitrogen-protecting groups may be readily selected by artisans (see, e.g., Greene and Wuts, *Protecting Groups in Chemical Synthesis* (3$^{rd}$ ed.), John Wiley & Sons, NY (1999)). Preferred groups for $R^{52}$, $R^{53}$, and $R^{54}$ are H, alkoxy, hydroxy, carbonyl, $OR^{59}$, and suitable protecting groups for carbonyl or hydroxy. A preferred protecting group for hydroxy is t-butyldimethylsilyl (TBS).

Preferred examples of the formula II useful as intermediates include the following:

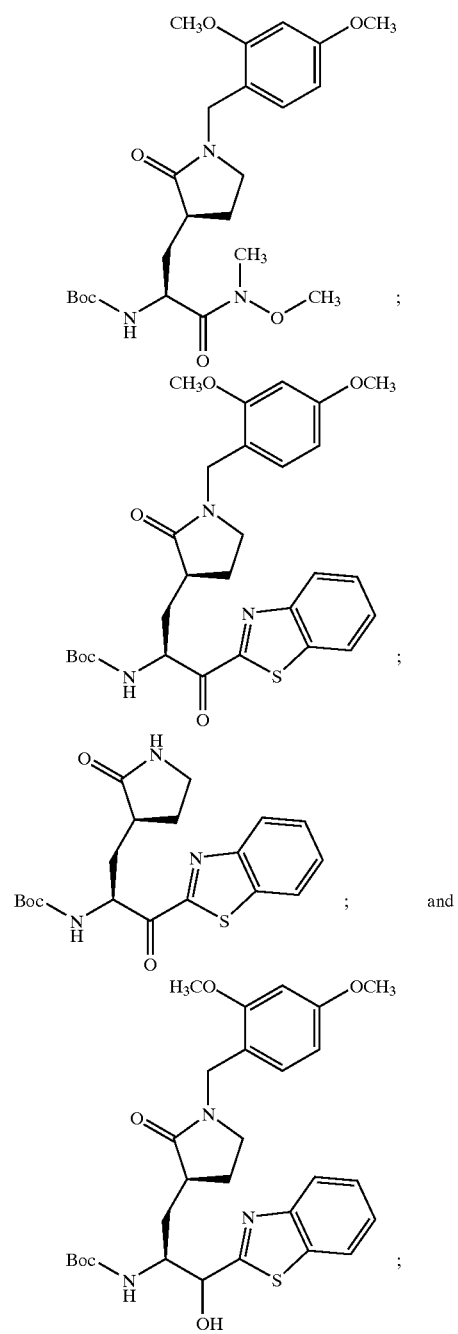

and pharmaceutically acceptable salts thereof.

The present invention is also directed to a method of inhibiting picornaviral 3C protease activity, comprising contacting the protease with an effective amount of a compound of formula I, or a pharmaceutically acceptable salt, prodrug, pharmaceutically active metabolite, or solvate thereof. For example, picornaviral 3C protease activity may be inhibited in mammalian tissue by administering a compound of formula I or a pharmaceutically acceptable salt, prodrug, pharmaceutically active metabolite, or solvate thereof. More preferably, the present method is directed at inhibiting rhinoviral protease activity.

"Treating" or "treatment" is intended to mean at least the mitigation of a disease condition in a mammal, such as a human, that is alleviated by the inhibition of the activity of one or more picornaviral 3C proteases, such as human rhinoviruses, human poliovirus, human coxsackieviruses, encephalomyocarditis viruses, meningitis virus, and hepatitis A virus, and includes: (a) prophylactic treatment in a mammal, particularly when the mammal is found to be predisposed to having the disease condition but not yet diagnosed as having it; (b) inhibiting the disease condition; and/or (c) alleviating, in whole or in part, the disease condition.

The activity of the inventive compounds as inhibitors of picornaviral 3C protease activity may be measured by any of the suitable methods known to those skilled in the art, including in vivo and in vitro assays. An example of a suitable assay for activity measurements is the antiviral H1-HeLa cell culture assay described herein.

Administration of the compounds of the formula I and their pharmaceutically acceptable prodrugs, salts, active metabolites, and solvates may be performed according to any of the generally accepted modes of administration available to those skilled in the art. Illustrative examples of suitable modes of administration include oral, nasal, parenteral, topical, transdermal, and rectal. Intranasal delivery is preferred.

An inventive compound of formula I or a pharmaceutically acceptable salt, prodrug, active metabolite, or solvate thereof may be administered as a pharmaceutical composition in any pharmaceutical form recognizable to the skilled artisan as being suitable. Suitable pharmaceutical forms include solid, semisolid, liquid, or lyophilized formulations, such as tablets, powders, capsules, suppositories, suspensions, liposomes, and aerosols. Pharmaceutical compositions of the invention may also include suitable excipients, diluents, vehicles, and carriers, as well as other pharmaceutically active agents, depending upon the intended use or mode of administration. In preferred embodiments, the inventive pharmaceutical compositions are delivered intranasally in the form of suspensions.

Acceptable methods of preparing suitable pharmaceutical forms of the pharmaceutical compositions may be routinely determined by those skilled in the art. For example, pharmaceutical preparations may be prepared following conventional techniques of the pharmaceutical chemist involving steps such as mixing, granulating, and compressing when necessary for tablet forms, or mixing, filling, and dissolving the ingredients as appropriate, to give the desired products for oral, parenteral, topical, intravaginal, intranasal, intrabronchial, intraocular, intraaural, and/or rectal administration.

Solid or liquid pharmaceutically acceptable carriers, diluents, vehicles, or excipients may be employed in the pharmaceutical compositions. Illustrative solid carriers include starch, lactose, calcium sulfate dihydrate, terra alba, sucrose, talc, gelatin, pectin, acacia, magnesium stearate, and stearic acid. Illustrative liquid carriers include syrup, peanut oil, olive oil, saline solution, and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., solution), or a non-aqueous or aqueous liquid suspension.

A dose of the pharmaceutical composition contains at least a therapeutically effective amount of the active compound (i.e., a compound of formula I or a pharmaceutically acceptable salt, prodrug, active metabolite, or solvate thereof), and preferably is made up of one or more pharmaceutical dosage units. The selected dose may be administered to a mammal, for example, a human patient, in need of treatment mediated by inhibition of picornaviral 3C protease activity, by any known or suitable method of administering the dose, including: topically, for example, as an ointment or cream; orally; rectally, for example, as a suppository; parenterally by injection; or continuously by intravaginal, intranasal, intrabronchial, intraaural, or intraocular infusion.

A "therapeutically effective amount" is intended to mean the amount of an inventive agent that, when administered to a mammal in need thereof, is sufficient to effect treatment for disease conditions alleviated by the inhibition of the activity of one or more picornaviral 3C proteases, such as human rhinoviruses, human poliovirus, human coxsackieviruses, encephalomyocarditis viruses, menigovirus, and hepatitis A virus. The amount of a given compound of the invention that will be therapeutically effective will vary depending upon factors such as the particular compound, the disease condition and the severity thereof, the identity of the mammal in need thereof, which amount may be routinely determined by artisans.

By way of illustration, a formulation for nasal delivery of the inventive compounds for treatment of rhinoviral infections may include a compound of formula I that is micronized to a reduced particle size in a suspension containing a final concentration of from about 0.01% to about 2% of the active compound, preferably about from 0.2% to 2%.

An exemplary nasal formulation is as follows: 2.0 weight percent of micronized compound of formula I-a; 1.2 weight percent of a mixture of microcrystalline cellulose and carboxymethyl cellulose sodium (e.g., Avicel RC/CL); 0.1 weight percent of polysorbate 80; 0.01 weight percent of disodium ethylenediamine tetraacetate (EDTA); 0.02 weight percent of benzalkonium chloride solution (50 wt. % BzCl); 5.0 weight percent of dextrose (anhydrous); and balance of purified water.

General Syntheses

The inventive compounds of formula I may be advantageously prepared by the methods of the present invention, including the general methods described below. In each of these general methods, the variables are as defined above.

When stereochemistry is not specified in chemical structures, either stereocenter may be utilized. The following abbreviations also apply: Boc (tert-butoxycarbonyl), Ac (acetyl), Cbz (benzyloxycarbonyl), and Tr (triphenylmethyl).

General Scheme 1

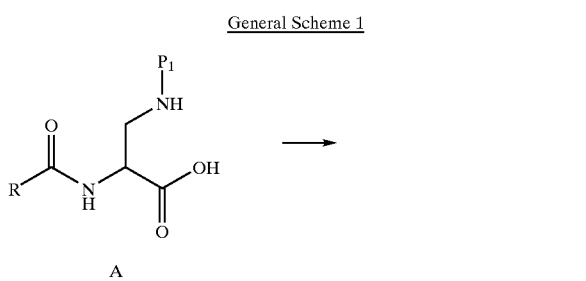

In this general synthesis scheme, an amino acid A (prepared by standard peptide coupling conditions and/or methods known in the art), where $P_1$ is an appropriate protecting group for nitrogen (e.g., Boc or Ac) and R is a suitable organic moiety (e.g., Cbz-L-Leu-L-Phe-), is transformed into Weinreb amide B. Compound B is treated with an excess of an organometallic reagent (e.g., an alkyllithium or Grignard reagent) to provide product C. At this point, the $P_1$ nitrogen protecting group present in C may be exchanged for an alternate if necessary (e.g., Boc exchanged for Ac).

General Scheme 2

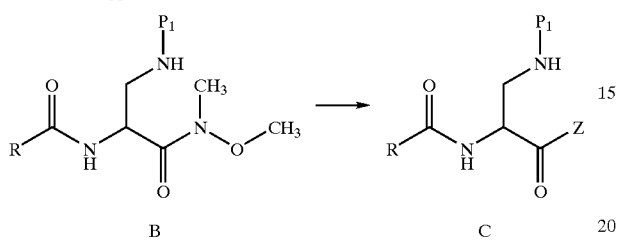

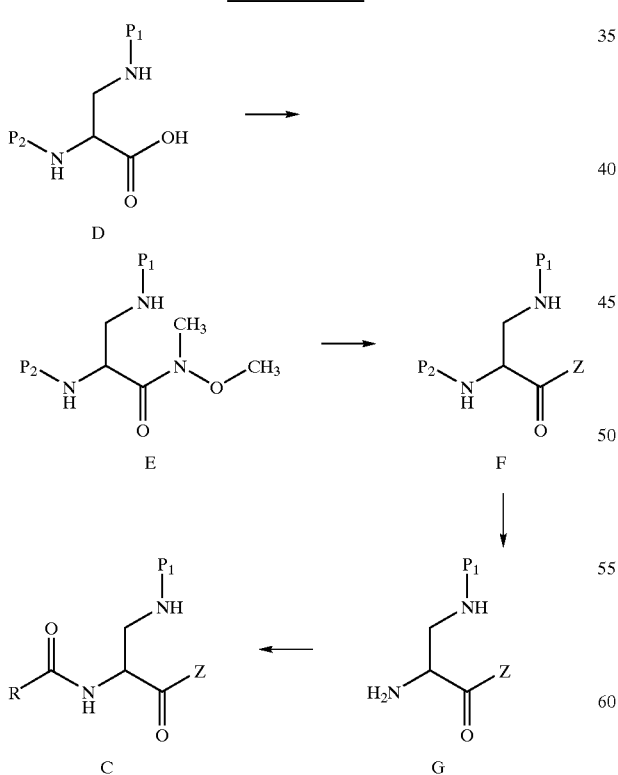

An alternate method of preparing product C is depicted above. In this general method, amino acid D (prepared by known methods), where $P_1$ is an appropriate protecting group for nitrogen (e.g., Boc or Ac) and $P_2$ is an appropriate orthogonal protecting group for nitrogen (e.g., Cbz), is transformed into Weinreb amide E. Compound E is treated with an excess of an organometallic reagent (e.g., an alkyllithium or Grignard reagent) to provide intermediate F. The $P_2$ protecting group present in F is then removed, and the resulting amine G (or salt thereof) is derivatized (coupled) with a suitable organic moiety (e.g., Cbz-L-Leu-L-Phe-) to afford product C. As described above, the $P_1$ nitrogen protecting group present in C may be exchanged at this point for an alternate if necessary (e.g., Boc exchanged for Ac).

General Scheme 3

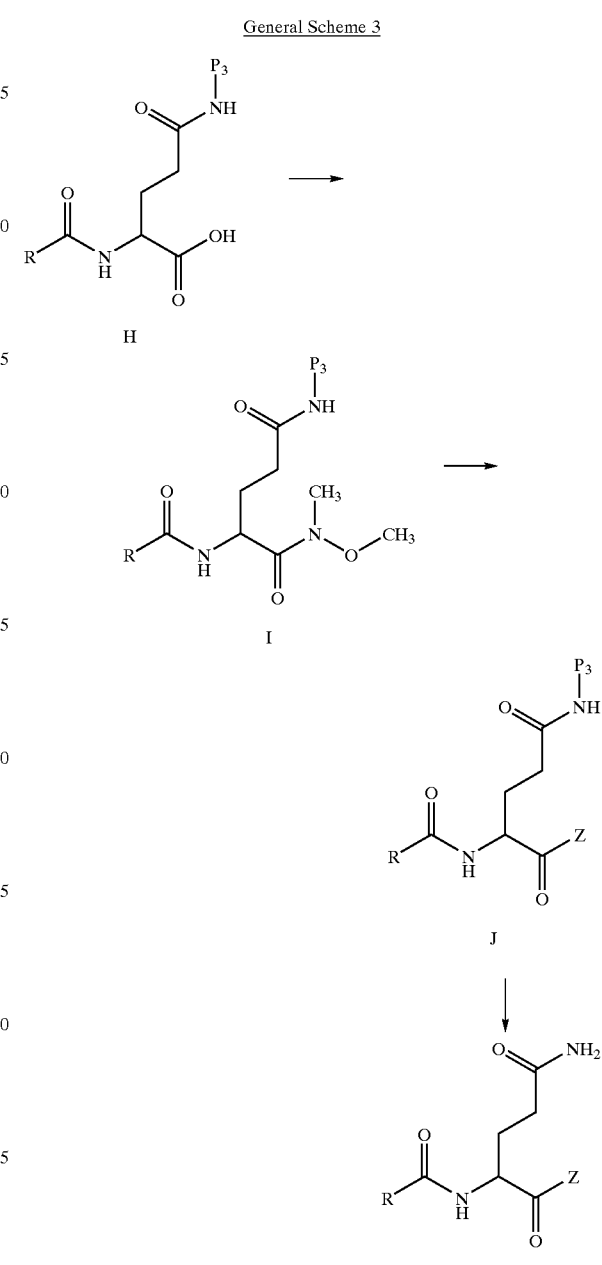

In this general process, an amino acid H (either commercially available or prepared by standard peptide coupling conditions and/or methods known in the art), where $P_3$ is an appropriate protecting group for the amide nitrogen (e.g., Tr) and R is any suitable organic moiety (e.g., Cbz-L-Leu-L-Phe-), is transformed into Weinreb amide I. Compound I is treated with an excess of an organometallic reagent (e.g., an alkyllithium or Grignard reagent) to provide product J. If necessary, the $P_3$ protecting group present in J is then removed to afford product K.

General Scheme 4

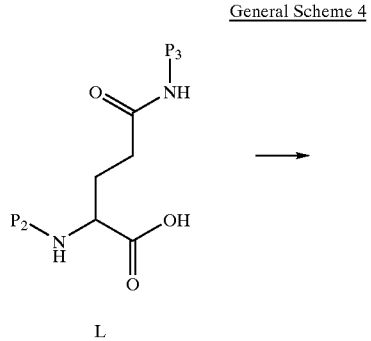

L

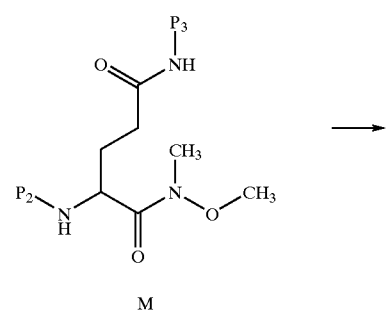

M

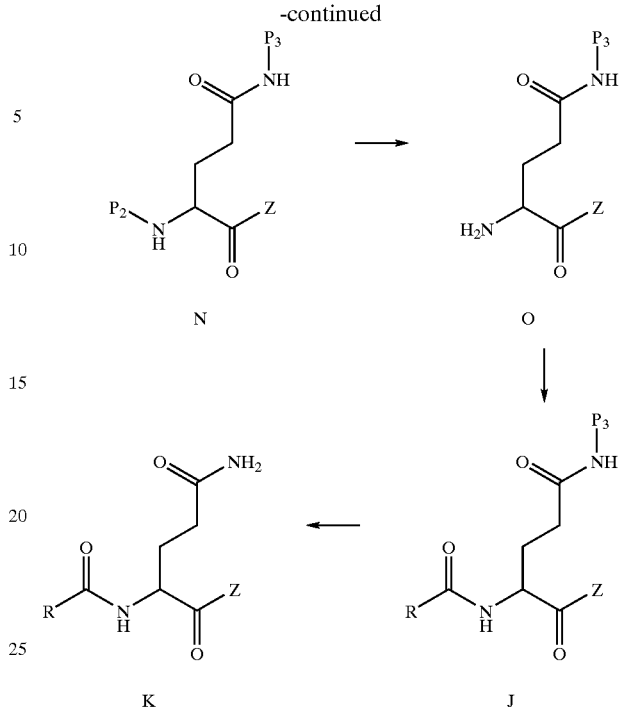

An alternate method of preparing products J and K is shown above. In this general method, amino acid L (either commercially available or prepared by a known method), where $P_3$ is an appropriate protecting group for the amide nitrogen (e.g., Tr) and $P_2$ is an appropriate orthogonal protecting group for nitrogen (e.g., Boc or Cbz), is transformed into Weinreb amide M. Compound M is treated with an excess of an organometallic reagent (e.g., an alkyllithium or Grignard reagent) to provide intermediate N. The $P_2$ protecting group present in N is then removed and the resulting amine O (or salt thereof) is derivatized (coupled) with a suitable organic moiety (e.g., Cbz-L-Leu-L-Phe-) to afford product J. As described above, the $P_3$ protecting group present in J is then removed to afford product K if necessary.

General Scheme 5

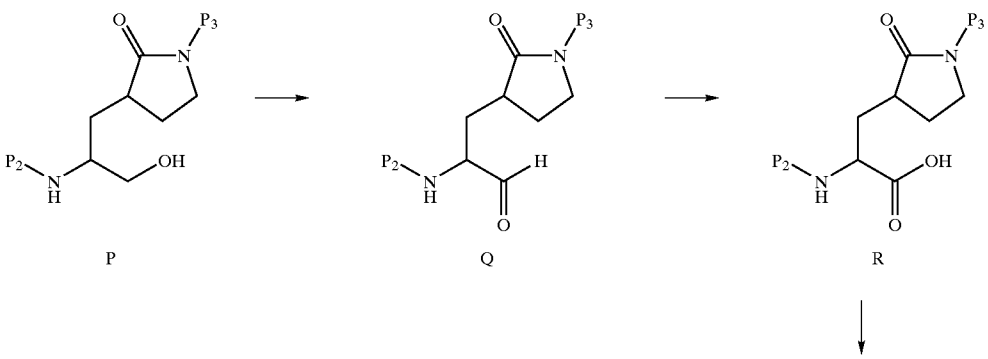

P          Q          R

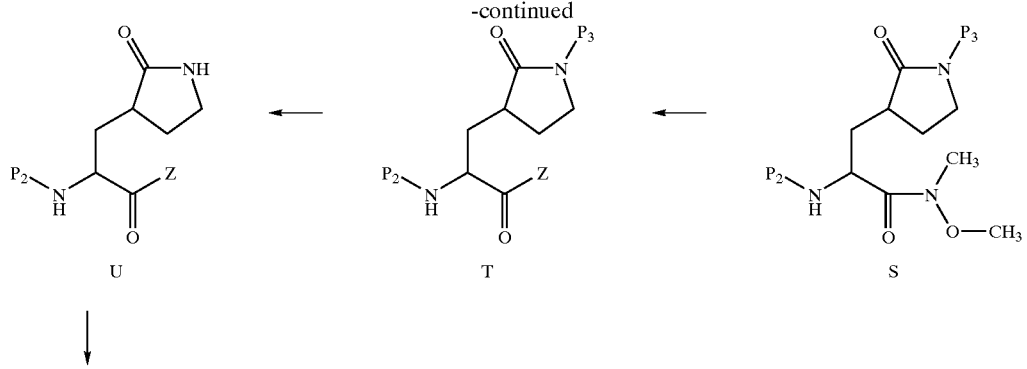

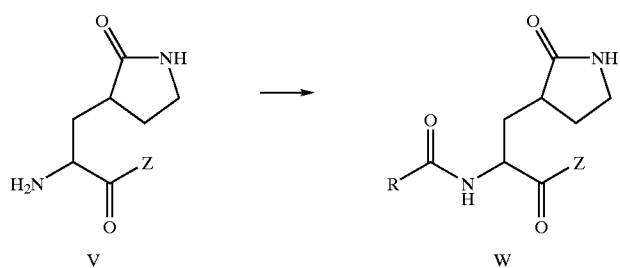

In this general method, amino alcohol P (prepared by known methods) where $P_3$ is an appropriate protecting group for the amide nitrogen (e.g., 2,4-dimethoxybenzyl) and $P_2$ is an appropriate orthogonal protecting group for nitrogen (e.g., Boc or Cbz) is oxidized to aldehyde Q. This intermediate is then further oxidized to carboxylic acid R, which is subsequently transformed into Weinreb amide S. Compound S is treated with an excess of an organometallic reagent (e.g., an alkyllithium or Grignard reagent) to provide intermediate T. The $P_3$ protecting group present in T is then removed and the resulting amide U is further deprotected (by removal of the $P_2$ protecting group) to afford amine (or salt thereof) V. Intermediate V is then derivatized (coupled) with a suitable organic moiety (e.g., Cbz-L-Leu-L-Phe-) to afford product W.

General Scheme 6

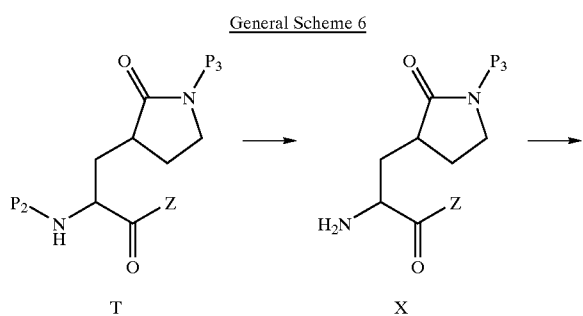

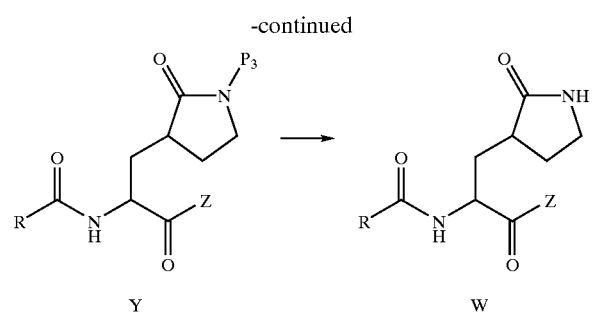

An alternate method of preparing product W is depicted above. In this general process, intermediate T (described above), where $P_3$ is an appropriate protecting group for the amide nitrogen (e.g., 2,4-dimethoxybenzyl) and $P_2$ is an appropriate orthogonal protecting group for nitrogen (e.g., Boc or Cbz), is deprotected by removal of the $P_2$ protecting group to give amine (or salt thereof) X. Compound X is then derivatized (coupled) with a suitable organic moiety (e.g., Cbz-L-Leu-L-Phe-) to afford intermediate Y. The $P_3$ protecting group present in Y is then removed to provide product W.

General Scheme 7

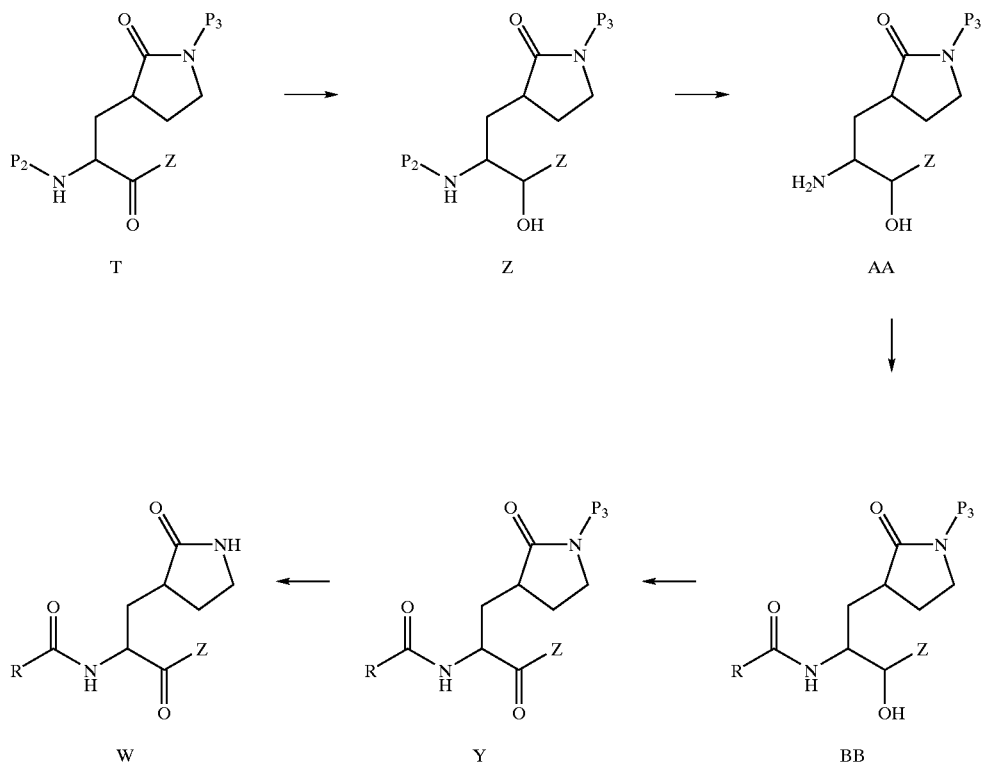

An additional alternate scheme for preparing product W is depicted above. Intermediate T (prepared above) where $P_3$ is an appropriate protecting group for the amide nitrogen (e.g., 2,4-dimethoxybenzyl) and $P_2$ is an appropriate orthogonal protecting group for nitrogen (e.g., Boc or Cbz) is reduced to alcohol Z. The $P_2$ protecting group present in Z is then removed and the resulting amine (or salt thereof) AA is derivatized (coupled) with a suitable organic moiety (e.g., Cbz-L-Leu-L-Phe-) to afford intermediate BB. At this point, BB may be further derivatized if necessary by removing any protecting groups present (other than $P_3$) and coupling any and/or all unprotected reactive functional groups (e.g., amines or alcohols) with suitable organic moieties to afford additional BB intermediates. When all appropriate derivatizations of BB have been completed, an oxidation is performed to give ketone V. The $P_3$ protecting group present in V is then removed to provide product W.

General Scheme 8

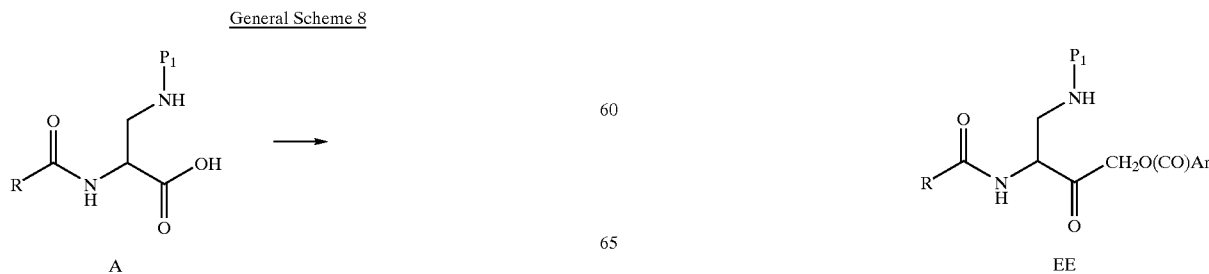

-continued

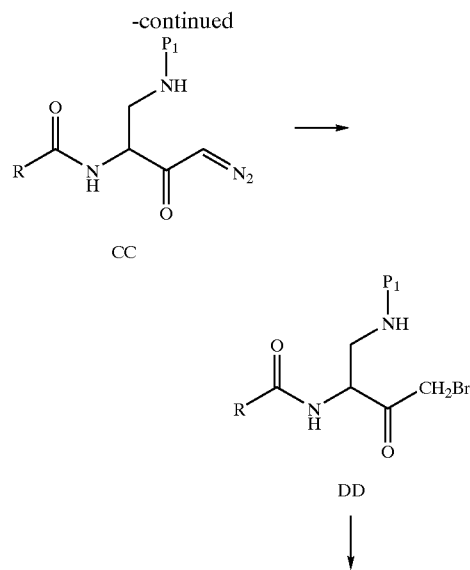

In this method, an amino acid A (prepared by standard peptide coupling conditions and/or methods), where $P_1$ is an appropriate protecting group for nitrogen (e.g., Boc or Ac) and R is any suitable organic moiety (e.g., Cbz-L-Leu-L-Phe-), is transformed into diazo compound CC. Compound CC, in turn, is converted to the bromide DD. This intermediate is subjected to a displacement reaction employing a carboxylic acid moiety to afford product EE. At this point, the $P_1$ nitrogen protecting group present in EE may be exchanged for an alternate if necessary (e.g., Boc exchanged for Ac).

where $P_3$ is an appropriate protecting group for the amide nitrogen (e.g., Tr) and $P_2$ is an appropriate orthogonal protecting group for nitrogen (e.g., Boc or Cbz), is transformed into diazo compound FF. Compound FF, in turn, is converted to the chloride GG. This intermediate is subjected to a displacement reaction employing a carboxylic acid moiety to afford intermediate HH. The $P_2$ protecting group present in HH is then removed and the resulting amine (or salt thereof) II is derivatized (coupled) with a suitable organic moiety (e.g., Cbz-L-Leu-L-Phe-) to afford intermediate JJ. The $P_3$ protecting group present in JJ is then removed to provide product KK.

General Scheme 9

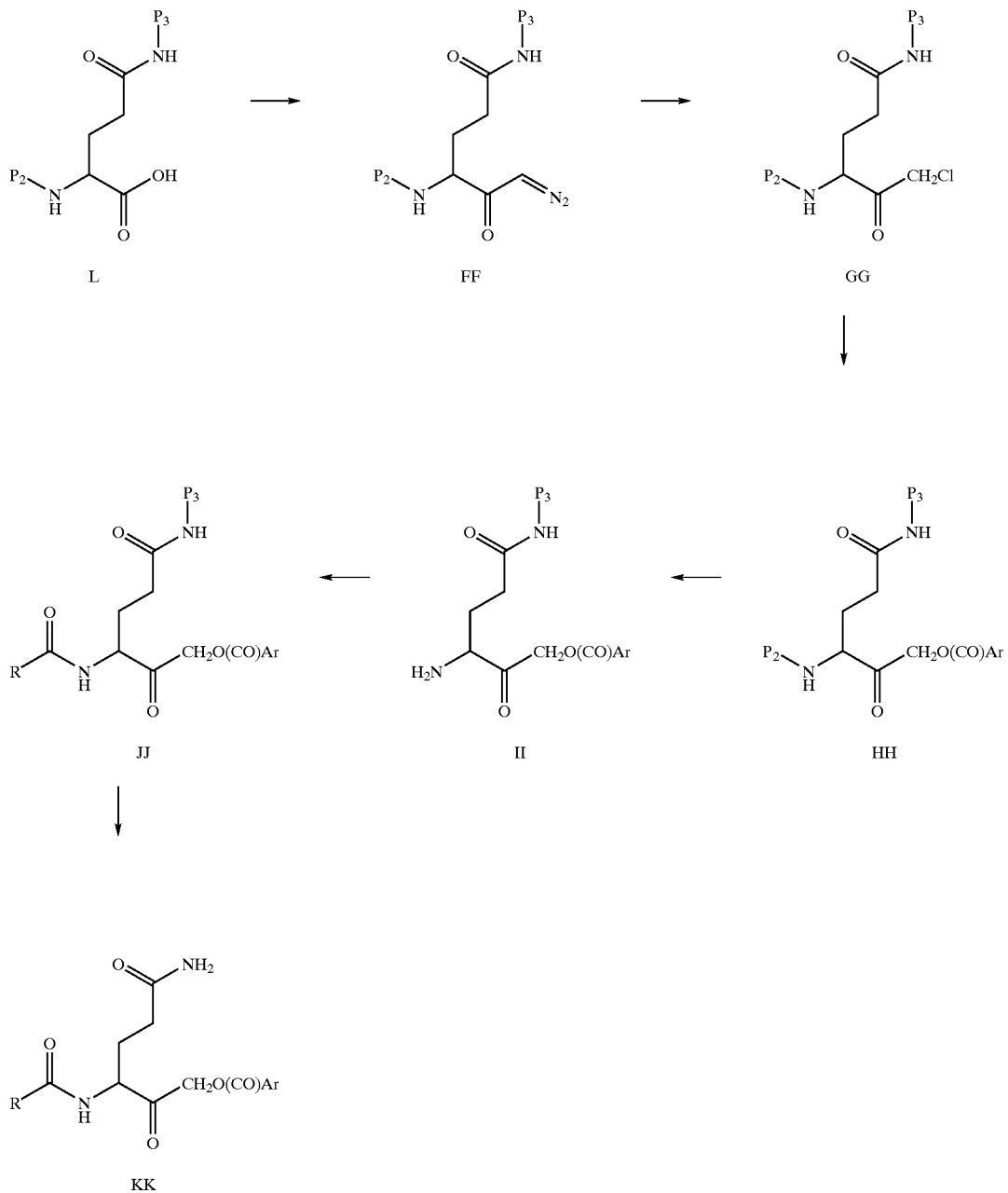

In the above-illustrated method, an amino acid L (either commercially available or prepared by known methods), To illustrate, the specific syntheses of the compounds of Examples 21 and 28 are summarized below.

27 28
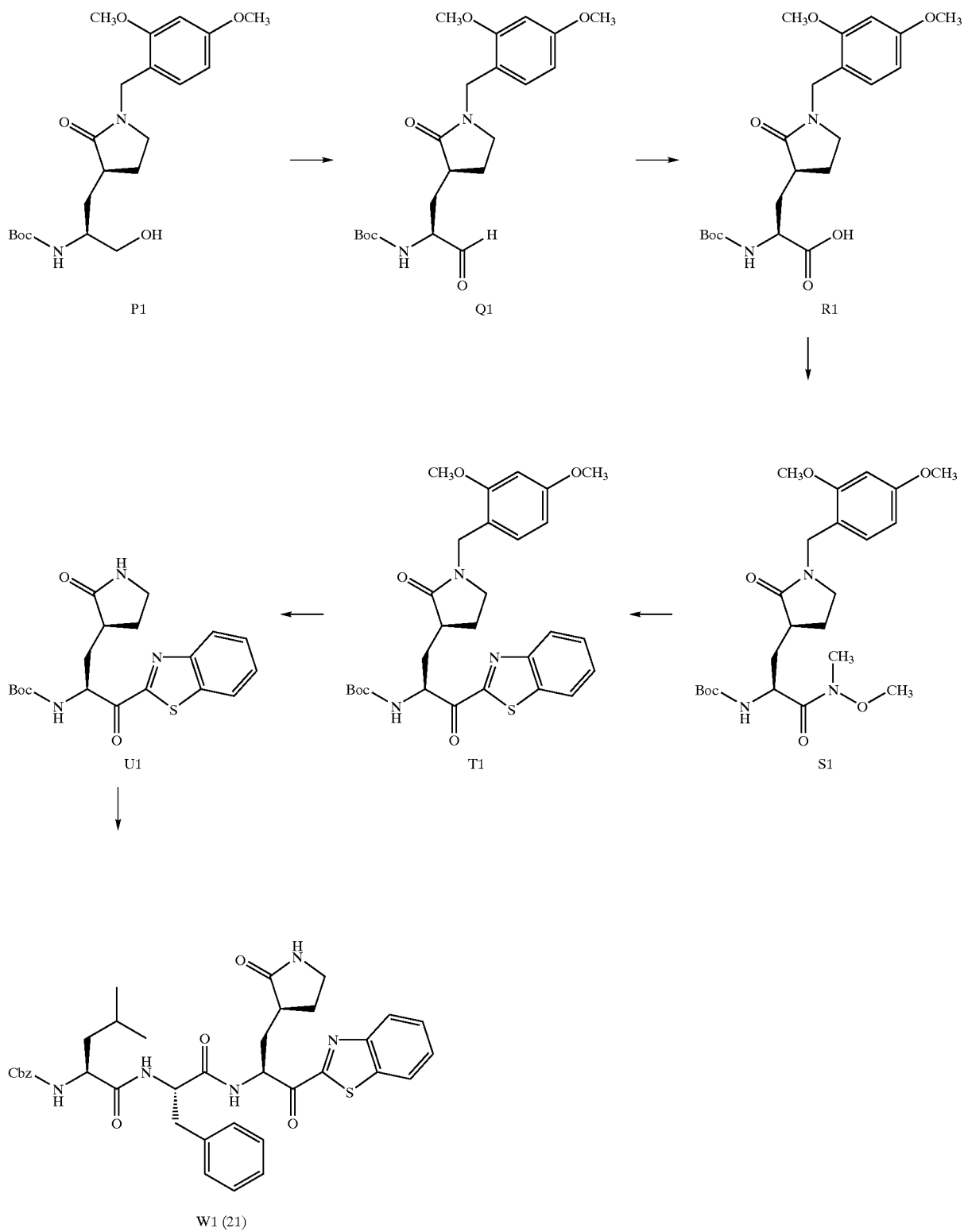

To prepare W1 (compound 21), alcohol P1 (prepared as described in Dragovich et al., *J. Med. Chem.* (1999), vol. 42, 1213) is oxidized to give aldehyde Q1 which, in turn, is transformed into carboxylic acid R1. This intermediate may be converted without purification to Weinreb amide S1. Exposure of S1 to an excess of 2-lithiobenzothiazole (generated from nBuLi and benzothiazole) provides ketone T1. The 2,4-dimethoxybenzyl nitrogen protecting group is subsequently removed from T1 to give U1. The Boc protecting group present in U1 is removed under acidic conditions and the resulting amine salt (not shown) is coupled with commercially available Cbz-L-Leu-L-Phe-OH to afford W1 (compound 21).

The synthesis of specific compound W8 is as follows:

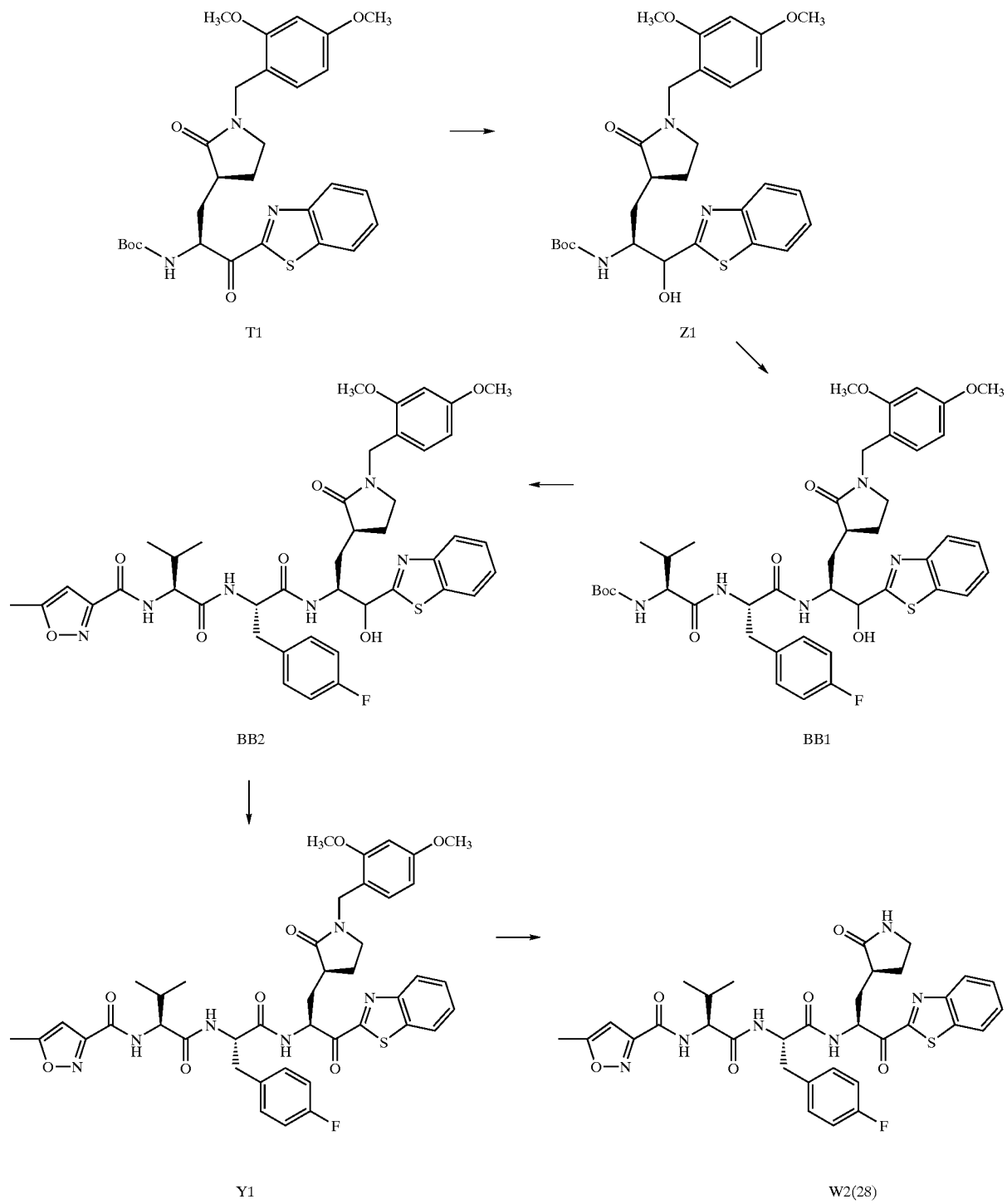

Ketone T1 (prepared as described above) is reduced to alcohol Z1 (isolated as a 1:1 mixture of diastereomers). The Boc protecting group present in Z1 is removed under acidic conditions and the resulting amine salt (not shown) is coupled with Boc-L-Val-L-Phe(4-F)-OH (prepared using standard peptide coupling techniques) to afford intermediate BB1 (isolated as a 1:1 mixture of diastereomers). The Boc protecting group present in BB1 is also removed under acidic conditions and the resulting amine salt (not shown) is derivatized with commercially available 5-methylisoxazole-3-carboxyl chloride to give intermediate BB2 (isolated as a 1:1 mixture of diastereomers). Oxidation of BB2 provides ketone Y1, and subsequent removal of the 2,4-dimethoxybenzyl nitrogen protecting group from Y1 affords W2 (compound 28).

Detailed procedures used to make compounds 21 and 28 and other exemplary compounds of formula I are set forth in the following illustrative examples.

EXAMPLES

The structures of the compounds of the following examples were confirmed by standard analytical techniques including one or more of the following: proton magnetic resonance spectroscopy, infrared spectroscopy, elemental microanalysis, and melting point.

Proton magnetic resonance ($^1$H NMR) spectra were determined using either a Varian UNITY plus 300 or a General Electric QE-300 spectrometer operating at a field strength of 300 megahertz (MHz). Chemical shifts are reported in parts per million (ppm, δ) downfield from an internal tetramethylsilane standard. Alternatively, $^1$H NMR spectra were referenced to residual protic solvent signals as follows: $CHCl_3$=7.26 ppm; DMSO=2.49 ppm; $C_6HD_5$=7.15 ppm. Peak multiplicities are designated as follows: s, singlet; d, doublet; dd, doublet of doublets; t, triplet; q, quartet; br, broad resonance; m, multiplet. Coupling constants are given in Hertz. Infrared absorption (IR) spectra were obtained using a Perkin-Elmer 1600 series FTIR spectrometer. Elemental microanalyses were performed by Atlantic Microlab Inc., Norcross, Ga. and gave results for the elements stated within ±0.4% of the theoretical values.

Flash column chromatography was performed using Silica gel 60 (Merck Art 9385). Analytical thin layer chromatography (TLC) was performed using precoated sheets of Silica 60 $F_{254}$ (Merck Art 5719). Melting points (mp) were determined on a Mel-Temp apparatus and are uncorrected.

All reactions were performed in septum-sealed flasks under a slight positive pressure of argon unless otherwise noted. All commercial reagents were used as received from their respective suppliers with the following exceptions: tetrahydrofuran (THF) was distilled from sodium-benzophenone ketyl prior to use; dichloromethane ($CH_2Cl_2$) was distilled from calcium hydride prior to use. $Et_2O$ refers to diethyl ether. DMF refers to N,N-dimethylformamide. DMSO refers to dimethylsulfoxide. MTBE refers to tert-butyl methyl ether. Other abbreviations include: $CH_3OH$ (methanol), EtOH (ethanol), EtOAc (ethyl acetate), DME (ethylene glycol dimethyl ether), Ac (acetyl), Me (methyl), Ph (phenyl), Tr (triphenylmethyl), Cbz (benzyloxycarbonyl), Boc (tert-butoxycarbonyl), TFA (trifluoroacetic acid), DIEA (N,N-diisopropylethylamine), TMEDA (N,N,N',N'-tetramethylethylenediamine), AcOH (acetic acid), $Ac_2O$ (acetic anhydride), NMM (4-methylmorpholine), HOBt (1-hydroxybenzotriazole hydrate), HATU [O-(7-azabenzotriazol-1-yl)-N,N,N',N'-tetramethyluronium hexafluorophosphate], EDC [1-(3-dimethylaminopropyl)-3-ethylcarbarbodiimide hydrochloride], DCC (dicyclohexyl-carbodiimide), DDQ (2,3-dichloro-5,6-dicyano-1,4-benzoquinone), DMAP (4-dimethylaminopyridine), Gln (glutamine), Leu (leucine), Phe (phenylalanine), Phe(4-F) (4-fluorophenylalanine), Val (valine), amino-Ala (2,3-diaminopropionic acid), and (S)-Pyrrol-Ala [(2S,3'S)-2-amino-3-(2'-oxopyrrolidin-3'-yl)-propionic acid]. Additionally, "L" represents naturally occurring amino acids.

A simplified naming system employing amino acid abbreviations is used to identify some intermediates and final products. When naming compounds, italicized amino acid abbreviations represent incorporation of a ketone moiety at the C-terminus of that residue [e.g., Boc-AA-$CH_3$=Boc-AA-C(O)—$CH_3$ (methyl ketone)].

Example 1

Cbz-L-Leu-L-Phe-L-(Tr-Gln)-$CH_2SCH_3$ (1)

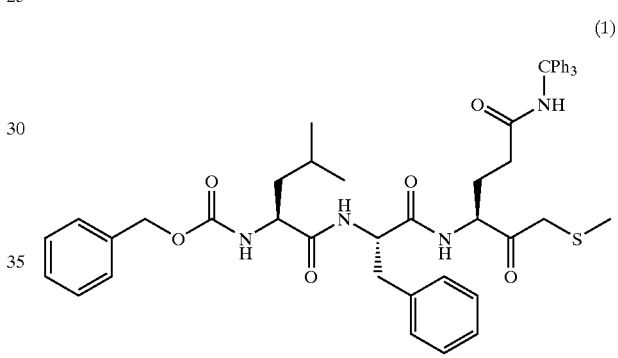

At 0° C. and under an argon atmosphere, TMEDA (0.81 mL, 5.37 mmol) and dimethyl sulfide (0.49 mL, 6.67 mmol) were added to nBuLi (1.58 M in hexane; 3.4 mL, 5.37 mmol). The mixture was stirred for 5 hours (h) while being brought to 23° C. The reaction mixture was cooled to −40° C. and a solution of Cbz-L-Leu-L-Phe-L-(Tr-Gln)-N(CH$_3$)O CH$_3$ (prepared as described in WIPO International Publication No. WO 97/43305) (0.85 g, 1.03 mmol) in 9 mL THF was added. Upon consumption of the starting material (as indicated by TLC) the mixture was quenched with 15 mL of 2 N AcOH at −40° C. and extracted with an excess of EtOAc. The pH of the aqueous phase was made basic with solid Na$_2$CO$_3$, and extracted with EtOAc. The organic layers were combined, washed sequentially with saturated NaHCO$_3$ and brine, dried over MgSO$_4$, filtered and concentrated under vacuum. The residue was subjected to column chromatography (45% EtOAc/hexane) to afford the product as a white solid in 60% yield. $^1$H NMR (CDCl$_3$) δ0.86 (m, 6H), 1.31 (m, 1H), 1.53 (m, 2H), 1.75 (m, 1H), 2.00 (s, 3H), 2.27 (m, 3H), 3.06 (m, 2H), 3.15 (m, 2H), 3.93 (m, 1H), 4.54 (m, 1H), 4.70 (m, 1H), 4.90 (m, 2H), 6.50 (m, 1H), 6.95 (d, 1H, J=7.0), 7.14–7.41 (m, 27H). HRMS calc for C$_{49}$H$_{54}$N$_4$O$_6$S (M+Cs), 959.2818; found, 959.2850. Anal. (C$_{49}$H$_{54}$N$_4$O$_6$S.0.50H$_2$O) C, H, N.

Example 2

Cbz-L-Leu-L-Phe-L-(Gln)-CH$_2$SCH$_3$

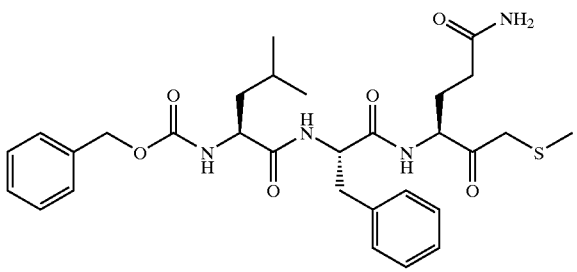
(2)

Cbz-L-Leu-L-Phe-L-(Tr-Gln)-CH$_2$SCH$_3$ (0.30 g, 0.363 mmol) was added to 10 mL of 1:1 CH$_2$Cl$_2$ and TFA at 0° C. and stirred for 45 minutes (min). The reaction mixture was concentrated under vacuum and taken up in excess EtOAc. This solution was washed twice with saturated NaHCO$_3$ and brine, dried over MgSO$_4$, filtered and concentrated under vacuum. The residue was triturated with Et$_2$O, giving 0.15 g (71% yield) of the product as a white solid. $^1$H NMR (DMSO-d$_6$) δ0.80 (d, 3H, J=6.6), 0.83 (d, 3H, J=7.0), 1.33 (m, 3H), 1.47 (m, 1H), 1.72 (m, 1H), 1.98 (s, 3H), 2.05 (m, 2H), 2.83 (dd, 1H, J=14.0, 8.0), 3.05 (dd, 1H, J=14.0, 4.4), 3.27 (m, 2H), 3.98 (m, 1 H), 4.38 (m, 1H), 4.52 (m, 1H), 5.02 (m, 2H), 6.78 (s, 1H), 7.14–7.35 (m, 11H), 7.42 (d, 1H, J=7.7), 8.03 (d, 1H, J=7.7), 8.42 (d, 1H, J=7.4). HRMS calc for C$_{30}$H$_{40}$N$_4$O$_6$S (M+H), 585.2747; found, 585.2720. Anal. (C$_{30}$H$_{40}$N$_4$O$_6$S) C, H, N.

Example 3

Cbz-L-Leu-L-Phe-L-(N-Ac-amino-Ala)-CHOC(O)-(2,4,6-trimethylphenyl)

Preparation of Intermediate Cbz-L-Leu-L-Phe-L-(N-Ac-amino-Ala)-CHN$_2$

To a solution of Cbz-L-Leu-L-Phe-L-(N-Ac-amino-Ala)-OH (prepared as described in Example 9 below) (0.381 g, 0.71 mmol) in 8 mL of THF was added NEt$_3$ (0.072 g, 99 μL, 0.71 mmol). The mixture was cooled to −15° C. and isobutylchloroformate (0.097 g, 92 μL, 0.71 mmol) was added. After stirring for 10 min, the mixture was cooled to −35° C., and excess diazomethane in Et$_2$O (generated from Diazald) was carefully added. The stirred reaction mixture was gradually warmed to 23° C. over a period of 2 h, and AcOH was then added to quench any excess diazomethane. The quenched mixture was diluted with H$_2$O and extracted with an excess of EtOAc. The organic layer was washed with brine, dried over Na$_2$SO$_4$, filtered, and concentrated to give a mixture of diazoketone (26%) along with Cbz-L-Leu-L-Phe-L-(N-Ac-amino-Ala)-OCH$_3$ (13%) as determined by $^1$H NMR integration and MS [(M+H) 565 and 555].

Preparation of Intermediate Cbz-L-Leu-L-Phe-L-(N-Ac-amino-Ala)-CH$_2$Br

To a 0° C. suspension of crude Cbz-L-Leu-L-Phe-L-(N-Ac-amino-Ala)-CHN$_2$ (~0.095 g, ~0.17 mmol) in 10 mL of 1:1 benzene: CH$_2$Cl$_2$ was added 0.2 mL of 48% aqueous (aq) HBr. After 1 h of stirring, another 0.2 mL of 48% aq HBr was added. After an additional 2 h at 0° C., the reaction mixture was poured into H$_2$O and extracted with a large excess of CH$_2$Cl$_2$. The organic phase was washed with H$_2$O, dried over Na$_2$SO$_4$, filtered and concentrated. The residue was subjected to column chromatography using a gradient of 80 to 100% EtOAc/hexane and afforded 0.034 g (33%) of the α-bromomethylketone as a yellow solid. $^1$H NMR (CDCl$_3$) δ0.86 (d, 3H, J=6.3), 0.90 (d, 3H, J=6.3), 1.36 (m, 1H), 1.55 (m, 2H), 1.91 (s, 3H), 3.01 (dd, 1H, J=14.3, 8.5), 3.17 (dd, 1H, J=10.7, 5.9), 3.48 (dt, 1H, J=14.0, 4.6), 3.84 (m, 1H), 4.04 (m, 2H), 4.27 (dd, 1H, J=13.1, 9.0), 4.61 (m, 1H), 4.85 (m, 1H), 5.04 (m, 2H), 5.11 (m, 1H), 6.48 (m, 1H), 6.57 (d, 1H, J=7.0), 7.18 (d, 1H, J=7.7), 7.22–7.42 (m, 10H). HRMS calc for C$_{29}$H$_{37}$N$_4$O$_6$Br (M+H), 617.1975; found, 617.2001. Anal. (C$_{29}$H$_{37}$N$_4$O$_6$Br) C, H, N.

Preparation of Product Cbz-L-Leu-L-Phe-L-(N-Ac-amino-Ala)-CH$_2$OC(O)-(2,4,6-trimethylphenyl)

To a stirred solution of Cbz-L-Leu-L-Phe-L-(N-Ac-amino-Ala)-CH$_2$Br (0.21 g, 0.34 mmol) dissolved in 2 mL DMF was added KH (35 wt % dispersion in mineral oil; 0.173 g, 1.02 mmol). After 5 min at 23° C., 2,4,6-trimethylbenzoic acid (0.057 g, 0.347 mmol) was added, and the mixture was stirred for 1 h. The mixture was concentrated, taken up in an excess of EtOAc, and H$_2$O was added. The organic layer was washed sequentially with H$_2$O, saturated aq NaHCO$_3$, and brine, and then was dried over Na$_2$SO$_4$, filtered and concentrated. The residue was purified by column chromatography (70% EtOAc/hexane) affording 0.054 g (22%) of the product as a white solid. $^1$H NMR (CDCl$_3$) δ0.89 (t, 6H, J=6.3), 1.42 (m, 1H), 1.56 (m, 2H), 2.05 (s, 3H), 2.32 (s, 3H), 2.35 (s, 6H), 3.03 (dd, 1H, J=14.0, 8.1), 3.16 (m, 1H), 3.67 (m 2H), 4.14 (m, 1H), 4.59 (m, 1H), 4.65 (m, 1H), 4.86 (m, 2H), 5.06 (m, 2H), 5.23 (d, 1H, J=7.0), 6.49 (t, 1H, J=6.1), 6.71 (d, 1H, J=6.6), 6.86 (s, 2H), 7.18–7.34 (m, 11H), 7.65 (d, 1H, J 6.3). HRMS calc for C$_{39}$H$_{48}$N$_4$O$_8$ (M+Na), 723.3370; found, 723.3358. Anal. (C$_{39}$H$_{48}$N$_4$O$_8$·0.5 H$_2$O) C, H, N.

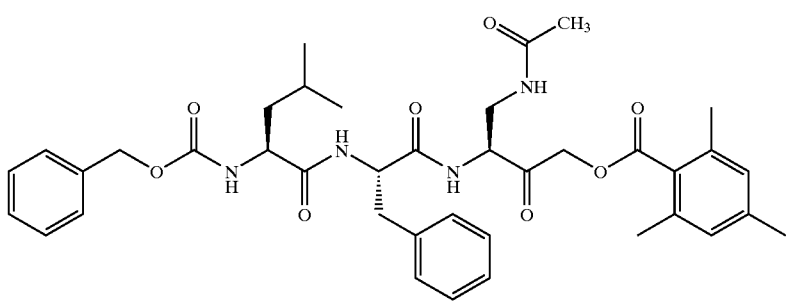
(3)

Example 4

Cbz-L-Leu-L-Phe-L-(N-Boc-amino-Ala)-CH₃

(4)

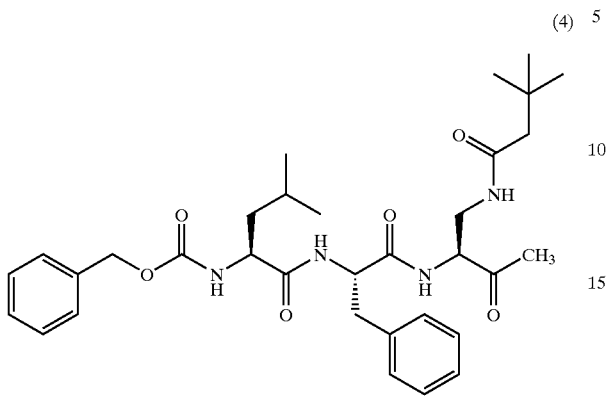

Following the procedure described below to prepare Cbz-L-Leu-L-Phe-L-(N-Boc-amino-Ala)-2-Benzthiazole (compound 6), the title compound was synthesized from Cbz-L-Leu-L-Phe-L-(N-Boc-amino-Ala)-N(CH₃)OCH₃ (prepared as described in Webber et al., *J. Med. Chem.* (1998), vol. 41, 2786) and 10 equiv. CH₃Li in 44% yield (75% based on recovered Weinreb amide) as a white solid. $^1$H NMR (CDCl₃) (rotameric mixture), δ0.88 (m, 6H), 1.38 (s, 9H), 1.43–1.63 (m, 3H), 2.20 (s, 3H), 3.05 (m, 2H), 3.26 (m, 1H), 3.46 (m, 1H), 3.58 (m, 1H), 4.16 (m, 1H), 4.47–4.59 (m, 1H), 4.62–4.75 (m, 1H), 5.06 (m, 2H), 5.10–5.20 (m, 1H), 5.37–5.50 (m, 1H), 6.86–6.96 (m, 1H), 7.22 (m, 5H), 7.34 (m, 5H). HRMS calc for C₃₂H₄₄N₄O₇ (M+Cs), 729.2264; found, 729.2231.

Example 5

Cbz-L-Leu-L-Phe-L-(N-Ac-amino-Ala)-CH₃

(5)

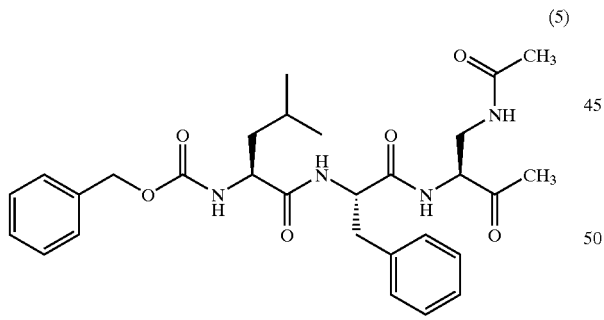

Following the procedure described below to prepare Cbz-L-Leu-L-Phe-L-(N-Ac-amino-Ala)-2-Pyridine (compound 8), the title compound was synthesized from Cbz-L-Leu-L-Phe-L-(N-Boc-amino-Ala)-CH₃ (compound 4) in 85% yield as a white solid. $^1$H NMR (CDCl₃) δ 0.88 (d, 3H, J=6.6), 0.90 (d, 3H, J=6.6), 1.38 (m, 1H), 1.53 (m, 2H), 1.90 (s, 3H), 2.24 (s, 3H), 3.04 (m, 1H), 3.17 (dd, 1H, J=13.6, 6.6), 3.50 (m, 1H), 3.76 (m, 1H), 4.11 (m, 1H), 4.47 (m, 1H), 4.63 (m, 1H), 5.07 (m, 2H), 5.23 and 5.30 (2d, 1H, J=5.9), 5.85 (m, 1H), 6.47 (m, 1H), 6.72 (t, 1H, J=6.1), 7.13–7.41 (m, 10H). HRMS calc for C₂₉H₃₈N₄O₆ (M+H), 539.2870; found, 539.2852. Anal. (C₂₉H₃₈N₄O₆·1.0H₂O)C, H, N.

Example 6

Cbz-L-Leu-L-Phe-L-(N-Boc-amino-Ala)-2-Benzthiazole (6)

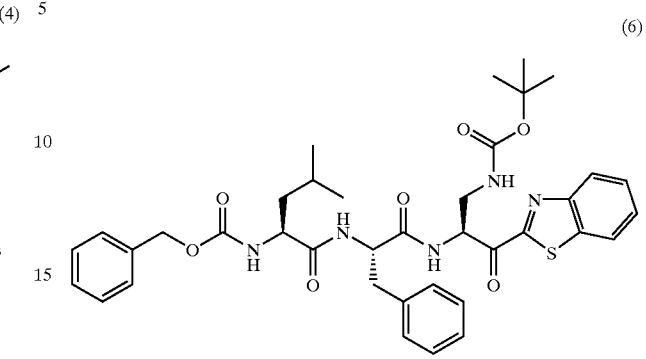

To a −78° C. solution of benzothiazole (0.226 g, 1.67 mmol) in 1.5 mL of THF was added nBuLi (0.67 mL, 2.5 M in hexane). The reaction mixture was stirred for 30 min at −78° C., then a solution of Cbz-L-Leu-L-Phe-L-(N-Boc-amino-Ala)-NCH₃OCH₃ (prepared as described in Webber et al., *J. Med. Chem.* (1998), vol. 41, 2786) (0.107 g, 0.17 mmol) in 1.5 mL of THF was added dropwise. The reaction mixture was stirred for 1 h at −78° C. and then gradually warmed to 23° C. When TLC indicated that most of the starting Weinreb amide was consumed, the reaction mixture was quenched with H₂O and extracted with EtOAc. The organic layers were combined, dried over Na₂SO₄, filtered and concentrated under vacuum. The residue was purified by column chromatography using a gradient solvent system (30, 50, 80% EtOAc/hexanes) providing a white solid in 16% yield (26% based on recovered starting material). $^1$H NMR (CDCl₃) (rotameric mixture) δ0.90 (t, 6H, J=5.9), 1.31 (s, 9H), 1.44 (m, 2H), 1.61 (m, 3H), 3.12 (m, 2H), 3.62–3.67 (m, 1H), 4.16 (m, 1H), 4.62–4.77 (m, 1H), 5.07–5.24 (m, 2H), 5.75–5.85 (m, 1H), 6.65–6.79 (m, 1H), 7.18 (m, 6H), 7.36 (m, 6H), 7.56 (m, 2H), 7.97 (t, 1H, J=8.1), 8.17 (d, 1H, J=7.0). HRMS calc for C₃₈H₄₅N₅O₇S (M+H), 716.3118; found, 716.3100. Anal. (C₃₈H₄₅N₅O₇S·1.5 H₂O) C, H, N.

Example 7

Cbz-L-Leu-L-Phe-L-(N-Boc-amino-Ala)-2-Pyridine (7)

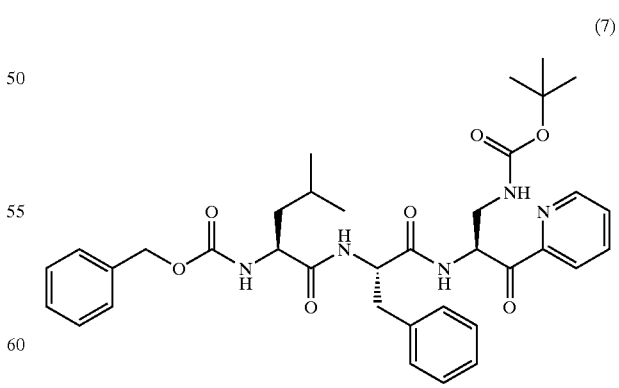

Using the procedure described above to prepare Cbz-L-Leu-L-Phe-L-(N-Boc-amino-Ala)-2-Benzthiazole (compound 6), the title compound was synthesized from Cbz-L-Leu-L-Phe-L-(N-Boc-amino-Ala)-NCH₃OCH₃ and 2-lithiopyridine (generated from 2-bromopyridine and nBuLi) in 83% yield. ¹H NMR (DMSO-d₆) δ0.79 (d, 3H, J=6.6), 0.82 (d, 3H, J=6.6), 1.26 (s, 9H), 1.35 (m, 2H), 1.47 (m, 1H), 2.81 (m, 1H), 3.01 (m, 1H), 3.39 (m, 2H), 3.58 (m, 1H), 3.98 (m, 1H ), 4.58 (m, 1H), 5.00 (s, 2H), 5.77 (m 1H), 6.78 (m, 1H), 7.19 (m, 5H), 7.33 (m, 5H), 7.41 (d, 1H, J=8.8), 7.68 (dd, 1H, J=6.4, 5.7), 7.91 (m, 1H), 8.01 (m, 1H), 8.24 (d, 1H, J=7.7), 8.74 (d, 1H, J=4.0). HRMS calc for $C_{36}H_{45}N_5O_7$ (M+H), 660.3397; found, 660.3384. Anal. ($C_{36}H_{45}N_5O_7 \cdot 0.5\ H_2O$) C, H, N.

Example 8

Cbz-L-Leu-L-Phe-L-(N-Ac-amino-Ala)-2-Pyridine (8)

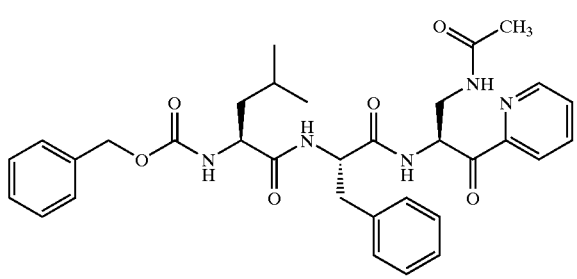

Cbz-L-Leu-L-Phe-L-(N-Boc-amino-Ala)-2-Pyridine (compound 7) (0.04 g, 60.6 μmol) was dissolved in 0.5 mL TFA. The solution was stirred at 0° C. for 30 min, and then was concentrated under vacuum. To the resulting TFA salt was added 1 mL of pyridine followed by 0.5 mL of $Ac_2O$ (excess). The mixture was stirred overnight at 23° C., concentrated under vacuum and subjected to column chromatography (1% $CH_3OH/CHCl_3$) to provide 0.023 g (63%) of a white solid. ¹H NMR (CDCl₃) δ0.89 (d, 3H, J=6.6), 0.91 (d, 3H, J=6.6), 1.41 (m, 1H), 1.58 (m, 2H), 1.87 (s, 3H), 3.08 (m, 2H), 3.59 (m, 1H), 3.95 (m, 1H), 4.12 (m, 1H), 4.64 (m, 1H), 5.08 (m, 3H), 5.89 (m, 1H), 6.51 (m, 1H), 6.63 (d, 1H, J=7.0), 7.19 (m, 5H), 7.35 (m, 5H), 7.49 (m, 1H), 7.85 (m, 1H), 8.01 (d, 1H, J=7.7), 8.67 (d, 1H, J=5.3). HRMS calc for $C_{33}H_{39}N_5O_6$ (M+H), 602.2979; found, 602.3002.

Example 9

Cbz-L-Leu-L-Phe-L-(N-Ac-amino-Ala)-2-Benzthiazole (9)

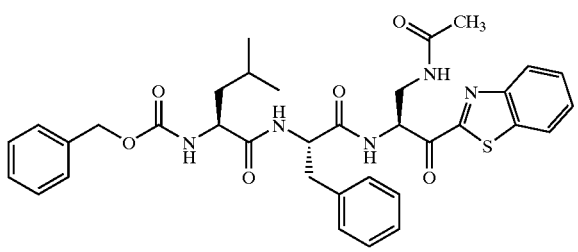

Preparation of Intermediate Cbz-L-(N-Ac-amino-Ala)-N(CH₃)OCH₃

To Cbz-L-(N-Ac-amino-Ala)-OH (prepared as described in Webber et al., *J. Med Chem.* (1998), vol. 41, 2786) (1.5 g, 5.36 mmol) dissolved in 30 mL $CH_2Cl_2$ was added EDC (1.08 g, 5.63 mmol), N,O-dimethylhydroxylamine hydrochloride (0.55 g, 5.64 mmol) and 4-methylmorpholine (1.35 g, 13.35 mmol). The reaction mixture was stirred overnight at 23° C., diluted with 250 mL of $CH_2Cl_2$, and washed with 50 mL of 1N HCl and 50 mL $H_2O$. The organic layer was dried over $Na_2SO_4$, filtered, and evaporated under vacuum. The residue was purified by column chromatography (5% $CH_3OH/CHCl_3$) to give 1.35 g (78%) of the amide product as a viscous oil. ¹H NMR (DMSO-d₆) δ1.76 (s, 3H), 3.08 (bs, 3H), 3.12 (m, 2H), 3.70 (s, 3H), 4.60 (bd, 1H, J=5.9), 5.01 (s, 2H), 7.34 (m, 5H), 7.43 (d, 1H, J=7.7), 7.90 (m, 1H). Anal. ($C_{15}H_{21}N_3O_5 \cdot 0.50H_2O$) C, H, N.

Preparation of Intermediate Cbz-L-Leu-L-Phe-L-(N-Ac-amino-Ala)-N(CH₃)OCH₃

To Cbz-L-(N-Ac-amino-Ala)-N(CH₃)OCH₃ (0.87 g, 2.69 mmol) dissolved in 20 mL of $CH_3OH$ was added 0.4 g of 10% Pd/C. The black suspension was stirred under an atmosphere of $H_2$ (balloon) at 23° C. for 2 h, then was filtered and concentrated to give 0.51 g of L-(N-Ac-amino-Ala)-N(CH₃)OCH₃ in quantitative yield as an oil. This material was used immediately without further purification.

The commercially available dipeptide Cbz-L-Leu-L-Phe-OH (1.0 g, 2.43 mmol) was dissolved in 25 mL of $CH_2Cl_2$ and 6-7 drops of DMF. N-hydroxysuccinimide (0.29 g, 2.52 mmol) was added followed by (upon homogeneity), DCC (0.526 g, 2.55 mmol). After approximately 2 h of stirring at 23° C., the mixture was filtered directly into a solution of L-(N-Ac-amino-Ala)-N(CH₃)OCH₃ (0.51 g, 2.70 mmol) in 10 mL $CH_2Cl_2$. The reaction mixture was stirred for 12 h at 23° C. and the solvents were removed under high vacuum. The residue was purified by column chromatography (5% of a saturated methanolic $NH_3$ solution in $CHCl_3$) to give 1.26 g (89%) of the tripeptide as a white solid. IR (KBr) 3300, 3067, 2955, 1657, 1537, 1262 cm.⁻¹. ¹H NMR (DMSO-d₆) δ0.79 (d, 3H, J=6.6), 0.82 (d, 3H, J=6.6), 1.31 (m, 2H), 1.47 (m, 1H), 1.77 (s, 3H), 2.79 (dd, 1H, J=13.6, 8.8), 3.00 (dd, 1H, J=14.0, 4.4), 3.10 (s, 3H), 3.27 (m, 2H), 3.67 (s, 3H), 3.96 (m, 1H), 4.51 (m, 1H), 4.91 (m, 1H), 5.01 (s, 2H), 7.17 (m, 5H), 7.33 (m, 5H), 7.43 (d, 1H, J=8.1), 7.82 (t, 1H, J=5.9), 7.87 (d, 1H, J=7.7), 8.19 (bd, 1H, J =7.7). Anal. ($C_{30}H_{41}N_5O_7 \cdot 0.50H_2O$) C, H, N.

Alternate Preparation of Intermediate Cbz-L-Leu-L-Phe-L-(N-Ac-amino-Ala)-N(CH₃)OCH₃

To a solution of Cbz-L-(N-Ac-amino-Ala)-OH (prepared as described in Webber et al., *J. Med. Chem.* (1998), vol. 41, 2786) (1.10 g, 4.62 mmol) in 20 mL of 3:6:1 $CH_3OH:AcOH:H_2O$ was added 1 g of 10% Pd/C. The mixture was stirred under an atmosphere of $H_2$ at 23° C. using a balloon for 3 h. Removal of the catalyst by filtration and concentration of the filtrate under vacuum gave the amino acid.AcOH salt in 99% yield. This material was used without further purification. ¹H NMR (CD₃OD) δ1.97 (s, 3H), 3.54 (dd, 1H, J=13.8, 6.1), 3.63–3.75 (m, 2H).

Commercially obtained Cbz-L-Leu-L-Phe-OH (1.9 g, 4.61 mmol) was dissolved in a mixture of 20 mL $CH_2Cl_2$ and 4 mL of DMF. To this stirred solution was added N-hydroxysuccinimide (0.53 g, 4.61 mmol). Once dissolved, DCC (0.951 g, 4.61 mmol) was added and the reaction was stirred at 23° C. for 3 h. At this time, the mixture was filtered directly into a solution of L-(N-Ac-amino-Ala)-ONa (prepared by dissolving L-(N-Ac-amino-Ala)-OH.AcOH (0.95 g, 4.61 mmol) in 1 mL of 1:1 DMF and adding 9.21 mL of 1 N aq NaOH at 0° C.). The reaction mixture was stirred for 2 h at 23° C. and the solvents were then removed under high vacuum. The residue was partitioned between 150 mL of 1 N HCl and 500 mL of EtOAc. Any solids formed were filtered and collected. The organic phase was then washed with $H_2O$, dried over $Na_2SO_4$, filtered, and concentrated. The solids were combined and purified by column chromatography (0.01% AcOH/5% CH$_3$OH/CHCl$_3$) yielding 68% of the tripeptide Cbz-L-Leu-L-Phe-L-(N-Ac-amino-Ala)-OH as a white solid. $^1$H NMR (CD$_3$OD) δ0.84 (d, 3H, J=6.6), 0.88 (d, 3H, J=6.6), 1.40 (m, 2H), 1.56 (m, 1H), 1.91 (s, 3H), 2.95 (dd, 1H, J=13.8, 9.7), 3.22 (dd, 1H, J=14.0, 4.8), 3.47 (dd, 1H, J=13.6, 7.7), 3.64 (dd, 1H, J=13.6, 4.0), 4.07 (dd, 1H, J=7.9, 5.0), 4.41 (m, 1H), 4.58 (m, 1H), 5.07 (m, 2H), 7.14–7.34 (m, 10H). HRMS calc for C$_{28}$H$_{36}$N$_4$O$_7$ (M+H), 541.2662; found, 541.2678.

To a solution of Cbz-L-Leu-L-Phe-L-(N-Ac-amino-Ala)-OH (0.64 g, 1.19 mmol) in 2 mL THF and 2 mL CH$_2$Cl$_2$ at −20° C. was added 1-methyl piperidine (0.12 g, 1.21 mmol) and isobutylchloroformate (0.163 g, 1.19 mmol). The mixture was stirred for 10 min, and a solution of N,O-dimethylhydroxylamine hydrochloride (0.116 g, 1.19 mmol) and 1-methyl piperidine (0.12 g, 1.21 mmol) in 3 mL CH$_2$Cl$_2$ were added dropwise. The reaction mixture was brought to 23° C. and stirred for an additional 3 h. The mixture was concentrated under vacuum, taken up in an excess of EtOAc, and washed with H$_2$O. The organic layer was dried over Na$_2$SO$_4$, filtered, and concentrated under vacuum. The residue was purified by column chromatography (5% CH$_3$OH/CHCl$_3$) yielding a white solid in 59% yield.

Preparation of Product Cbz-L-Leu-L-Phe-L-(N-Ac-amino-Ala)-2-Benzthiazole

This compound was prepared in 21% yield from benzothiazole and Cbz-L-Leu-L-Phe-L-(N-Ac-amino-Ala)-N(CH$_3$)OCH$_3$ as described above for the preparation of Cbz-L-Leu-L-Phe-L-(N-Boc-amino-Ala)-2-benzthiazole (compound 6). $^1$H NMR (CDCl$_3$) δ0.90 (m, 6H), 1.38 (s, 1H), 1.57 (m, 2H), 1.88 (s, 3H), 3.05–3.23 (m, 3H), 3.55–3.72 (m, 1H), 4.16 (m, 2H), 4.70 (m, 1H), 5.10 (m, 2H), 5.78–5.90 (m, 1H), 6.81 (m, 1H), 7.15 (m, 5H), 7.35 (m, 6H), 7.55 (m, 3H), 7.95 (t, 1H, J=8.0), 8.15 (d, 1H, J=7.0). HRMS calc for C$_{35}$H$_{39}$N$_5$O$_6$S (M+Na), 680.2519; found, 680.2549.

Example 10

Cbz-L-Leu-L-Phe-L-(N-Ac-amino-Ala)-C(O)NHCH$_3$ (10)

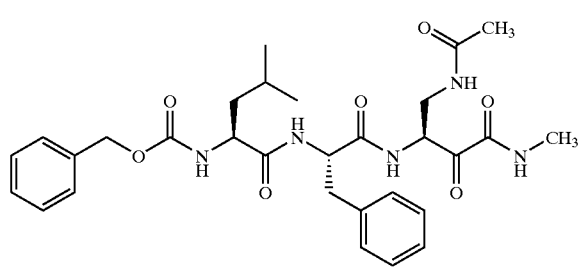

Preparation of Intermediate [1-(Acetylaminomethyl)-3-cyano-2-oxo-3-(triphenyl-λ$^5$-phosphanylidene) propyl] carbamic Acid Benzyl Ester This intermediate was prepared generally according to the method of Wasserman et al., *J. Org. Chem.* (1994), vol. 59, 4364. In particular, to a solution of (3-acetylamino-2-benzyloxycarbonylaminopropionic acid (1.40 g, 5.0 mmol, 1 equiv) in CH$_2$Cl$_2$ (50 mL) at 0° C. were added EDC (1.00 g, 5.25 mmol, 1.05 equiv) and DMAP (61 mg, 0.5 mmol, 0.1 equiv). A solution of (cyanomethylene) triphenylphosphorane (prepared as described in Freudenreich et al., *J. Am. Chem. Soc.* (1984), vol. 106, 3344) (2.50 g, 8.30 mmol, 1.66 equiv) in CH$_2$Cl$_2$ (16 mL) was added to the acid solution dropwise over 20 min. After stirring 2 h at 0° C., the reaction mixture was partitioned between deionized water (30 mL) and CH$_2$Cl$_2$ (3×50 mL). The combined organic layers were washed with brine (30 mL), dried over MgSO$_4$, filtered, and concentrated. The residue was purified by flash column chromatography (5% CH$_3$OH in CH$_2$Cl$_2$) to give [1-(acetylaminomethyl)-3-cyano-2-oxo-3-(triphenyl-λ$^5$-phosphanylidene)propyl]-carbamic acid benzyl ester (1.98 g, 70% yield) as a colorless foam. R$_f$=0.40 (10% CH$_3$OH in CH$_2$Cl$_2$). IR (cm$^{-1}$) 3312, 2175, 1716, 1437. $^1$H NMR (CDCl$_3$) δ1.91 (s, 3H), 3.66–3.79 (m, 2H), 5.04–5.06 (m, 1H), 5.10 (s, 2H), 5.94 (br s, 1H), 6.21 (br s, 1H), 7.26–7.70 (m, 21H).

Preparation of Intermediate [1-(Acetylaminomethyl)-2-methylcarbamoyl-2-oxoethyl]carbamic Acid Benzyl Ester A solution of [1-(acetylaminomethyl)-3-cyano-2-oxo-3-(triphenyl-λ$^5$-phosphanylidene) propyl]carbamic acid benzyl ester (569.9 mg, 1.01 mmol, 1 equiv) in CH$_2$Cl$_2$ (11 mL) at −78° C. was treated with ozone gas for 3 h. The chilled solution was then purged with Ar for 30 min until the color had changed from green to yellow. DIEA (0.211 mL, 1.21 mmol, 1.2 equiv) and methylamine hydrochloride (75.1 mg, 1.11 mmol, 1.1 equiv) were added. After 1.5 h at −78° C., a second portion of DIEA (0.25 mL, 1.43 mmol, 1.4 equiv) and methylamine hydrochloride (80.0 mg, 1.18 mmol, 1.17 equiv) were added, and stirring continued at −78° C. for 2.5 h longer. The volatiles were removed under reduced pressure, and the residue was purified by flash column chromatography (5% CH$_3$OH in CH$_2$Cl$_2$) to give [1-(acetylaminomethyl)-2-methylcarbamoyl-2-oxoethyl] carbamic acid benzyl ester (55.8 mg, 17% yield) as a pale yellow solid. R$_f$=0.23 (10% CH$_3$OH in CH$_2$Cl$_2$). IR (cm$^{-1}$) 3302, 1709, 1658, 1539. $^1$H NMR (CDCl$_3$) (rotameric mixture) δ1.89, 1.95 (2 s, 3H), 2.77 and 2.89 (2 d, 3H, J = 5.2), 3.47–3.54 (m, 1H), 3.61–3.69 (m, 1H), 4.29 (m, 1H), 5.10 (s, 2H), 6.64 (br s, 1H), 6.85 (br s, 1H), 7.06 (br s, 1H), 7.34 (s, 5H).

Preparation of Product Cbz-L-Leu-L-Phe-L-(N-Ac-amino-Ala)-C(O)NHCH$_3$

1 N HCl (solution in water) (0.17 mL, 1.0 equiv) was added to a solution of [1-(acetylaminomethyl)-2-methylcarbamoyl-2-oxoethyl]carbamic acid benzyl ester (55.8 mg, 0.17 mmol, 1 equiv) in absolute ethanol (5 mL). After purging with Ar, 5% palladium on carbon (42 mg) was added, and the mixture stirred under a hydrogen atmosphere for 5 h. After filtration to remove the catalyst and concentration of the filtrate, the residue was dissolved in DMF (2.0 mL) and added to a solution of commercially obtained Cbz-L-Leu-L-Phe-OH (70.1 mg, 0.17 mmol, 1.0 equiv), EDC (36 mg, 0.19 mmol, 1.1 equiv), HOBT (26 mg, 0.19 mmol, 1.1 equiv), and DIEA (66 mg, 0.51 mmol, 3.0 equiv) in DMF (1.5 mL). After stirring at 23° C. for 4 h, the volatiles were removed under reduced pressure. The residue was taken up into CH$_2$Cl$_2$ (20 mL), and washed sequentially with 1 N HCl (5 mL), saturated NaHCO$_3$ (5 mL), and brine (5 mL). The organic layer was dried over MgSO$_4$, filtered, and concentrated. The residue was purified by flash column chromatography (5% CH$_3$OH in CH$_2$Cl$_2$) to give Cbz-L-Leu-L-Phe-L-(N-Ac-amino-Ala)-C(O)NHCH$_3$ (34.6 mg, 35% yield) as a colorless, crystalline solid. R$_f$=0.19 (5% CH$_3$OH in CH$_2$Cl$_2$). IR (cm$^{-1}$) 3292, 1633, 1454, 1429. $^1$H NMR (CD$_3$OD) δ0.75–0.91 (m, 6H), 1.05–1.60 (4 m, 3H), 1.88, 1.91 (2s, 3H, rotamers), 2.70 (d, 3H, J=13.2), 2.85–3.13 (m, 3H), 3.55–3.61 (m, 1H), 3.97–4.09 (m, 2H), 4.38–4.62 (m, 3H), 5.48 (s, 2H), 7.15–7.35 (m, 10H).

Example 11

Cbz-L-Leu-L-Phe-L-(N-Ac-amino-Ala)-C(O)-Piperidine (11)

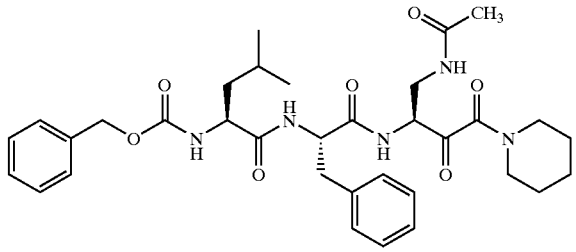

Preparation of Intermediate [1-(Acetylaminomethyl)-2,3-dioxo-3-piperidin-1-ylpropyl]carbamic Acid Benzyl Ester A solution of [1-(acetylaminomethyl)-3-cyano-2-oxo-3-(triphenyl-$\lambda^5$-phosphanylidene) propyl]carbamic acid benzyl ester (prepared as described in Example 10) (572 mg, 1.01 mmol, 1 equiv) in $CH_2Cl_2$ (11 mL) at −78° C. was treated with ozone gas for 2 h. The chilled solution was then purged with Ar for 10 min until the color had changed from green to yellow. Piperidine (0.110 mL, 1.12 mmol, 1.1 equiv) was added dropwise over 1 min, and stirring continued at −78° C. for 15 min. The volatiles were removed under reduced pressure, and the residue purified by flash column chromatography (5% $CH_3OH$ in $CH_2Cl_2$) to give [1-(acetylaminomethyl)-2,3-dioxo-3-piperidin-1-yl-propyl] carbamic acid benzyl ester (120.7 mg, 32% yield) as a colorless foam. $R_f$=0.30 (EtOAc). IR ($cm^{-1}$) 3304, 1720, 1639, 1537. $^1$H NMR ($CDCl_3$) δ1.59 (br s, 7H), 1.97 (s, 3H), 3.22–3.91 (m, 7H), 4.54–4.58 (m, 1H), 5.09 (s, 2H), 6.28 (br s, 1H), 6.67 (br s, 1H), 7.34 (s, 5H).

Preparation of Product Cbz-L-Leu-L-Phe-L-(N-Ac-amino-Ala)-C(O)-Piperidine

By a method analogous to that used to prepare compound 10, [1-(acetylaminomethyl)-2,3-dioxo-3-piperidin-1-ylpropyl]carbamic acid benzyl ester (54.4 mg, 0.14 mmol, 1 equiv) was deprotected and coupled with Cbz-L-Leu-L-Phe-OH (59.4 mg, 0.14 mmol, 1.0 equiv). After chromatography (5% $CH_3OH$ in $CH_2Cl_2$), Cbz-L-Leu-L-Phe-L-(N-Ac-amino-Ala)-C(O)-piperidine (10.5 mg, 12% yield) was obtained as a colorless film. $R_f$=0.40 (5% $CH_3OH$ in $CH_2Cl_2$). IR ($cm^{-1}$) 3302, 1657, 1537. $^1$H NMR ($CDCl_3$) δ0.80–0.97 (m, 6H), 1.34–1.98 (m, 9H), 3.09–3.19 (m, 2H), 3.37–4.20 (m, 5H) (m, 3H), 5.05–5.22 (m, 2H), 5.95–6.58 (m, 3H), 7.12–7.46 (m, 10H). MS (FAB) 636 (MH+), 658 (MNa+).

Example 12

Cbz-L-Leu-L-Phe-D-(N-Ac-amino-Ala)-C(O)-Piperidine (12)

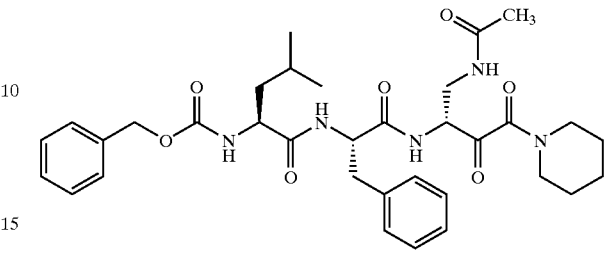

As a byproduct of the synthesis of compound 11, Cbz-L-Leu-L-Phe-D-(N-Ac-amino-Ala)-C(O)-piperidine (16.7 mg, 18% yield) was obtained as a colorless, crystalline solid. $R_f$=0.36 (5% $CH_3OH$ in $CH_2Cl_2$). IR ($cm^{-1}$) 3310, 1651, 1537. $^1$H NMR ($CDCl_3$) δ0.88 (br s, 6H), 1.39–1.82 (m, 8H), 1.93 (s, 3H), 2.99–3.02 (m, 1H), 3.15–3.22 (m, 1 H), 3.40–3.75 (m, 6H), 4.07–4.12 (m, 21H), 5.07–5.18 (m, 4H), 6.27–6.57 (2 m, 2H), 7.18–7.36 (m, 10H), 7.53–7.60 (m, 2H). MS (FAB) 636 (MH+)

Example 13

Cbz-L-Leu-L-Phe-L-(N-Ac-amino-Ala)-2-Thiazole (13)

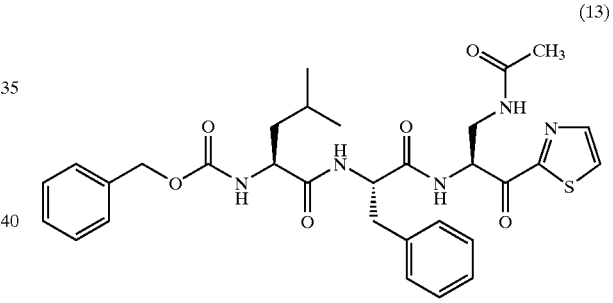

Preparation of Intermediate Cbz-L-(N-Ac-amino-Ala)-2-Thiazole

Using a slightly modified version of the method described above to prepare Cbz-L-Leu-L-Phe-L-(N-Boc-amino-Ala)-2-benzthiazole (compound 6), the reaction between Cbz-L-(N-Ac-amino-Ala)-N($CH_3$)$OCH_3$ (prepared as described in Example 9 above) and 5 equiv of the 2-thiazole anion (generated from thiazole and nBuLi) was performed. Once quenched with $H_2O$, the mixture was then acidified with 10% citric acid followed by extraction with EtOAc. Drying ($Na_2SO_4$), concentration, and purification of the residue by column chromatography using a gradient of 2–5% $CH_3OH$/$CHCl_3$ gave an 87% yield of the product as a white solid. $^1$H NMR ($CDCl_3$) δ1.88 (s, 3H), 3.88 (m, 2H), 5.12 (m, 2H), 5.55 (m, 1H), 6.11 (m, 1H), 6.23 (d, 1H, J=6.6), 7.36 (m, 5H), 7.75 (d, 1H, J=2.9), 8.05 (d, 1H, J=2.9). HRMS calc for $C_{16}H_{17}N_3O_4S$ (M+H), 348.1018; found, 348.1028.

Preparation of Product Cbz-L-Leu-L-Phe-L-(N-Ac-amino-A la)-2-Thiazole

To a solution of Cbz-L-(N-Ac-amino-Ala)-2-thiazole (0.225 g, 0.65 mmol) in 5 mL $CH_2Cl_2$ was added 5 mL 30% HBr/AcOH. The mixture was stirred for 1.5 h and was concentrated. The residue was washed thoroughly with $Et_2O$ and dried to give L-(N-Ac-amino-Ala)-2-thiazole-hydrobromide in quantitative yield. 1H NMR (CD$_3$OD) δ1.85 (s, 3H), 4.00 (m, 2H), 5.20 (m, 1H), 8.17 (m, 2H).

To a −20° C. solution of Cbz-L-Leu-L-Phe-OH (0.267 g, 0.65 mmol) in 5 mL THF was added Et$_3$N (0.197 g, 1.95 mmol) and isobutylchloroformate (89 mg, 0.65 mmol). After stirring for 10 min the reaction mixture was cooled to −40° C. and a DMF (2 mL) solution of L-(N-Ac-amino-Ala)-2-thiazole-hydrobromide was added. The reaction mixture was warmed to 23° C. and, after 1 h of stirring, was quenched with H$_2$O and extracted with CHCl$_3$. The organic layer was washed with brine, dried over Na$_2$SO$_4$, filtered, and concentrated. The residue was purified by column chromatography using a gradient of 2–5% CH$_3$OH/CHCl$_3$ to provide the product in 64% yield (2 steps) as a white solid. $^1$H NMR (CD$_3$OD) δ0.86 (d, 3H, J=6.3), 0.90 (d, 3H, J=6.3), 1.37 (m, 2H), 1.58 (m, 1H), 1.83 (s, 3H), 2.93 (m, 1H), 3.20 (m, 1H), 3.64 (m, 1H), 3.81 (m, 1H), 4.07 (m, 1H), 4.66 (m, 1H), 5.09 (m, 2H), 5.63 (m, 1H), 7.14 (m, 5H), 7.33 (m, 5H), 8.09 (d, 1H, J=2.9), 8.17 (d, 1H, J=2.6). HRMS calc for C$_{31}$H$_{37}$N$_5$O$_6$S (M+H), 608.2543; found, 608.2565. Anal. (C$_{31}$H$_{37}$N$_5$O$_6$S.0.5OH$_2$O) C, H, N.

Example 14

Cbz-L-Leu-L-Phe-L-(N-Ac-amino-Ala)-C≡CH

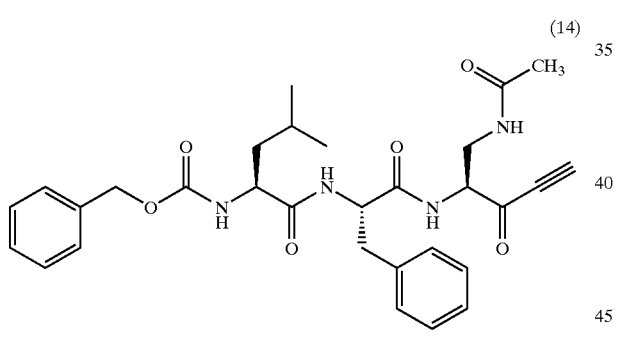

(14)

Under anhydrous conditions, 10 equiv of ethynyl magnesium bromide (0.5 M in THF, 12 mL) was added to a solution of Cbz-L-Leu-L-Phe-L-(N-Ac-amino-Ala)-N (CH$_3$)OCH$_3$ (prepared as described in Example 9) (0.35 g, 0.60 mmol) in 3 mL of THF. The reaction mixture was stirred for 1.5 h at 45° C. The mixture was then poured into 25 mL of 1 N HCl and extracted twice with 50 mL of EtOAc. The organic layers were washed with 25 mL of H$_2$O, dried over Na$_2$SO$_4$, filtered, and concentrated to leave a residue. Purification by column chromatography (EtOAc) gave a white solid in 67% yield. $^1$H NMR (DMSO-d$_6$) δ0.80 (t, 6H, J=7.7), 1.29 (m, 2H), 1.48 (m, 1H), 1.79 (s, 3H), 2.80 (m, 1H), 3.05 (dt, 1H, J=13.9, 4.1), 3.25 (m, 1H), 3.48 (m, 1H), 3.98 (m, 1H), 4.35 (m, 1H), 4.57 (m, 1H), 4.87 (d, 1H, J=7.7), 5.00 (s, 2H), 7.21 (m, 6H), 7.34 (m, 5H), 7.92 (m, 2H), 8.59 (t, 1H, J=7.9). HRMS calc for C$_{30}$H$_{36}$N$_4$O$_6$ (M+Cs), 681.1689; found, 681.1664.

Example 15

Cbz-L-Leu-L-Phe-L-(N-Ac-amino-Ala)-CH=CH$_2$

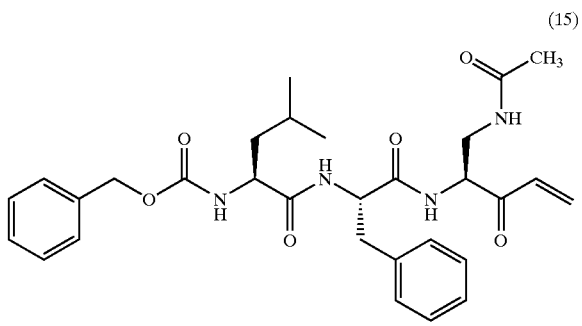

(15)

This compound was prepared in 22% yield from Cbz-L-Leu-L-Phe-L-(N-Ac-amino-Ala)-N (CH$_3$)OCH$_3$ (prepared as described in Example 9) and vinyl magnesium bromide using a procedure analogous to that described for generating Cbz-L-Leu-L-Phe-L-(N-Ac-amino-Ala)-C≡CH (compound 14). $^1$H NMR (DMSO-d$_6$) δ0.80 (t, 6H, J=7.5), 1.27 (m, 2H), 1.43 (m, 1H), 1.76 (s, 3H), 2.80 (m, 1H), 3.07 (m, 1H), 3.23 (m, 1H), 3.45 (m, 1H), 4.00 (m, 1H), 4.48 (m, 1H), 4.62 (m, 1H), 5.00 (s, 2H), 5.81 (d, 1H, J=11.4), 6.19–6.66 (m, 1H), 7.20 (m, 5H), 7.34 (m, 5H), 7.41 (d, 1H, J=8.5), 7.77 (m, 1H), 8.03 (d, 1H, J=7.0), 8.39 (d, 1H, J=7.4). Anal. (C$_{30}$H$_{38}$N$_4$O$_6$) C, H, N.

Example 16

Cbz-L-(N-Ac-amino-Ala)-L-Phe-L-(N-Ac-amino-Ala)-CH=CH$_2$

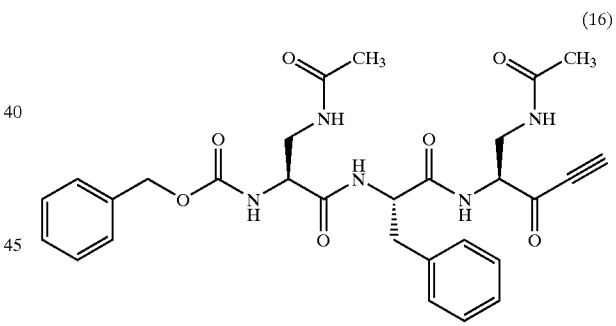

(16)

Preparation of Intermediate Cbz-L-(N-Ac-amino-Ala)-L-Phe-OH

Using the general procedure described for Cbz-L-Leu-L-Phe-L-(N-Ac-amino-Ala)-OH from Cbz-L-Leu-L-Phe-OH and L-(N-Ac-amino-Ala)-ONa in Example 9, Cbz-L-(N-Ac-amino-Ala)-L-Phe-OH was synthesized in 50% yield from Cbz-L-(N-Ac-amino-Ala)-OH (prepared as described in Webber et al., J. Med. Chem. (1998), vol. 41, 2786) and the sodium salt of L-phenylalanine as a white solid. $^1$H NMR (DMSO-d$_6$) δ1.77 (s, 3H), 2.90 (dd, 1H, J=13.8, 8.6), 3.05 (dd, 1H, J=13.6, 4.8), 3.20 (m, 2H), 4.09 (m, 1H), 4.38 (m, 1H), 5.00 (m, 2H), 7.19–7.34 (m, 11H), 7.88 (m, 1H), 8.07 (d, 1H, J=8.1).

Preparation of Intermediate Cbz-L-(N-Ac-amino-Ala)-L-Phe-L-(N-Ac-amino-Ala)-N (CH$_3$)OCH$_3$ Using the general procedure described in Example 9 for preparing Cbz-L-Leu-L-Phe-L-(N-Ac-amino-Ala)-N (CH$_3$)OCH$_3$ from Cbz-L-Leu-L-Phe-OH and L-(N-Ac-amino- Ala)-N (CH₃)OCH₃, Cbz-L-(N-Ac-amino-Ala)-L-Phe-L-(N-Ac-amino-Ala)-N(CH₃)OCH₃ was synthesized as a while solid in 81% yield from Cbz-L-(N-Ac-amino-Ala)-L-Phe-OH and L-(N-Ac-amino-Ala)-N(CH₃)OCH₃. ¹H NMR (DMSO-d₆) δ1.77 (s, 6H), 2.79 (dd, 1H, J=13.8, 9.4), 2.99 (dd, 1H, J=14.0, 6.6), 3.10 (s, 3H), 3.19 (m, 2H), 3.29 (m, 2H), 3.68 (s, 3H), 4.05 (m, 1H), 4.44 (m, 1H), 4.89 (m, 1H), 5.01 (m, 2H), 7.20 (m, 5H), 7.34 (m, 6H), 7.84 (m, 2H), 8.02 (d, 1H, J=7.7), 8.28 (m, 1H). Anal. (C₂₉H₃₈N₆O₈·1.0H₂O) C, H, N.

Preparation of Product

Using the procedure described for preparing compound 14, Cbz-L-(N-Ac-amino-Ala)-L-Phe-L-(N-Ac-amino-Ala)-CH=CH₂ was synthesized as a white solid in 25% yield from Cbz-L-(N-Ac-amino-Ala)-L-Phe-L-(N-Ac-amino-Ala)-N (CH₃)OCH₃ and ethynyl magnesium bromide. ¹H NMR (DMSO-d₆) δ1.76 (s, 3H), 1.79 (s, 3H), 2.79 (m, 1H), 3.05(m, 1H), 3.18 (m, 2H), 3.43 (m, 1H), 3.50 (m, 1H), 4.04 (m, 1H), 4.36 (m, 1H), 4.56 (m, 1H), 4.88 (d, 1H, J=4.0), 5.01 (m, 2H), 7.22 (m, 6H), 7.34 (m, 5H), 7.80 (m, 1H), 7.93 (m, 1H), 8.12 (t, 1H, J=8.6), 8.61 (t, 1H, J=8.1). HRMS calc for C₂₉H₃₃N₅O₇ (M+Cs), 696.1434; found, 696.1408.

Example 17

Cbz-L-Leu-L-Phe-L-(N-Ac-amino-Ala)-C≡CCH₂OCH₃

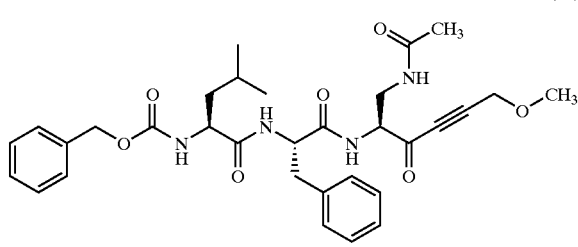

(17)

Using the procedure described for preparing compound 6, the title compound was synthesized in 19% yield from Cbz-L-Leu-L-Phe-L-(N-Ac-amino-Ala)-N(CH₃)OCH₃ (prepared as described in Example 9) and the lithium anion of methyl propargyl ether (generated from nBuLi and methyl propargyl ether at 23° C.). ¹H NMR (DMSO-d₆) δ0.80 (t, 6H, J=7.4), 1.28 (m, 2H), 1.47 (m, 1H), 1.79 (s, 3H), 2.80 (m, 1H), 3.05 (m, 1H), 3.27 (s, 3H), 3.33 (m, 1H), 3.50 (m, 1H), 4.00 (m, 1H), 4.32 (s, 2H), 4.36 (m, 1H). 4.57 (m, 1H), 5.01 (s, 2H), 7.22 (m, 6H), 7.34 (m, 5H), 7.96 (m, 2H), 8.58 (m, 1H). HRMS calc for C₃₂H₄₀N₄O₇ (M+Cs), 725.195 1; found, 725.1978.

Example 18

Cbz-L-Leu-L-Phe-L-(N-Ac-amino-Ala)-CH₂OCH₂CH₂Ph

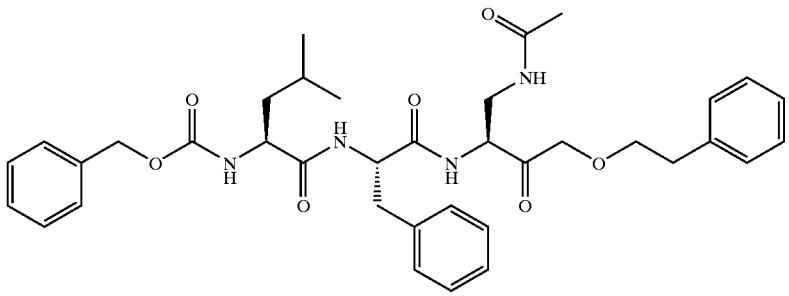

(18)

Preparation of Intermediate Bu₃SnCH₂OCH₂CH₂Ph

Potassium hydride (35 wt % in mineral oil, 2.29 g, 20.0 mmol, 2.0 equiv) was stirred in hexanes (10 mL) for 5 min, and then stirring was stopped and the solid allowed to settle. Most of the hexanes layer was removed by pipette, and the residual solvent removed under vacuum. The resulting dry KH powder was suspended in THF (20 mL) and phenethyl alcohol (1.22 g, 10.0 mmol, 1 equiv) was added (causing gas evolution). After stirring at 23° C. for 2.5 h, a thick precipitate formed. The mixture was cooled to 0° C. and a solution of iodomethyltributyltin (prepared according to Seitz, et al., *Synth. Commun.* (1983), vol. 13, 129) (6.46 g, 15.0 mmol, 1.5 equiv) in THF (15 mL) was added via cannula over 10 min. The mixture was warmed to 23° C. for 3.5 h, and then cooled to −78° C. The reaction was quenched with saturated aqueous NH₄Cl solution (25 mL), warmed to 23° C., and extracted with Et₂O (200 mL). The organic extracts were dried over MgSO₄, filtered, and concentrated. Purification of the residue by flash column chromatography (hexanes) afforded tributyl-phenethyloxymethyl-stannane (3.73 g, 88% yield) as a colorless liquid. R$_f$=0.63 (4% EtOAc in hexanes). IR (cm⁻¹) 2955, 2924, 2852, 1464, 1082. ¹H NMR (CDCl₃) δ0.90 (t, J=7.2, 15H), 1.31 (sextet, J=7.4, 6H), 1.50 (quintet, J=7.4, 6H), 2.86 (t, J=7.0, 2H), 3.54 (t, J=7.0, 2H), 3.75 (s, 2H), 7.15–7.33 (m, 5H). ¹³C NMR (CDCl₃) δ9.01, 13.66, 27.28, 29.12, 36.36, 61.94, 76.38, 125.94, 128.17, 128.91, 139.50.

Preparation of Product Cbz-L-Leu-L-Phe-L-(N-Ac-amino-Ala)-CH₂OCH₂CH₂Ph:

A solution of tributyl-phenethyloxymethyl-stannane (0.443 g, 1.02 mmol) in THF (10 mL) was cooled to −78° C. and nBuLi (2.5 M in hexane, 0.41 mL) was added. The mixture was stirred for 15 min and Cbz-L-Leu-L-Phe-L-(N-Ac-amino-Ala)-N (CH₃)OCH₃ (prepared as described in Example 9) (0.10 g, 0.17 mmol) was added. The reaction mixture was allowed to warm to 0° C. over a period of 1.5 h and then was poured into 100 mL EtOAc. This solution was washed with 30 mL of 10% aq citric acid, 30 mL H₂O, 3 mL brine, dried over MgSO₄, filtered and concentrated. The residue was purified by column chromatography (gradient elution, 3–5% CH₃OH/CHCl₃) yielding 0.014 g (13%) of a white solid. ¹H NMR (DMSO-d₆) δ0.79 (t, 6H, J=6.8), 1.30 (m, 2H), 1.48 (m, 1H), 1.76 (s, 3H), 2.80 (t, 2H, J=6.8), 2.86 (m, 1H), 2.99 (dd, 1H, J=13.2, 4.0), 3.24–3.42 (m, 2H), 3.56 (t, 2H, J=6.8), 4.01 (m, 1H), 4.10 (m, 2H), 4.34

(m, 1H), 4.47 (m, 1H), 5.00 (m, 2H), 7.13–7.33 (m, 10H), 7.40 (d, 1H, J=8.5), 7.72 (t, 1H, J=5.5), 8.03 (d, 1H, J=7.4), 8.32 (d, 1H, J=7.4). HRMS calc for $C_{37}H_{46}N_4O_7$ (M+Cs), 791.2421; found, 791.2439. Anal. ($C_{37}H_{46}N_4O_7$) C, H, N.

Example 19

Cbz-L-Leu-L-Phe-L-(N-Ac-amino-Ala)-CH$_2$OCH$_3$ (19)

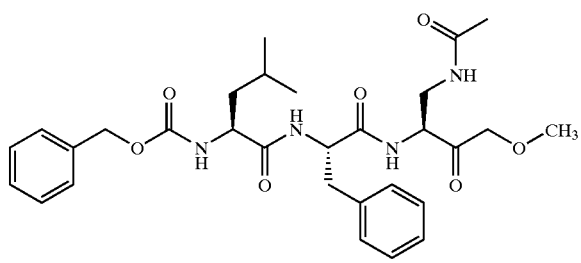

Using a procedure like that described for preparing compound 18, the title compound was synthesized as a white solid in 26% yield from Cbz-L-Leu-L-Phe-L-(N-Ac-amino-Ala)-N (CH$_3$)OCH$_3$ (prepared as described in Example 9) and tributyl-methoxymethyl-stannane (prepared as described in *C. R. Hebd. Seances Acad. Sci. Ser. C* (1970), vol. 270, 2080). $^1$H NMR (CDCl$_3$) δ0.90 (t, 6H, J=6.6), 1.45 (m, 1H), 1.62 (m, 1H), 2.01 (s, 3H), 3.17 (m, 1H), 3.25 (m, 1H), 3.48 (s, 3H), 3.88–4.05 (m, 1H), 4.12 (m, 1H), 4.20 (m, 1H), 4.34 (m, 1H), 4.82 (m, 1H), 4.85–4.95 (m, 1H), 5.05 (m, 1H), 5.10 (m, 2H), 5.83 (m, 1H), 6.45 (m, 1H), 6.55 (t, 1H, J=7.4), 7.05 (m, 1H), 7.40 (d, 1H, J=8.5), 7.18–7.43 (m, 10H). HRMS calc for $C_{30}H_{40}N_4O_7$ (M+H), 569.2975; found, 569.2991. Anal. ($C_{30}H_{40}N_4O_7$) C, H, N.

Example 20

Cbz-L-Leu-L-Phe-L-Gln-2-Benzthiazole (20)

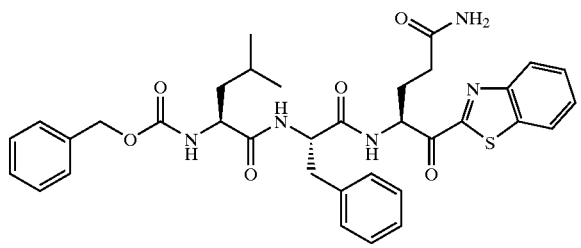

Preparation of Intermediate Boc-L-(Tr-Gln)-2-Benzthiazole:

To a solution of benzothiazole (1.63 mL, 14.9 mmol, 3.5 equiv) in THF (100 mL) at −78° C. was added nBuLi (9.31 mL, 14.9 mmol, 3.5 equiv). The mixture was stirred at −78° C. for 30 min. A solution of Boc-L-(Tr-Gln)-N(CH$_3$)OCH$_3$ (prepared as described in Dragovich et al., *J. Med. Chem.* (1998), vol. 41, 2806) (2.26 g, 4.25 mmol, 1 equiv) in THF (50 mL) was added to the above mixture at −78° C. After stirring 2 h at −78° C., the reaction mixture was partitioned between saturated NH$_4$Cl (100 mL) and EtOAc (2 ×100 mL). The combined organic layers were dried over Na$_2$SO$_4$ and were concentrated. Flash column chromatographic purification of the residue (25% EtOAc in hexane) gave Boc-L-(Tr-Gln)-2-benzthiazole (0.987 g, 35% yield) as a pale-yellow foam. R$_f$=0.24 (25% EtOAc in hexane). IR (cm$^{-1}$) 3394, 1696, 1489, 1165. $^1$H NMR (CDCl$_3$) δ1.46 (s, 9H), 1.59–1.64 (m, 1H), 2.07–2.09 (m, 1H), 2.44–2.53 (m, 2H), 5.61 (m, 1H), 7.08 (s, br. 1H), 7.25–7.33 (m, 16H), 7.55–7.63 (m, 2H), 8.00–8.03 (m, 1H), 8.16–8.19 (m, 1H). Anal. ($C_{36}H_{35}N_3O_4S$) C, H, N.

Preparation of Intermediate Cbz-L-Leu-L-Phe-L-(Tr-Gln)-2-Benzthiazole:

Boc-L-(Tr-Gln)-2-Benzthiazole (0.156 g, 0.26 mmol, 1.0 equiv) was dissolved in 1,4-dioxane (3 mL), and a solution of HCl in 1,4-dioxane (4.0 M, 3 mL) was added. The reaction was stirred at room temperature for 3 h, then the solvent was removed under reduced pressure. The residue was dissolved in DMF (5 mL), cooled to 0° C., and Cbz-L-Leu-L-Phe-OH (0.160 g, 0.39 mmol, 1.5 equiv), DIEA (0.136 mL, 0.78 mmol, 3 equiv) and HATU (0.148 g, 0.39 mmol, 1.5 equiv) were added sequentially. The reaction mixture was stirred at 0° C. for 40 min, and then the solvent was removed under reduced pressure. The residue was taken up into CH$_2$Cl$_2$ (50 mL), and washed sequentially with 0.5 N HCl (50 mL), saturated NaHCO$_3$ (50 mL), H$_2$O (50 mL), and brine (50 mL). The organic layer was dried over MgSO$_4$, filtered, and concentrated. The residue was purified by flash column chromatography (2% CH$_3$OH in CH$_2$Cl$_2$) to give Cbz-L-Leu-L-Phe-L-(Tr-Gln)-2-benzthiazole (0.170 g, 74% yield). R$_f$=0.24 (5% CH$_3$OH in CH$_2$Cl$_2$). IR (cm$^{-1}$) 3295, 1654, 1226. $^1$H NMR (CDCl$_3$) δ0.77–0.91 (m, 6H), 1.31–1.37 (m, 1H), 1.42–1.46 (m, 1H), 1.48–1.58 (m, 3H), 2.02–2.18 (m, 1H), 2.38–2.42 (m, 2H), 2.83–3.18 (m, 2H), 4.09–4.13 (m, 1H), 4.56–4.59 (m, 1H), 4.88–4.97 (m, 2H), 5.68–5.72 (m, 1H), 6.42–6.47 (m, 1H), 6.56 (d, 1H, J=7.5), 7.07–7.35 (m, 25H), 7.54–7.59 (m, 2H), 7.96–8.01 (m, 2H), 8.10–8.14 (m, 1H). Anal. ($C_{53}H_{53}N_5O_6S$) C, H, N.

Preparation of Product:

Triisopropylsilane (0.077 mL, 0.376 mmol) and trifluoroacetic acid (3 mL) were added sequentially to a solution of Cbz-L-Leu-L-Phe-L-(Tr-Gln)-2-benzthiazole (0.150 g, 0.17 mmol) in CH$_2$Cl$_2$ (3 mL) at 23° C., producing a bright-yellow solution. The reaction mixture was stirred at 23° C. for 30 min, during which time it became colorless. The volatiles were removed under reduced pressure, and the resulting solid was triturated with Et$_2$O (10 mL), filtered, and air-dried to give Cbz-L-Leu-L-Phe-L-Gln-2-benzthiazole (0.058 g, 49% yield) as a pale-yellow solid. R$_f$=0.50 (10% CH$_3$OH in CH$_2$Cl$_2$). mp=192–195° C. IR (cm$^{-1}$) 3298, 1659, 1526, 1238. $^1$H NMR (CDCl$_3$) δ0.68–0.81 (m, 6H), 1.22–1.30 (m, 2H), 1.42–1.48 (m, 1H), 1.98–2.07 (m, 1H), 2.15–2.24 (m, 3H), 2.68–2.79 (m, 1H), 3.00–3.05 (m, 1H), 3.93–3.95 (m, 1H), 4.60–4.64 (m, 1H), 4.99 (s, 2H), 5.42–6.46 (m, 1H), 6.81 (s, 1H), 7.15–7.37 (m, 13H), 7.63–7.71 (m, 2H), 7.87–7.90 (m, 1H), 8.26–8.29 (m, 1H), 8.70–8.72 (m, 1H). Anal. ($C_{35}H_{39}N_6O_5S$) C, H, N.

Example 21

Cbz-L-Leu-L-Phe-L-[(S)-Pyrrol-Ala]-2-Benzthiazole (21)

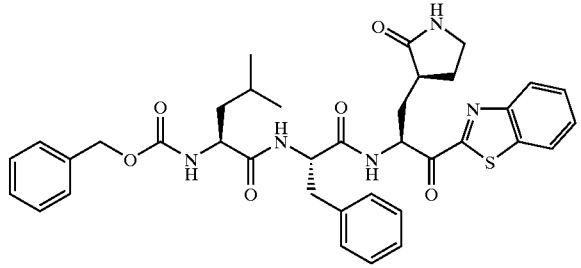

Preparation of Intermediate Boc-L-[(N-2,4-Dimethoxybenzyl)-(S)-Pyrrol-Ala]-H (Q1):

A solution of sulfur trioxide-pyridine complex (2.55 g, 16.0 mmol, 4 equiv) in DMSO (60 mL) was slowly added to a mixture of Boc-L-(N-2,4-dimethoxybenzyl)-(S)-Pyrrol-Alaninol (P1) (prepared as described in Dragovich et al., *J. Med. Chem.* (1999), vol. 42, 1213) (1.64 g, 4.00 mmol, 1 equiv) and $Et_3N$ (2.01 mL, 14.4 mmol, 3.6 equiv) cooled at 10–17° C. The reaction mixture was stirred at 23° C. for 1.5 h. The mixture was slowly quenched with $H_2O$ (80 mL) at 0° C., then extracted with EtOAc (2×150 mL). The combined organic layers were washed with 5% citric acid (200 mL) and brine (200 mL), and then were dried over $MgSO_4$ and concentrated. The resulting white foam was used without further purification.

Preparation of Intermediate Boc-L-[(N-2,4-Dimethoxybenzyl)-(S)-Pyrrol-Ala]-OH (R1):

To a solution of Boc-L-[(N-2,4-dimethoxybenzyl)-(S)-Pyrrol-Ala]-H (1.63 g, 4.00 mmol, 1 equiv) in t-butyl alcohol (50 mL) and 2-methyl-2-butene (12 mL) was added a solution of $NaClO_2$ (3.32 g, 36,68 mmol, 9.17 equiv) and $NaH_2PO_4$ (3.32 g, 27.68 mmol, 6.92 equiv) in $H_2O$ (20 mL) using an additional funnel. The mixture was stirred at 23° C. overnight. The mixture was washed with $Et_2O$ (80 mL), and the aqueous layer was acidified with 1 N HCl to pH 3, and then extracted with 10% $CH_3OH$ in $CH_2Cl_2$ (2×100 mL). The combined organic layers were washed with $H_2O$ (100 mL), dried over $Na_2SO_4$ and concentrated to give Boc-L-[(N-2,4-dimethoxybenzyl)-(S)-Pyrrol-Ala]-OH (1.11 g, 66%) as a white foam. This material was used without further purification. $^1$H NMR ($CDCl_3$) δ1.44 (s, 9H), 1.66–1.75 (m, 1H), 1.78–1.88 (m, 1H), 2.18–2.31 (m, 2H), 2.75–2.85 (m, 1H), 3.22–3.40 (m, 2H), 3.81 (s, 6H), 4.45 (s, 2H), 4.52–4.56 (m, 1H), 6.46–6.49 (m, 2H), 7.13 (d, 1H, J=7.5).

Preparation of Intermediate Boc-L-[(N-2,4-Dimethoxybenzyl)-(S)-Pyrrol-Ala]-N ($CH_3$)$OCH_3$ (S1):

Isobutyl chloroformate (0.340 mL, 2.62 mmol, 1 equiv) was added to a solution of Boc-L-[(N-2,4-dimethoxybenzyl)-(S)-Pyrrol-Ala]-OH (1.11 g, 2.62 mmol, 1 equiv) and NMM (0.570 mL, 5.24 mmol, 2 equiv) in $CH_2Cl_2$ (40 mL) at −20° C. The reaction mixture was stirred at −20° C. for 20 min, and then N,O-dimethylhydroxylamine hydrochloride (0.257 g, 2.62 mmol, 1 equiv) was added. The resulting mixture was stirred at −20° C. for 1 h and at 23° C. for 2 h, and then was partitioned between water (100 mL) and $CH_2Cl_2$ (2×100 mL). The combined organic layers were dried over $Na_2SO_4$ and concentrated. Flash column chromatographic purification of the residue (2% $CH_3OH$ in $CH_2Cl_2$) gave Boc-L-[(N-2,4-dimethoxybenzyl)-(S)-Pyrrol-Ala]-N ($CH_3$)$OCH_3$ (0.869 g, 71% yield) as a white foam. $R_f$=0.16 (5% $CH_3OH$ in $CH_2Cl_2$). IR ($cm^{-1}$) 3413, 1671, 1508, 1258. $^1$H NMR ($CDCl_3$) δ1.42 (s, 9H), 1.59–1.69 (m, 2H), 2.13–2.20 (m, 1H), 2.30–2.38 (m, 1H), 2.51–2.95 (m, 1H), 3.18–3.22 (m 5H), 3.77 (s, 3H), 3.80 (s, 6H), 4.41 (s, 2H), 4.64–4.69 (m, 1H), 5.39 (d, 1H, J=9.3), 6.42–6.44 (m, 2H), 7.11 (d, 1H, J=8.7). Anal. ($C_{23}H_{35}N_3O_7$.0.25$H_2O$) C, H, N.

Preparation of Intermediate Boc-L-[(N-2,4-Dimethoxybenzyl)-(S)-Pyrrol-Ala]-2-Benzthiazole (T1):

To a solution of benzothiazole (0.815 mL, 7.47 mmol, 3.5 equiv) in THF (80 mL) at −78° C. was added nBuLi (1.6 M in hexane, 4.7 mL, 7.47 mmol, 3.5 equiv). The mixture was stirred at −78° C. for 30 min. A solution of Boc-L-[(N-2,4-dimethoxybenzyl)-(S)-Pyrrol-Ala-]-N ($CH_3$)$OCH_3$ (0.869 g, 1.87 mmol, 1 equiv) in THF (30 mL) was added to the above mixture at −78° C. After stirring 2 h at −78° C., the reaction mixture was partitioned between saturated $NH_4Cl$ (100 mL) and EtOAc (2×50 mL). The combined organic layers were dried over $Na_2SO_4$ and were concentrated. Flash column chromatographic purification of the residue (2% $CH_3OH$ in $CH_2Cl_2$) gave Boc-L-[(N-2,4-dimethoxybenzyl)-(S)-Pyrrol-Ala]-2-benzthiazole (0.872 g, 86% yield) as a pale-yellow foam. $R_f$=0.43 (5% $CH_3OH$ in $CH_2Cl_2$). IR ($cm^{-1}$) 3402, 1698, 1503, 1258. $^1$H NMR ($CDCl_3$) δ1.42 (s, 9H), 1.89–1.96 (m, 1H), 2.17–2.23 (m, 1H), 2.43–2.48 (m, 1H), 2.71–2.74 (m, 1H), 3.20–3.28 (m, 3H), 3.78 (s, 6H), 4.40 (s, 2H), 5.55–5.60 (m, 1H), 5.93 (d, 1H, J=7.8), 6.39–6.44 (m, 2H), 7.09 (d, 1H, J=8.1), 7.52–7.60 (m, 2H), 7.97–8.00 (m, 1H), 8.15–8.17 (m, 1H). Anal. ($C_{28}H_{33}N_3O_6S$.0.20$H_2O$) C, H, N.

Preparation of Intermediate Boc-L-[(S)-Pyrrol-Ala]-2-Benzthiazole (U1):

To a suspension of Boc-L-[(N-2,4-dimethoxybenzyl)-(S)-Pyrrol-Ala]-2-benzthiazole (0.406 g, 0.75 mmol, 1 equiv.) in $CH_3CN$ (10 mL) and $H_2O$ (1 mL) was added DDQ (0.340 g, 1.5 mmol, 2 equiv). The reaction mixture was stirred at 60° C. for 5 h, and then was diluted with $CH_2Cl_2$ (50 mL) and washed sequentially with saturated $NaHCO_3$ (40 mL) and brine (40 mL). The organic layer was dried over $Na_2SO_4$ and was concentrated. The residue was purified by flash column chromatography (2% $CH_3OH$ in $CH_2Cl_2$) to give Boc-L-[(S)-Pyrrol-Ala]-2-benzthiazole (0.214 g, 80%) as a white foam. $R_f$=0.28 (10% $CH_3OH$ in $CH_2Cl_2$). IR ($cm^{-1}$) 3295, 1693, 1167. $^1$H NMR ($CDCl_3$) δ1.44 (s, 9H), 1.75 (s, 2H), 2.12–2.17 (m, 2H), 2.66–2.70 (m, 1H), 3.40–3.43 (m, 2H), 5.60 (m, 1H), 5.81 (m, 2H), 7.52–7.61 (m, 2H), 7.99 (d, 1H, J=8.4), 8.17 (d, 1H, J=7.8). Anal. ($C_{19}H_{23}N_3O_4S$) C, H, N.

Preparation of Product (W1):

Boc-L-[(S)-Pyrrol-Ala]-2-Benzthiazole (0.200 g, 0.56 mmol, 1.0 equiv) was dissolved in 1,4-dioxane (3 mL), and a solution of HCl in 1,4-dioxane (4.0 M, 3 mL) was added. The reaction was stirred at room temperature for 3 h, and then the solvent was removed under reduced pressure. The residue was dissolved in $CH_3CN$ (6 mL), cooled to 0° C., and Cbz-L-Leu-L-Phe-OH (0.347 g, 0.84 mmol, 1.5 equiv), NMM (0.246 mL, 2.24 mmol, 4 equiv) and HATU (0.319 g, 0.84 mmol, 1.5 equiv) were added sequentially. The reaction mixture was stirred at 0° C. for 40 min, and then the solvent was removed under reduced pressure. The residue was taken up into $CH_2C_2$ (50 mL) and was washed sequentially with 0.5 N HCl (50 mL), saturated $NaHCO_3$ (50 mL), $H_2O$ (50 mL), and brine (50 mL). The organic layer was dried over $MgSO_4$, filtered, and concentrated. The residue was purified by flash column chromatography (2% $CH_3OH$ in $CH_2Cl_2$) to give Cbz-L-Leu-L-Phe-L-[(S)-Pyrrol-Ala]-2-benzthiazole (0.142 g, 37% yield). $R_f$=0.20 (5% $CH_3OH$ in $CH_2Cl_2$). mp =108–111° C. IR ($cm^{-1}$) 3284, 1662, 1531, 1244. $^1H$ NMR ($CDCl_3$) δ0.81–0.88 (m, 6H), 1.40–1.44 (m, 1H), 1.55–1.59 (m, 2H), 1.89–2.00 (m, 2H), 2.10–2.17 (m, 2H), 2.48–2.52 (m, 2H), 3.09–3.18 (m, 2H), 3.35–3.37 (m, 2H), 4.11–4.19 (m, 1H), 4.80–4.85 (m, 1H), 5.05–5.10 (m, 2H), 5.25 (d, 1H, J=8.1), 5.68–5.70 (m, 1H), 6.18 (s, br 1H), 7.07–7.37 (m, 10H), 7.52–7.61 (m, 2H), 7.97–8.00 (m, 1H), 8.07–8.09 (m, 1H), 8.15–8.18 (m, 1H). Anal. ($C_{37}H_{41}N_5O_6S$) C, H, N.

Example 22

Cbz-L-Leu-L-Phe-L-[(S)-Pyrrol-Ala]-2-Thiazole (22)

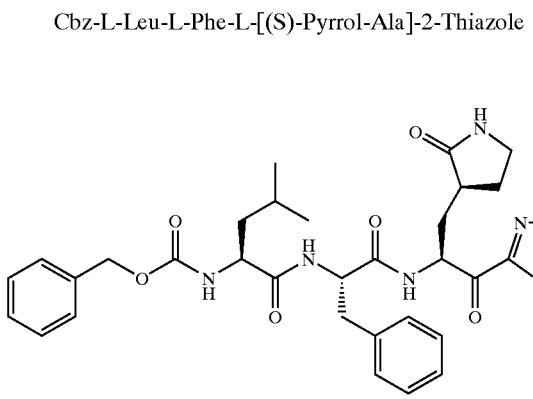

Boc-L-[(S)-Pyrrol-Ala]-2-Thiazole (prepared from Boc-L-[(N-2,4-dimethoxybenzyl)-(S)-Pyrrol-Ala]-N($CH_3$)$OCH_3$, nBuLi, and thiazole in a manner analogous to the ynthesis of Boc-L-[(S)-Pyrrol-Ala]-2-benzthiazole described in Example 21) (0.065 g, 0.19 mmol, 1.0 equiv) was dissolved in 1,4-dioxane (3 mL), and a solution of HCl in 1,4-dioxane (4.0 M, 3 mL) was added. The reaction mixture was stirred at 23° C. for 3 h, and then the solvent was removed under reduced pressure. The residue was dissolved in $CH_3CN$ (6 mL) cooled at 0° C., and then Cbz-L-Leu-L-Phe-OH (0.118 g, 0.29 mmol, 1.5 equiv), NMM (0.084 mL, 0.76 mmol, 4 equiv) and HATU (0.110 g, 0.29 mmol, 1.5 equiv) were added sequentially. The reaction mixture was stirred at 0° C. for 40 min, and then the solvent was removed under reduced pressure. The residue was taken up into $CH_2Cl_2$ (50 mL), and washed sequentially with 0.5 N HCl (50 mL), saturated $NaHCO_3$ (50 mL), $H_2O$ (50 mL), and brine (50 mL). The organic layer was dried over $MgSO_4$, filtered, and concentrated. The residue was purified by flash column chromatography (2% $CH_3OH$ in $CH_2Cl_2$) to give Cbz-L-Leu-L-Phe-L-[(S)-Pyrrol-Ala]-2-thiazole (0.057 g, 48% yield). $R_f$=0.48 (10% $CH_3OH$ in $CH_2Cl_2$). mp=83–85° C. IR ($cm^{-1}$) 3284, 1661, 1536, 1247. $^1H$ NMR ($CDCl_3$) δ0.85–0.86 (m, 6H), 1.39–1.44 (m, 1H), 1.52–1.58 (m, 2H), 2.00–2.07 (m, 4H), 2.43 (m, 2H), 3.01–3.21 (m, 3H), 3.32–3.34 (m, 2H), 4.14 (m, 1H), 4.85–4.87 (m, 1H), 5.08 (s, 2H), 5.29–5.32 (m, 1H), 5.59 (m, 1H), 6.55 (s, br 1H), 7.16–7.22 (m, 5H), 7.33 (s, 5H), 7.69 (d, 1H, J=1.5), 8.00 (d, 1H, J=1.5). Anal. ($C_{33}H_{39}N_5O_6S \cdot 0.50H_2O$) C, H, N.

Example 23
Cbz-L-Leu-L-Phe-L-[(S)-Pyrrol-Ala]-2-Pyridine (23)

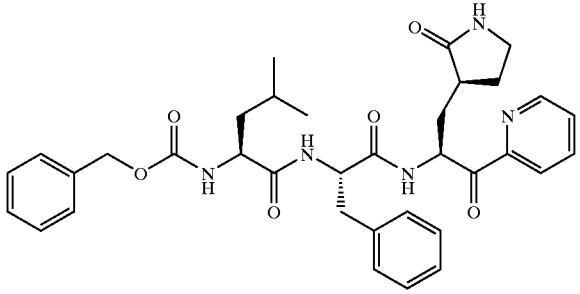

A solution of HCl in 1,4-dioxane (4.0 M, 1 mL) was added to Boc-L-[(S)-Pyrrol-Ala]-2-pyridine (prepared from Boc-L-[(N-2,4-dimethoxybenzyl)-(S)-Pyrrol-Ala]-N ($CH_3$) $OCH_3$, nBuLi, and pyridine in a manner analogous to the synthesis of Boc-L-[(S)-Pyrrol-Ala]-2-benzthiazole described in Example 21) (0.063 g, 0.19 mmol, 1 equiv) in 1 mL of 1,4-dioxane at 23° C. After 2 h, the volatiles were removed under reduced pressure. The residue and Cbz-L-Leu-L-Phe-OH (0.056 g, 0.23 mmol, 1.2 equiv) were dissolved in $CH_3CN$ (1 mL) and cooled at 0° C. NMM (0.083 mL, 0.91 mmol, 4.8 equiv) and HATU (0.060 g, 0.23 mmol, 1.2 equiv) were then added sequentially. The reaction mixture was stirred at 0° C. for 2 h, and then the volatiles were removed under reduced pressure. The residue was dissolved in $CH_2Cl_2$ (70 mL), and then washed with 1 N HCl (70 mL), $NaHCO_3$ (70 mL), and brine (70 mL). The combined organic layers were dried over $Na_2SO_4$, concentrated, and the residue was purified by flash column chromatography (gradient elution, 2→4% $CH_3OH$ in $CH_2Cl_2$) to afford Cbz-L-Leu-L-Phe-L-[(S)-Pyrrol-Ala]-2-pyridine (0.060 g, 50%) as white foam. $R_f$=0.28 (5% $CH_3OH$ in $CH_2Cl_2$). IR ($cm^{-1}$) 3279, 2954, 1690, 1660, 1531. $^1H$ NMR ($CDCl_3$) δ0.85–0.86 (m, 6H), 1.38–1.43 (m, 2H), 1.51–1.63 (m, 2H) 1.94–2.06 (m, 4H), 2.39–2.52 (m, 2H), 3.04–3.20 (m, 3H), 3.33–3.34 (m, 1H), 4.17–4.19 (m, 1H), 4.85–4.87 (m, 1H), 5.09–5.10 (m, 2H), 5.33–5.36 (m, 1H), 5.89 (m, 1H), 7.10–7.17 (m, 4H), 7.34 (m, 4H), 7.45–7.52 (m, 3H), 7.75–7.86 (m, 2H), 7.99 (d, 1H, J=7.8), 8.65 (d, 1H, J=4.2). Anal. ($C_{35}H_{41}N_5O_6 \cdot 0.35H_2O$) C, H, N.

Example 24
Cbz-L-Leu-L-Phe-L-[(S)-Pyrrol-Ala]-$CH_3$ (24)

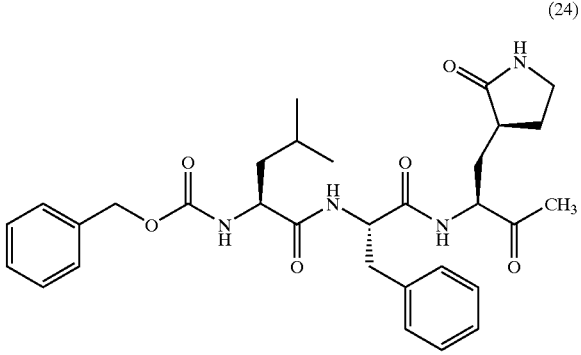

Preparation of Intermediate Boc-L-((N-2,4-Dimethoxybenzyl)-(S)-Pyrrol-Ala]-$CH_3$:

$CH_3Li$ (1.0 M in THF, 5.79 mL, 5.79 mmol, 3.5 equiv) was added to a solution of Boc-L-[(N-2,4-dimethoxybenzyl)-(S)-Pyrrol-Ala]-N($CH_3$)$OCH_3$ (prepared as described in Example 21) in THF (15 mL) at −40° C. The mixture was stirred at −40° C. for 1 h, and then was partitioned between saturated NH$_4$Cl (50 mL) and EtOAc (2×50 mL). The combined organic layers were dried over Na$_2$SO$_4$ and were concentrated. Flash column chromatographic purification of the residue (2% CH$_3$OH in CH$_2$Cl$_2$) gave Boc-L-[(N-2,4-dimethoxybenzyl)-(S)-Pyrrol-Ala]-CH$_3$ (0.366 g, 48% yield) as a pale-yellow foam. R$_f$=0.53 (50% EtOAc in hexane). IR (cm$^{-1}$) 3307, 1674, 1509, 1159. $^1$H NMR (CDCl$_3$) δ1.43 (s, 9H), 1.78–1.86 (m, 1H), 2.00–2.14 (m, 2H), 2.20–2.32 (m, 4H), 2.40–2.50 (m, 1H), 3.14–3.22 (m, 2H), 3.78 (s, 6H), 4.19–4.25 (m, 1H), 4.38 (s, 2H), 6.09 (d, 1H, J=6.6), 6.43–6.45 (m, 2H), 7.10 (d, 1H, J=7.8). Anal. (C$_{22}$H$_{32}$N$_2$O$_6$) C, H, N.

Preparation of Intermediate Cbz-L-Leu-L-Phe-L-[(N-2,4-Dimethoxybenzyl)-(S)-Pyrrol-Ala]-CH$_3$:

Boc-L-[(N-2,4-dimethoxybenzyl)-(S)-Pyrrol-Ala]-CH$_3$ (0.230 g, 0.55 mmol, 1.0 equiv) was dissolved in 1,4-dioxane (3 mL), and a solution of HCl in 1,4-dioxane (4.0 M, 3 mL) was added. The reaction was stirred at room temperature for 3 h, and then the solvent was removed under reduced pressure. The residue was dissolved in CH$_3$CN (6 mL), cooled to 0° C., and then Cbz-L-Leu-L-Phe-OH (0.340 g, 0.83 mmol, 1.5 equiv), NMM (0.242 mL, 2.20 mmol, 4 equiv) and HATU (0.314 g, 0.83 mmol, 1.5 equiv) were added sequentially. The reaction mixture was stirred at 0° C. for 40 min, and the solvent was removed under reduced pressure. The residue was taken up into CH$_2$Cl$_2$ (50 mL), and washed sequentially with 0.5 N HCl (50 mL), saturated NaHCO$_3$ (50 mL), H$_2$O (50 mL), and brine (50 mL). The organic layer was dried over MgSO$_4$, filtered, and concentrated. The residue was purified by flash column chromatography (gradient elution, 0→2% CH$_3$OH in CH$_2$Cl$_2$) to give Cbz-L-Leu-L-Phe-L-[(N-2,4-dimethoxybenzyl)-(S)-Pyrrol-Ala]-CH$_3$ (0.304 g, 77% yield) contaminated with some inseparable impurities. R$_f$=0.30 (50% EtOAc in hexane). IR (cm$^{-1}$) 3295, 1663, 1510, 1261. $^1$H NMR (CDCl$_3$) δ0.88 (s, 3H), 0.90 (s, 3H), 1.42–1.67 (m, 6H), 1.72–1.80 (m, 1H), 1.83–1.94 (m, 1H), 2.04–2.20 (m, 5H), 3.08–3.19 (m, 2H), 3.79 (s, 6H), 4.22–4.26 (m, 2H), 4.30–4.40 (m, 2H), 4.81–4.88 (m, 1H), 5.08–5.10 (m, 2H), 5.23 (m, 1H), 6.42–6.45 (m, 2H), 6.80 (d, 1H, J=8.1), 7.06–7.10 (m, 1H), 7.18–7.19 (m, 5H), 7.33–7.34 (m, 5H), 8.45 (m, 1H).

Preparation of Product:

To a suspension of Cbz-L-Leu-L-Phe-L-[(N-2,4-dimethoxybenzyl)-(S)-Pyrrol-Ala]-CH$_3$ (0.300 g, 0.42 mmol, 1 equiv) in CH$_3$CN (10 mL) and H$_2$O (1 mL) was added DDQ (0.190 g, 0.84 mmol, 2 equiv). The reaction mixture was stirred at 60° C. for 5 h, and then was diluted with CH$_2$Cl$_2$ (50 mL) and washed sequentially with saturated NaHCO$_3$ (40 mL) and brine (40 mL). The organic layer was dried over Na$_2$SO$_4$ and was concentrated. The residue was purified by flash column chromatography (2% CH$_3$OH in CH$_2$Cl$_2$) to give Cbz-L-Leu-L-Phe-L-[(S)-Pyrrol-Ala]-CH$_3$ (0.073 g, 27%) as a white foam. R$_f$=0.13 (5% CH$_3$OH in CH$_2$Cl$_2$). IR (cm$^{-1}$) 3285, 1661, 1544, 1261. $^1$H NMR (CDCl$_3$) δ0.82–0.90 (m, 6H), 1.24–1.37 (m, 3H), 1.55–1.64 (m, 2H), 1.74–1.96 (m, 4H), 2.09 (s, 3H), 2.35 (m, 1H), 3.10–3.12 (m, 1H), 3.28–3.32 (m, 1H), 4.09–4.16 (m, 1H), 4.35 (m, 1H), 4.79–4.84 (m, 1H), 5.02–5.14 (m, 2H), 5.22 (d, 1H, J=6.9), 5.99 (s, 1H), 6.94–6.96 (m, 1H), 7.20–7.24 (m, 5H), 7.35 (s, 5H), 7.94–7.96 (m, 1H). Anal. (C$_{31}$H$_{40}$N$_4$O$_6$·0.50H$_2$O) C, H, N.

Example 25

Cbz-L-Leu-L-Phe-L-[(S)-Pyrrol-Ala]-2-Benzothiophene

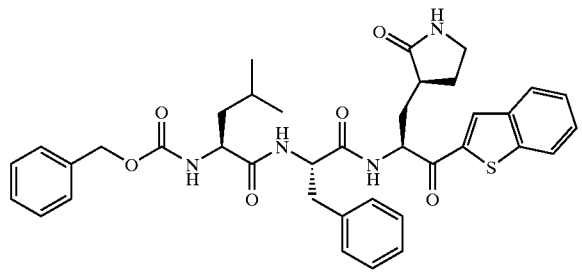

(25)

To a suspension of Cbz-L-Leu-L-Phe-L-[(N-2,4-dimethoxybenzyl)-(S)-Pyrrol-Ala]-2-benzothiophene (prepared from Boc-L-[(N-2,4-dimethoxybenzyl)-(S)-Pyrrol-Ala]-N (CH$_3$)OCH$_3$, nBuLi, and benzothiophene in a manner analogous to the synthesis of Cbz-L-Leu-L-Phe-L-[(N-2,4-dimethoxybenzyl)-(S)-Pyrrol-Ala]-CH$_3$ described in Example 24) (0.09 g, 0.12 mmol, 1 equiv) in CH$_3$CN (10 mL) and H$_2$O (1 mL) was added DDQ (0.066 g, 0.30 mmol, 2.4 equiv). The reaction mixture was stirred at 60° C. for 5 h, and then was diluted with CH$_2$Cl$_2$ (50 mL) and washed sequentially with saturated NaHCO$_3$ (40 mL) and brine (40 mL). The organic layer was dried over Na$_2$SO$_4$ and was concentrated. The residue was purified by flash column chromatography (2% CH$_3$OH in CH$_2$Cl$_2$) to give Cbz-L-Leu-L-Phe-L-[(S)-Pyrrol-Ala]-2-benzothiophene (0.055 g, 69%) as a white foam. R$_f$=0.52 (10% CH$_3$OH in CH$_2$Cl$_2$). IR (cm$^{-1}$) 3287, 1663, 1514, 1255. $^1$H NMR (CDCl$_3$) δ0.77–0.82 (m, 6H), 1.26–1.32 (m, 2H), 1.47–1.53 (m, 2H), 1.61–1.81 (m, 2H), 2.10–2.20 (m, 2H), 2.32–2.36 (m, 1H), 2.73–2.81 (m, 1H), 2.87–2.94 (m, 1H), 3.06–3.15 (m, 2H), 3.97–4.03 (m, 1H), 4.50–4.55 (m, 1H), 5.00 (m, 2H), 5.32–5.37 (m, 1H), 6.97–7.10 (m, 5H), 7.28–7.40 (m, 6H), 7.46–7.58 (m, 2H), 7.65 (s, 1H), 8.02–8.08 (m, 2H), 8.40 (s, 1H), 8.69 (d, 1H, J=8.1). Anal. (C$_{38}$H$_{42}$N$_4$O$_6$) C, H, N.

Example 26

Cbz-L-Leu-L-Phe-L-[(S)-Pyrrol-Ala]-Ph

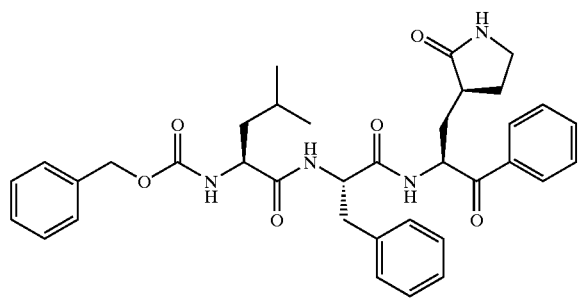

(26)

The title compound was prepared from Boc-L-[(N-2,4-dimethoxybenzyl)-(S)-Pyrrol-Ala]-N (CH$_3$)OCH$_3$ and PhLi in a manner analogous to the synthesis of Cbz-L-Leu-L-Phe-L-[N-2,4-dimethoxybenzyl)-(S)-Pyrrol-Ala]-CH$_3$ described in Example 24. R$_f$=0.25 (5% MeOH in CH$_2$Cl$_2$).

IR (cm$^{-1}$) 3280, 1696, 1643. $^1$H NMR (CDCl$_3$) δ0.79–0.92 (m, 7H), 1.34–1.44 (m, 1H), 1.48–1.89 (m, 5H), 2.06–2.18 (m, 1H), 2.27–2.38 (m, 1H), 2.44–2.56 (m, 1H), 2.98–3.35 (m, 3H), 4.11–4.21 (m, 1H), 4.76–4.85 (m, 1H), 5.06 (d, 1H, J=12.3), 5.12 (d, 1H, J=12.3), 5.28 (d, 1H, J=9.0), 5.47–5.56 (m, 1H), 6.38 (s, 1H), 7.08–7.20 (m, 5H), 7.29–7.42 (m, 5H), 7.44–7.52 (m, 2H), 7.56–7.63 (m, 2H), 7.93–7.98 (m, 2H). Anal. (C$_{36}$H$_{42}$N$_4$O$_6$0.50H$_2$O) C, H, N.

Example 27

Cbz-L-Leu-L-Phe-L-Gln-CH$_2$OC(O)-(2,6-dichlorophenyl)

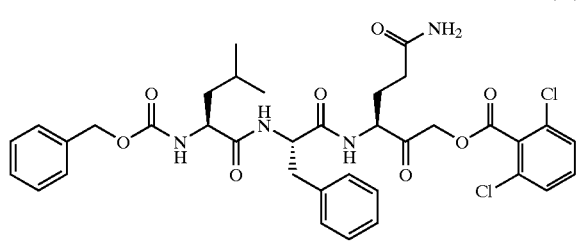

(27)

Preparation of Intermediate Cbz-L-(Tr-Gln)-CHN$_2$:

To a solution of 5.22 g of commercially obtained Cbz-L-(Tr-Gln)-OH (10.0 mmol) in 100 mL of THF at about –15° C. was added 3.0 mL of Et$_3$N (21.6 mmol), followed by the slow addition of 1.64 g of isobutyl chloroformate (12.0 mmol). The reaction mixture was stirred for 40 min before it was filtered to remove the solid formed. Diazomethane in ether, generated from 5.0 g of Diazald (23 mmol) and 5.0 g of KOH, as then added to the filtrate and stirred for 24 h at 23° C. After evaporation of the solvent under reduced pressure, the residue was purified by flash column chromatography, eluting with CH$_2$Cl$_2$/CH$_3$OH (100:1, 600 mL; 100:2, 600 mL; 100:3, 600 mL) to provide 5.37 g of product (98% yield). $^1$H NMR (CDCl$_3$) δ7.15–7.40 (m, 20H), 7.02 (s, 1H), 5.90 (d, 1H), 5.35 (m, 1H), 5.10 (s, 2H), 4.15 (m, 1H), 2.25-2.55 (m, 2H), 2.10 (m, 1H), 1.80 (m, 1H).

Preparation of Intermediate Cbz-L-(Tr-Gln)-CH$_2$Cl:

At 0° C., to a solution of 4.8 g of Cbz-L-(Tr-Gln)-CHN$_2$ (8.8 mmol) in 200 mL of anhydrous Et$_2$O and 30 mL of THF, was added 50 mL of 1.0 M HCl in Et$_2$O slowly. The reaction was completed cleanly after 15 min. After evaporation of the solvent under reduced pressure, the product was obtained and used directly in the next step without further purification. $^1$H NMR (CDCl$_3$) δ7.15–7.40 (m, 20H), 6.95 (s, 1H), 5.95 (d, 1H), 5.10 (s, 2H), 4.40 (m, 1H), 4.20 (s, 2H), 2.25–2.50 (m, 2H), 2.00–2.25 (m, 1H), 1.75–1.95 (m, 1H).

Preparation of Intermediate Cbz-L-(Tr-Gln)-CH$_2$OC(O)-(2,6-dichlorophenyl):

2.40 g of Cbz-L-(Tr-Gln)-CH$_2$Cl (4.3 mmol), 1.07 g of 2,6-dichlorobenzoic acid (5.6 mmol) and 1.5 g of cesium fluoride (10 mmol) were stirred in 20 mL of DMF at 65° C. for 3.5 h. Then, 150 mL of EtOAc was added and the mixture was washed 4 times with brine and dried over Na$_2$SO$_4$. The solvent was removed under reduced pressure and the residue was purified by flash column chromatography (eluting with hexane/EtOAc; 3:1, 800 mL; 2:1, 1800 mL) to provide 1.80 g of product (59% yield). $^1$H NMR (CDCl$_3$) δ7.15–7.40 (m, 23H), 6.90 (s, 1H), 5.90 (d, 1H), 5.15 (s, 2H), 4.85–5.10 (dd, 2H), 4.45 (m, 1H ), 2.35–2.65 (m, 2H), 2.15–2.35 (m, 1H), 1.90–2.10 (m, 1H).

Preparation of Intermediate Cbz-L-Leu-L-Phe-L-(Tr-Gln)-CH$_2$OC(O)-(2,6-dichlorophenyl):

Cbz-L-(Tr-Gln)-CH$_2$OC(O)-(2,6-dichlorophenyl) (0.90 g, 1.0 mmol) was dissolved in 50 mL of EtOH and 20 mL of THF, and ~200 mg of 10% Pd/C and 5.0 mL of 1.0 M HCl in Et$_2$O were added. The mixture was exposed to H$_2$ from a balloon at 23° C. for 4 h. The solids were removed by filtration and the filtrate was concentrated under reduced pressure. The residue was used directly in the next step without further purification.

At 0° C., to a solution of 0.70 g of Cbz-L-Leu-L-Phe-OH (1.70 mmol) and 0.40 g of Et$_3$N (4.0 mmol) in 50 mL of CH$_2$Cl$_2$, was added 0.75 g of BOP reagent (1.70 mmol). The mixture was stirred for 50 min before being mixed with the crude amine product prepared above. After stirring 42 h at 23° C., the solvent was removed under reduced pressure and the residue was purified by flash column chromatography (eluting with a 1:1 mixture of hexane/EtOAc) to give 0.88 g of product (72% yield over two steps). $^1$H NMR (DMSO-d$_6$) δ7.90–8.70 (m, 3H), 7.10–7.50 (m, 29H), 4.75–5.20 (m, 4H), 4.55 (m, 1H), 4.30 (m, 1H), 4.00 (m, 1H), 2.70–3.20 (m, 2H), 0.70–2.50 (m, 13H).

Preparation of Product Cbz-L-Leu-L-Phe-L-Gln-CH$_2$OC(O)-(2,6-dichlorophenyl)

At 0° C., to a solution of 0.80 g of Cbz-L-Leu-L-Phe-L-(Tr-Gln)-CH$_2$OC(O)-(2,6-dichlorophenyl) in 24 mL of CH$_2$Cl$_2$, was added 8 mL of TFA slowly. The yellow mixture was stirred for 2 h, and then NaHCO$_3$ (solid) was added to quench the TFA until the yellow color disappeared. The organic layer was separated and the solid was washed thoroughly with CH$_2$Cl$_2$. The combined organic layers were concentrated and the residue was purified by preparative TLC (eluting with 10:1 CH$_2$Cl$_2$/CH$_3$OH) to give 100 mg of product (17% yield). $^1$H NMR (CH$_3$OH-d$_4$) δ7.10–7.50 (m, 13H), 4.00–5.20 (m, 7H), 2.70–3.25 (m, 2H), 1.75–2.50 (m, 4H), 1.20–1.70 (m, 3H), 0.90 (m, 6H). LC/MS (APCI): 727(M+1)/729=3/2; 537(M-dichlorobenzoic acid).

Example 28

(5-Methylisoxazole-3-carboxyl)-L-Val-L-Phe(4-F)-L-[(S)-Pyrrol-Ala]-2-Benzthiazole

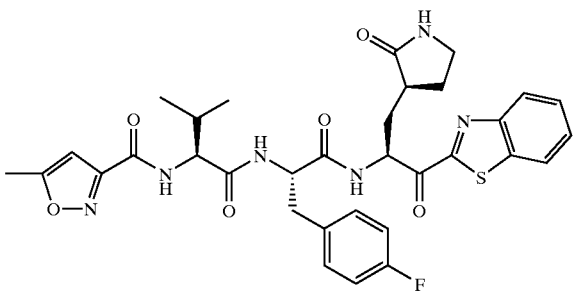

(28)

Preparation of Intermediate Boc-L-(N-2,4-Dimethoxybenzyl)-(S)-Pyrrol-Alaninol-2-Benzthiazole (Z1):

To a solution of Boc-L-[(N-2,4-dimethoxybenzyl)-(S)-Pyrrol-Ala]-2-benzthiazole (T1) (prepared as described in Example 21) (0.252 g, 0.54 mmol, 1 equiv) cooled at –20° C. was added NaBH$_4$ (0.010 g, 0.27 mmol, 0.5 equiv). The reaction mixture was stirred at –20° C. for 20 min, and then was partitioned between saturated H$_2$O (50 mL) and CH$_2$Cl$_2$ (2×50 mL). The organic layer was dried over MgSO$_4$, filtered, and concentrated. The residue was purified by flash column chromatography (gradient elution, 0→2% CH$_3$OH in CH$_2$Cl$_2$) to give Boc-L-(N-2,4-dimethoxybenzyl)-(S)-

Pyrrol-Alaninol-2-benzthiazole (0.199 g, 68% yield) as a white foam. IR (cm$^{-1}$) 3334, 1654, 1508, 1160. $^1$H NMR (CDCl$_3$) (mixture of isomers) δ1.35 (s), 1.46 (s), 1.88–1.97 (m), 2.04–2.10 (m), 2.23–2.28 (m), 2.52–2.60 (m), 2.66–2.74 (m), 3.16–3.28 (m), 3.78 (s), 3.80–3.84 (m), 4.22–4.26 (m), 4.38–4.51 (m), 5.17–5.18 (m), 5.66–5.68 (m), 5.73–5.76 (m), 5.87–5.89 (m), 6.27–6.29 (m), 6.41–6.47 (m), 7.07–7.15 (m), 7.37–7.43 (m), 7.47–7.52 (m), 7.92 (d, J=7.8), 8.01 (d, J=6.9). Anal. (C$_{28}$H$_{35}$N$_3$O$_6$S) C, H, N.

Preparation of Intermediate Boc-L-Val-L-Phe(4-F)-L-(N-2,4-Dimethoxybenzyl)-(S)-Pyrrol-Alaninol-2-Benzthiazole (BB1)

Boc-L-(N-2,4-dimethoxybenzyl)-(S)-Pyrrol-Alaninol-2-Benzthiazole (0.199 g, 0.37 mmol, 1.0 equiv) was dissolved in 1,4-dioxane (3 mL), and a solution of HCl in 1,4-dioxane (4.0 M, 3 mL) was added. The reaction was stirred at 23° C. for 3 h, and then the solvent was removed under reduced pressure. The residue was dissolved in CH$_3$CN (15 mL), cooled to 0° C., and Boc-L-Val-L-Phe(4-F)-OH (prepared from Boc-L-Val-OH and the sodium salt of 4-fluorophenylalanine in a manner analogous to the preparation of Cbz-L-Leu-L-Phe-L-(N-Ac-amino-Ala)-OH described in Example 9) (0.202 g, 0.56 mmol, 1.5 equiv), NMM (0.163 mL, 0.1.48 mmol, 4 equiv) and HATU (0.213 g, 0.56 mmol, 1.5 equiv) were added sequentially. The reaction mixture was stirred at to 0° C. for 40 min, and then the solvent was removed under reduced pressure. The residue was taken up into CH$_2$Cl$_2$ (50 mL), and was washed sequentially with 0.5 N HCl (50 mL), saturated NaHCO$_3$ (50 mL), H$_2$O (50 mL), and brine (50 mL). The organic layer was dried over MgSO$_4$, filtered, and concentrated. The residue was purified by flash column chromatography (2% CH$_3$OH in CH$_2$Cl$_2$) to give Boc-L-Val-L-Phe(4-F)-L-(N-2,4-dimethoxybenzyl)-(S)-Pyrrol-Alaninol-2-benzthiazole (0.280 g, 94% yield). R$_f$=0.59 (10% CH$_3$OH in CH$_2$Cl$_2$). IR (cm$^{-1}$) 3279, 1644, 1158. $^1$H NMR (CDCl$_3$) (mixture of isomers) δ0.51 (d, J=6.6), 0.67 (d, J=6.6), 0.9 (d, J=6.9), 0.95 (d, J=6.6), 1.46 (s), 1.47 (s), 1.59–1.65 (m), 2.08–2.13 (m), 2.87–3.18 (m), 2.94–2.96 (m), 3.02–3.05 (m), 3.18–3.28 (m), 3.90–4.01 (m), 4.23–4.46 (m), 4.88 (m), 5.07–5.12 (m), 5.98 (m), 6.24–6.25 (m), 6.47–6.53 (m), 6.63–6.74 (m), 6.77–6.89 (m), 6.97–7.00 (m), 7.11–7.20 (m), 7.36–7.53 (m), 7.87–8.00 (m), 8.12 (m), 8.76 (m). Anal. (C$_{42}$H$_{52}$FN$_5$O$_8$S.0.50H$_2$O) C, H, N.

Preparation of Intermediate (5-Methylisoxazole-3-carboxyl)-L-Val-L-Phe(4-F)-L-(N-2,4-Dimethoxybenzyl)-(S)-Pyrrol-Alaninol-2-Benzthiazole (BB2): BOC-L-Val-L-Phe(4-F)-L-(N-2,4-dimethoxybenzyl)-(S)-Pyrrol-Alaninol-2-benzthiazole (0.280 g, 0.35 mmol, 1.0 equiv.) was dissolved in 1,4-dioxane (3 mL), and a solution of HCl in 1,4-dioxane (4.0 M, 3 mL) was added. The reaction was stirred at 23° C. for 3 h, and then the solvent was removed under reduced pressure. The residue was dissolved in CH$_2$Cl$_2$ (15 mL), cooled to 0° C., and 2,4,6-collidine (0.093 mL, 0.70 mmol, 2 equiv) and 5-methylisoxazole-3-carboxyl chloride (0.076 g, 0.525 mmol, 1.5 equiv) were added. The reaction mixture was stirred at 0° C. for 30 min, and then was partitioned between saturated H$_2$O (50 mL) and CH$_2$Cl$_2$ (2×50 mL). The combined organic layers were dried over Na$_2$SO$_4$ and were concentrated. Flash column chromatographic purification of the residue (2% CH$_3$OH in CH$_2$Cl$_2$) gave (5-methylisoxazole-3-carboxyl)-L-Val-L-Phe(4-F)-L-(N-2,4-dimethoxybenzyl)-(S)-Pyrrol-Alaninol)-2-benzthiazole (0.182 g, 65% yield) as a white foam. R$_f$0.55 (10% CH$_3$OH in CH$_2$Cl$_2$). IR (cm$^{-1}$) 3281, 1643, 1539, 1209. $^1$H NMR (CDCl$_3$) (mixture of isomers) δ0.57 (d, J=6.9), 0.74 (d, J=6.9), 0.83–0.87 (m), 0.95–0.99 (m), 1.58–1.64 (m), 1.72–1.78 (m), 1.94–2.02 (m), 2.12–2.26 (m), 2.44–2.53 (m), 2.89–3.09 (m), 2.21–3.28 (m), 3.73 (s), 3.80 (s), 4.17–4.49 (m), 4.91–4.94 (m), 5.05–5.16 (m), 5.92 (d, J=4.6), 6.20 (d, J=6.3), 6.42–6.48 (m), 6.63–6.69 (m), 6.74–6.80 (m), 6.93–6.99 (m), 7.02–7.18 (m), 7.35–7.52 (m), 7.88–8.00 (m), 8.16 (d, J=7.5), 8.74 (d, J=5.7). Anal. (C$_{42}$H$_{47}$FN$_6$O$_8$S.0.50H$_2$O) C, H, N.

Preparation of Intermediate (5-Methylisoxazole-3-carboxyl)-L-Val-L-Phe(4-F)-L-[(N-2,4-Dimethoxybenzyl)-(S)-Pyrrol-Ala]-2-Benzthiazole (Y1):

To a solution of Dess-Martin periodinane (0.114 g, 0.27 mmol, 1.2 equiv) in CH$_2$Cl$_2$ (7 mL) was added (5-methylisoxazole-3-carboxyl)-L-Val-L-Phe(4-F)-L-(N-2,4-dimethoxybenzyl)-(S)-Pyrrol-Alaninol-2-benzthiazole (0.182 g, 0.22 mmol, 1 equiv) in CH$_2$Cl$_2$ (3 mL). The reaction mixture was stirred at room temperature for 2 h, and then was partitioned between saturated H$_2$O (50 mL) and CH$_2$Cl$_2$ (2×50 mL). The combined organic layers were dried over Na$_2$SO$_4$ and were concentrated. Flash column chromatographic purification of the residue (2% CH$_3$OH in CH$_2$Cl$_2$) gave (5-methylisoxazole-3-carboxyl)-L-Val-L-Phe(4-F)-L-[(N-2,4-dimethoxybenzyl)-(S)-Pyrrol-Ala]-2-benzthiazole (0.168 g, 94% yield) as white foam. R$_f$=0.51 (10% CH$_3$OH in CH$_2$Cl$_2$). IR (cm$^{-1}$) 3288, 1645, 1509, 1209. $^1$H NMR (CDCl$_3$) δ0.97 (d, 3H, J=6.9), 1.02 (d, 3H, J=6.6), 2.06–2.39 (m, 6H), 2.51 (s, 3H), 3.16–3.17 (m, 3H), 3.25–3.30 (m, 2H), 3.83 (s, 6H), 4.39–4.45 (m, 2H), 4.47–4.49 (m, 1H), 4.89–4.96 (m, 1H), 5.58–5.64 (m, 1H), 6.42–6.51 (m, 3H), 6.78–6.88 (m, 3H), 7.02–7.22 (m, 3H), 7.54–7.64 (m, 2H), 8.00–8.03 (m, 1H), 8.19–8.21 (m, 1H), 8.96 (d, 1H, J=5.7). Anal. (C$_{42}$H$_{45}$FN$_6$O$_8$S.2.6H$_2$O) C, H, N.

Preparation of Product (W2):

To a suspension (5-methylisoxazole-3-carboxyl)-L-Val-L-Phe(4-F)-L-[(N-2,4-dimethoxybenzyl)-(,S)-Pyrrol-Ala]-2-benzthiazole (0.132 g, 0.16 mmol, 1 equiv) in CH$_3$CN (10 mL) and H$_2$O (1 mL) was added DDQ (0.132 g, 0.58 mmol, 3.6 equiv). The reaction mixture was stirred at 60° C. for 5 h, and then was diluted with CH$_2$Cl$_2$ (50 mL) and washed sequentially with saturated NaHCO$_3$ (40 mL) and brine (40 mL). The organic layer was dried over Na$_2$SO$_4$ and was concentrated. The residue was purified by flash column chromatography (gradient elution, 2→4% CH$_3$OH in CH$_2$Cl$_2$) to give (5-methylisoxazole-3-carboxyl)-L-Val-L-Phe(4-F)-L-[(S)-Pyrrol-Ala]-2-benzthiazole (0.011 g, 11%) as a white foam. R$_f$=0.43 (10% CH$_3$OH in CH$_2$Cl$_2$). IR (cm$^{-1}$) 3284, 1682, 1265. $^1$H NMR (CDCl$_3$) δ0.91 (d, 3H, J=6.6), 0.95 (d, 3H, J=6.6), 2.08–2.28 (m, 5H), 2.51–2.56 (m, 5H), 3.03–3.21 (m, 2H), 3.43–3.46 (m, 2H), 4.33–4.38 (m, 1H), 4.89–4.96 (m, 1H), 5.71–5.81 (m, 1H), 6.45 (s, 1H), 6.52 (s, br 1H), 6.79–6.85 (m, 2H), 6.87–6.94 (m, 1H), 7.13–7.17 (m, 2H), 7.55–7.64 (m, 2H), 8.01–8.06 (m, 1H), 8.18–8.21 (m, 1H), 8.31 (d, 1H, J=6.6). HRMS MCs$^+$ 795.1259.

Results of tests conducted using exemplary compounds of the invention are described below.

Biochemical and Biological Evaluation

Inhibition of Rhinovirus 3C Protease

Stock solutions (50 mM, in DMSO) of various compounds were prepared; dilutions were in the same solvent. Recombinant rhinovirus 3C proteases (see Birch et al., "Purification of recombinant human rhinovirus 14 3C protease expressed in *Escherichia coli*," *Protein Expr. Pur.* (1995), vol. 6(5), 609–618) from serotypes 14, 16, and 2 were prepared by the following standard chromatographic procedures: (1) ion exchange using Q Sepharose Fast Flow from Pharmacia; (2) affinity chromatography using Affi-Gel Blue from Biorad; and (3) sizing using Sephadex G-100 from Pharmacia. Each assay sample contained 2% DMSO, 50 mM tris pH 7.6, 1 mM EDTA, a test compound at the indicated concentration, approximately 1 µM substrate, and 50–100 nM protease. The $k_{obs/I}$ values were obtained from reactions initiated by addition of enzyme rather than substrate. RVP activity was measured in the fluorescence resonance energy transfer assay. The substrate was (N-terminal) DABCYL-(Gly-Arg-Ala-Val-Phe-Gln-Gly-Pro-Val-Gly)-EDANS. In the uncleaved peptide, the EDANS fluorescence was quenched by the proximal DABCYL moiety. When the peptide was cleaved, the quenching was relieved, and activity was measured as an increase in fluorescence signal. Data were analyzed using standard non-linear fitting programs (Enzfit), and are shown in the table below. The tabulated data in the column designated $k_{obs}/[I]$ were measured from progress curves in enzyme start experiments.

Antirhinoviral H1-HeLa Cell Culture Assay:

In this cell protection assay, the ability of compounds to protect cells against HRV infection was measured by the XTT dye reduction method, which is described in Weislow et al., *J. Natl. Cancer Inst.* (1989), vol. 81, 577–586.

H1-HeLa cells were infected with HRV-14 at a multiplicity of infection (m.o.i.) of 0.13 (virus particles/cell) or mock-infected with medium only. Infected or mock-infected cells were resuspended at $8 \times 10^5$ cells per mL, and incubated with appropriate concentrations of the compounds to be tested. Two days later, XTT/PMS was added to test plates and the amount of formnazan produced was quantified spectrophotometrically at 450/650 nm. The $EC_{50}$ value was calculated as the concentration of compound that increased the percentage of formazan production in compound-treated, virus-infected cells to 50% of that produced by compound-free, mock-infected cells. The 50% cytotoxic dose ($CC_{50}$) was calculated as the concentration of compound that decreased the percentage of formazan produced in compound-treated, mock-infected cells to 50% of that produced by compound-free, mock-infected cells. The therapeutic index (TI) was calculated by dividing the $CC_{50}$ value by the $EC_{50}$ value.

All strains of human rhinovirus (HRV) for use in this assay were purchased from American Type Culture Collection (ATCC), except for HRV serotype-14 (produced from the infectious cDNA clone constructed by Dr. Robert Rueckert, Institute for Molecular Virology, University of Wisconsin, Madison, Wis.). HRV stocks were propagated and viral assays were performed in H1-HeLa cells (ATCC). Cells were grown in minimal essential medium with 10% fetal bovine serum, available from Life Technologies (Gaithersburg, Md.).

Test results for the HRV assay are shown in the table below.

Anticoxsackieviral Cell Culture Assay:

Coxsackievirus types A-21 (CAV-21) and B3 (CVB3) were purchased from American Type Culture Collection (ATCC, Rockville, Md.). Virus stocks were propagated and antiviral assays were performed in H1-HeLa cells (ATCC). Cells were grown in minimal essential medium with 10% fetal bovine serum (Life Technologies, Gaithersburg, Md.).

The ability of compound 28 to protect cells against either CAV-21 or CVB3 infection was measured by the XTT dye reduction method. This method is described in Weislow et al., *J. Natl. Cancer Inst.* (1989), vol. 81, 577–586. H1-HeLa cells were infected with CAV-21 or CVB3 at a multiplicity of infection (m.o.i.) of 0.025 or 0.075, respectively, or mock-infected with medium only. H1-HeLa cells were plated at $4 \times 10^4$ cells per well in a 96-well plate and incubated with appropriate concentrations of the test compound. One day (CVB3) or two days (CAV-21) later, XTT/PMS was added to test plates and the amount of formazan produced was quantified spectrophotometrically at 450/650 nm. The $EC_{50}$ was calculated as the concentration of compound that increased the formazan production in compound-treated, virus-infected cells to 50% of that produced by compound-free, uninfected cells. The 50% cytotoxic dose ($CC_{50}$) was calculated as the concentration of compound that decreased formazan production in compound-treated, uninfected cells to 50% of that produced in compound-free, uninfected cells. The therapeutic index (TI) was calculated by dividing the $CC_{50}$ by the $EC_{50}$.

Anti-Echoviral and Anti-Enteroviral Cell Culture Assays

Echovirus type 11 (ECHO 11) was purchased from ATCC (Rockville, Md.). Virus stocks were propagated and antiviral assays were performed in MRC-5 cells (ATCC). Cells were grown in minimal essential medium with 10% fetal bovine serum (Life Technologies, Gaithersburg, Md.).

The ability of compound 28 to protect cells against ECHO 11 infection was measured by the XTT dye reduction method (Weislow et al., *J. Natl. Cancer Inst.* (1989), vol. 81, 577–586). MRC-5 cells were infected with ECHO 11 at an m.o.i. of 0.003 or 0.004, respectively, or mock-infected with medium only. Infected or uninfected cells were added at $1 \times 10^4$ cells per well and incubated with appropriate concentrations of compound. Four days later, XTT/PMS was added to test plates, and the amount of formazan produced was quantified spectrophotometrically at 450/650 nm. The $EC_{50}$ was calculated as the concentration of compound that increased the formazan production in compound-treated, virus-infected cells to 50% of that produced by compound-free, uninfected cells. The 50% cytotoxic dose ($CC_{50}$) was calculated as the concentration of compound that decreased formazan production in compound-treated, uninfected cells to 50% of that produced in compound-free, uninfected cells. The therapeutic index (TI) was calculated by dividing the $CC_{50}$ by the $EC_{50}$.

Activity of the compounds against enterovirus type 70 (EV 70) may be measured by the same assay as described above in this section. Enterovirus type 70 (EV 70) may be obtained from the American Type Culture Collection ATCC (Rockville, Md.).

Results obtained for the compounds of the invention may be compared to results obtained in the same manner for control compounds WIN 5171 1, WIN 52084, and WIN 54954 (obtained from Sterling-Winthrop Pharmaceuticals), Pirodavir (obtained from Janssen Pharmaceuticals), and Pleconaril (prepared according to the method described in Diana et al., *J. Med. Chem.* (1995), vol. 38, 1355). Antiviral data obtained for the test compounds are shown in the table below. The designation "ND" indicates that a value was not determined for that compound, and the designation "NA" means not applicable.

TABLE

| Compd. # | Virus serotype | $k_{obs}/[I]$ $(M^{-1}s^{-1})^b$ | $K_i$ $(\mu M)^b$ | $EC_{50}$ $(\mu M)$ | $CC_{50}$ $(\mu M)$ | TI |
|---|---|---|---|---|---|---|
| 1 | HRV-14[a] | NA | 9 | ND | ND | ND |
| 2 | HRV-14 | NA | 50 | ND | ND | ND |
| 3 | HRV-14 | slow | NA | >25 | 25 | NA |
| 4 | HRV-14 | NA | 16.3 | ND | ND | ND |
| 5 | HRV-14 | NA | 138 | ND | ND | ND |
| 6 | HRV-14 | NA | 4.8 | ND | ND | ND |
| 7 | HRV-14 | NA | 71 | ND | ND | ND |
| 8 | HRV-14 | NA | 80 | ND | ND | ND |
| 9 | HRV-14 | NA | 1.7 | >25 | 25 | NA |
|  | HRV-16 | NA | 0.31 | >25 | ND | NA |
|  | HRV-2 | NA | 0.90 | ND | ND | ND |
|  | HRV-89 | NA | 0.48 | ND | ND | ND |
| 10 | HRV-14 | NA | 20 | 251 | >320 | >1 |
| 11 | HRV-14 | NA | >110 | ND | ND | ND |
| 12 | HRV-14 | NA | 10.7 | 39 | 80 | 2 |
| 13 | HRV-14 | NA | 24 | >56 | 56 | NA |
|  | HRV-16 | NA | 4 | ND | ND | ND |
|  | HRV-2 | NA | 13.3 | ND | ND | ND |
| 14 | HRV-14 | NA | 0.065 | >100 | >100 | NA |
|  | HRV-16 | NA | 0.322 | ND | ND | ND |
|  | HRV-2 | NA | 0.124 | ND | ND | ND |
|  | HRV-89 | NA | 0.76 | >100 | >100 | NA |
| 15 | HRV-14 | NA | 0.098 | >100 | >100 | NA |
| 16 | HRV-14 | NA | 0.035 | >100 | >100 | NA |
| 17 | HRV-14 | NA | 0.075 | >100 | >100 | NA |
| 18 | HRV-14 | NA | 9.1 | >20 | 20 | NA |
|  | HRV-16 | NA | 6.7 | ND | ND | ND |
|  | HRV-2 | NA | 11 | ND | ND | ND |
|  | HRV-89 | NA | 14 | ND | ND | ND |
| 19 | HRV-14 | NA | 27 | ND | ND | ND |
|  | HRV-16 | NA | 27 | ND | ND | ND |
|  | HRV-2 | NA | 12.9 | ND | ND | ND |
|  | HRV-89 | NA | 20.6 | ND | ND | ND |
| 20 | HRV-14 | NA | 3.5 | 17.4 | >100 | >6 |
| 21 | HRV-14 | NA | 0.065 | 3.2 | >320 | >100 |
| 22 | HRV-14 | NA | 0.70 | 7.9 | 240 | 30 |
| 23 | HRV-14 | NA | 0.17 | 4.0 | 200 | 50 |
| 24 | HRV-14 | NA | 0.65 | >10 | >10 | NA |
| 25 | HRV-14 | NA | 4.7 | >10 | >10 | NA |
| 26 | HRV-14 | NA | 3.22 | >10 | >10 | NA |
| 27 | HRV-14 | 2500 | NA | ND | ND | ND |
| 28 | HRV-14 | NA | 0.0045 | 0.335 | 251 | 749 |
|  | HRV-1A | NA | ND | 0.337 | 251 | 744 |
|  | HRV-10 | NA | ND | 0.253 | 251 | 992 |
|  | CVB3[c] | NA | ND | 5.79 | 251 | 43 |
|  | CAV-21[d] | NA | ND | 4.67 | 251 | 53 |
|  | ECHO-11[e] | NA | ND | 0.821 | 251 | 305 |
| WIN51711 | HRV-14 | NA | ND | 0.78 | >60 | >77 |
| WIN52084 | HRV-14 | NA | ND | 0.07 | >10 | >143 |
| WIN54954 | HRV-14 | NA | ND | 2.13 | >63 | >30 |
| Pirodavir | HRV-14 | NA | ND | 0.03 | >10 | >300 |
| Pleconaril | HRV-14 | NA | ND | 0.01 | >10 | >1000 |

Notes:
[a] HRV = human rhinovirus of designated serotype.
[b] 3C Protease inhibition activity.
[c] CVB3 = coxsackievirus B3.
[d] CAV-21 = coxsackievirus A21.
[e] ECHO-11 = echovirus 11.

While the invention has been described in terms of preferred embodiments and specific examples, those skilled in the art will recognize that various changes and modifications can be made without departing from the spirit and scope of the invention. Thus, the invention should be understood as not being limited by the foregoing detailed description, but as being defined by the appended claims and their equivalents.

What is claimed is:

1. A compound of the formula:

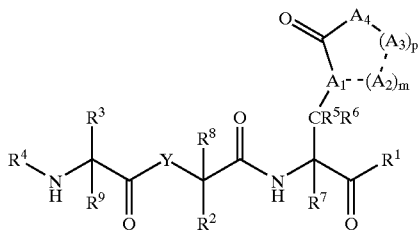

wherein:

Y is —N(R$^y$)—, —C(R$^y$)(R$^y$)—, or —O—, where each R$^y$ is independently H or lower alkyl;

R$^1$ is selected from optionally substituted benzothiazole and thiazole;

R$^2$ and R$^8$ are each independently selected from H, F, and optionally substituted alkyl, cycloalkyl, heterocycloalkyl, aryl, and heteroaryl;

R$^3$ and R$^9$ are each independently selected from H and optionally substituted alkyl, cycloalkyl, heterocycloalkyl, aryl, heteroaryl, —OR$^{17}$, —SR$^{17}$, —NR$^{17}$R$^{18}$, —NR$^{19}$NR$^{17}$R$^{18}$, and —NR$^{17}$OR$^{18}$ where R$^{17}$, R$^{18}$, and R$^{19}$ are each independently selected from H, alkyl, cycloalkyl, heterocyeloalkyl, aryl, heteroaryl, and acyl;

R$^4$ is a suitable organic moiety selected from hydroxy, alkyl, oxo, cycloalkyl, heteaocycloalkyl, aryl, heteroaryl, acyl, sulfonyl, mercapto, alkylthio, alkoxy, carboxy, amino, alkylamino, dialkylamino, carbamoyl, arylthio and heteroarylthio, wherein sulfonyl is —SO$_2$R, where R is selected from hydroxy, halogen, alkyl, acyl, alkylthio, alkoxy, cycloalkyl, heterocycloalkyl, aryl, heteroaryl, carboxy, amino, alkylamino, dialkylamino, carbamoyl, aryloxy, heteroaryloxy, arylthio and heteroarylthio;

each of R$^5$, R$^6$ and R$^7$ is independently H, F, or lower alkyl;

m is 1;

p is 1;

A$^1$ is CH or N;

A$_2$ is selected from C(R$^{10}$)(R$^{11}$) and N(R$^{12}$);

A$_3$ is independently selected from C(R$^{10}$)(R$^{11}$) and N(R$^{12}$); where R$^{10}$, R$^{11}$ and R$^{12}$ are each independently H or lower alkyl;

A$_4$ is selected from N(R$^{13}$) and C(R$^{10}$)(R$^{11}$); where R$^{10}$, R$^{11}$ and R$^{12}$ are each independently H or lower alkyl, R$^{13}$ is H, alkyl, aryl, or acyl, and R$^{14}$ is H, alkyl, or aryl;

provided that A$_1$, (A$_2$)$_m$, (A$_3$)$_p$, and A$_4$ together form a pyrrolidinone ring;

or a prodrug, pharmaceutically acceptable salt or pharmaceutically acceptable solvate thereof.

2. A compound, prodrug, pharmaceutically acceptable salt or pharmaceutically acceptable solvate according to claim 1, wherein R$^7$, R$^8$, and R$^9$ are each H.

3. A compound of the formula:

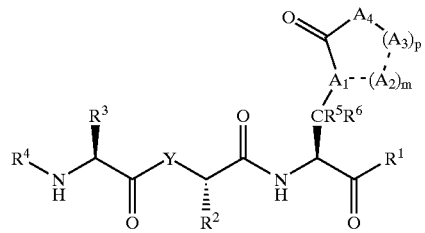

wherein R$^1$, R$^2$, R$^3$, R$^4$, R$^5$, R$^6$, A$_1$, A$_2$, A$_3$, A$_4$, m, p and Y are as defined in claim 1;

or a prodrug, pharmaceutically acceptable salt or pharmaceutically acceptable solvate thereof.

4. A compound, prodrug, pharmaceutically acceptable salt or pharmaceutically acceptable solvate according to claim 3, wherein R$^1$ is an optionally substituted thiazole.

5. A compound, prodrug, pharmaceutically acceptable salt or pharmaceutically acceptable solvate according to claim 3, wherein R$^2$ is selected from unsubstituted and substituted benzyl groups.

6. A compound, prodrug, pharmaceutically acceptable salt or pharmaceutically acceptable solvate according to claim 5, wherein R$^2$ is a benzyl group substituted with one or two substituents independently selected from lower alkyl, lower alkoxy, and halogen.

7. A compound, prodrug, pharmaceutically acceptable salt or pharmaceutically acceptable solvate according to claim 3, wherein R$^3$ is optionally substituted alkyl or arylmethyl.

8. A compound, prodrug, pharmaceutically acceptable salt or pharmaceutically acceptable solvate according to claim 7, wherein R$^3$ is selected from 2-propyl, 2methyl-2propyl, 2methyl-1propyl, and unsubstituted and substituted phenylmethyl and naphthylmethyl.

9. A compound, prodrug, pharmaceutically acceptable salt or pharmaceutically acceptable solvate according to claim 3, wherein R$^4$ is selected from benzyloxycarbonyl, arylcarbonyl, and heteroarylcarbonyl.

10. A compound, prodrug, pharmaceutically acceptable salt or pharmaceutically acceptable solvate according to claim 9, wherein R$^4$ is heteroarylcarbonyl, where the heteroaryl moiety is a five-membered heterocycle having from one to three heteroatoms selected from O, N, and S.

11. A compound, prodrug, pharmaceutically acceptable salt or pharmaceutically acceptable solvate according to claim 10, wherein R$^4$ is heteroarylcarbonyl, where the heteroaryl moiety is a five-membered heterocycle having at least one nitrogen heteroatom and at least one oxygen heteroatom.

12. A compound, prodrug, pharmaceutically acceptable salt or pharmaceutically acceptable solvate according to claim 10, wherein R$^4$ is heteroarylcarbonyl, where the heteroaryl moiety is an unsubstituted or substituted 1,2 oxazolyl, 1,3-oxazolyl, 1,2,3-oxadiazolyl, 1,2,4-oxadiazolyl, or 1,2,5-oxadiazolyl.

13. A compound, prodrug, pharmaceutically acceptable salt or pharmaceutically acceptable solvate according to claim 10, wherein R$^4$ is heteroarylcarbonyl, where the heteroaryl moiety is selected from unsubstituted and monomethyl-substituted 1,2,4-oxadiazolyl.

14. A compound, prodrug, pharmaceutically acceptable salt or pharmaceutically acceptable solvate according to claim 10, wherein R$^4$ is heteroarylcarbonyl, where the heteroaryl moiety is selected from 3-isoxazolyl and 5-isoxazolyl, each unsubstituted or substituted with one or two substituents selected from methyl groups and halogens.

15. A compound, prodrug, pharmaceutically acceptable salt or pharmaceutically acceptable solvate according to claim 3, wherein the moiety:

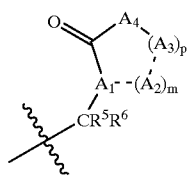

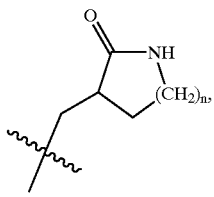

is where n is 1.

16. A compound, prodrug, pharmaceutically acceptable salt or pharmaceutically acceptable solvate according to claim 15, wherein said moiety

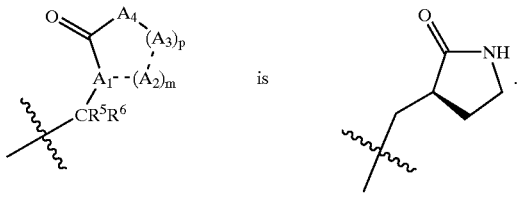

17. A compound according to claim 16 of the formula:

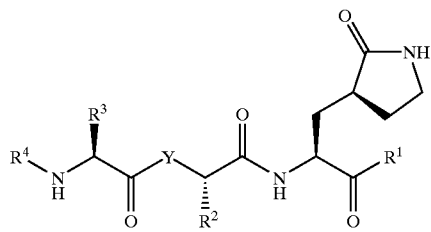

or a prodrug, pharmaceutically acceptable salt or pharmaceutically acceptable solvate thereof.

18. A compound, prodrug, pharmaceutically acceptable salt or pharmaceutically acceptable solvate according to claim 17 wherein: $R^1$ is optionally substituted benzothiazole and thiazole; $R^2$ is an unsubstituted, mono-substituted, or disubstituted benzyl group; $R^3$ is 2-propyl, 2-methyl-2-propyl, 2-methyl-1-propyl, or arylmethyl; and $R^4$ is benzyloxycarbonyl, arylcarbonyl, or heteroarylcarbonyl.

19. A compound of claim 1 selected from

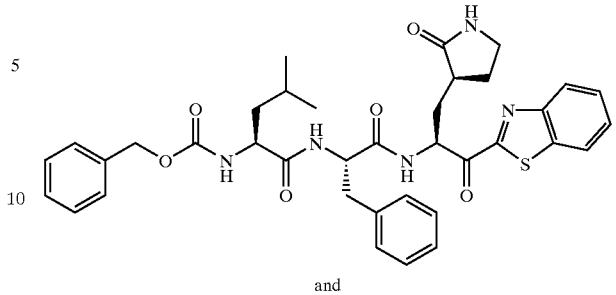

and

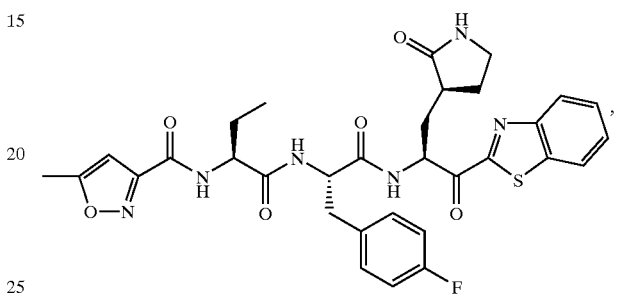

and prodrugs, pharmaceutically acceptable salts and pharmaceutically acceptable solvates thereof.

20. A compound, prodrug, pharmaceutically acceptable salt or pharmaceutically acceptable solvate according to claim 1, wherein Y is $N(R^y)$.

21. A compound, prodrug, pharmaceutically acceptable salt or pharmaceutically acceptable solvate according to claim 20, wherein $R^y$ is H or methyl.

22. A compound according to claim 20 of the formula:

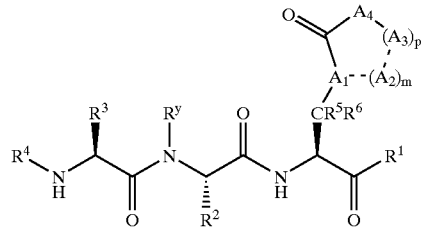

or a prodrug, pharmaceutically acceptable salt or pharmaceutically acceptable solvate thereof.

23. A compound, prodrug, pharmaceutically acceptable salt or pharmaceutically acceptable solvate according to claim 1, wherein Y is O.

24. A compound, prodrug, pharmaceutically acceptable salt or pharmaceutically acceptable solvate according to claim 3, wherein Y is O.

25. A compound, prodrug, pharmaceutically acceptable salt or pharmaceutically acceptable solvate according to claim 1, wherein Y is —C(R$^y$)(R$^y$)—.

26. A compound, prodrug, pharmaceutically acceptable salt or pharmaceutically acceptable solvate according to claim 3, wherein Y is —C(R$^y$)(R$^y$)—.

27. A compound according to claim 1 having antipicornaviral activity corresponding to an EC$_{50}$ less than or equal to 100 μM in an H1-HeLa cell culture assay.

28. A pharmaceutical composition comprising:
(a) a therapeutically effective amount of at least one antipicornaviral agent selected from compounds, prodrugs, pharmaceutically acceptable salts and pharmaceutically acceptable solvates defined in claim 1; and
(b) a pharmaceutically acceptable carrier, diluent, vehicle, or excipient.

* * * * *